United States Patent
Kahvejian et al.

(10) Patent No.: US 11,013,717 B1
(45) Date of Patent: May 25, 2021

(54) METHODS AND COMPOSITIONS FOR TREATING CANCER USING SERCA PUMP INHIBITORS

(71) Applicant: Flagship Pioneering Innovations V, Inc., Cambridge, MA (US)

(72) Inventors: Avak Kahvejian, Lexington, MA (US); Jordi Mata-Fink, Baltimore, MD (US); Jonathan Barry Hurov, Bedford, MA (US); Chengyi Jenny Shu, Cambridge, MA (US); Eric Franklin Zhu, Cambridge, MA (US); Katherine Mary Molloy, Somerville, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/264,572

(22) Filed: Jan. 31, 2019

Related U.S. Application Data

(60) Provisional application No. 62/624,652, filed on Jan. 31, 2018.

(51) Int. Cl.
| | |
|---|---|
| *A61K 31/40* | (2006.01) |
| *A61K 31/365* | (2006.01) |
| *A61K 38/46* | (2006.01) |
| *A61K 31/4184* | (2006.01) |
| *A61K 31/407* | (2006.01) |

(52) U.S. Cl.
CPC .......... *A61K 31/365* (2013.01); *A61K 31/407* (2013.01); *A61K 31/4184* (2013.01); *A61K 38/465* (2013.01)

(58) Field of Classification Search
CPC .............................. C07D 249/04; A61K 31/40
See application file for complete search history.

(56) References Cited

FOREIGN PATENT DOCUMENTS

| WO | WO-2010/088450 A2 | 8/2010 |
| WO | WO2010088450 | * 8/2010 |
| WO | WO-2018/022666 A1 | 2/2018 |

OTHER PUBLICATIONS

Kmonickova et al., Eur J Pharmacol, 2008, 588(1): 85-92.*
Kmonickova et al., Fitoterapia, 2010, 81(8): 1213-1219.*
Boorman et al., "Myelotoxicity and macrophage alteration in mice exposed to ochratoxin A," Toxicol Appl Pharmacol. 72(2):304-12 (1984).
Denmeade et al., "Prostate-specific antigen-activated thapsigargin prodrug as targeted therapy for prostate cancer," J Natl Cancer Inst. 95(13):990-1000 (2003).
Ghosh et al., "Nifetepimine, a dihydropyrimidone, ensures CD4+ T cell survival in a tumor microenvironment by maneuvering sarco(endo)plasmic reticulum Ca2+ ATPase (SERCA)," J Biol Chem. 287(39):32881-96 (2012).
Hymery et al., "Cytotoxicity and immunotoxicity of cyclopiazonic acid on human cells," Toxicol In Vitro. 28(5):940-7 (2014).
Kim et al., "Thapsigargin increases IL-2 production in T Cells at nanomolar concentrations," Immune Netw. 18(4):e26 (2018) (7 pages).
Li et al., "SBF-1 exerts strong anticervical cancer effect through inducing endoplasmic reticulum stress-associated cell death via targeting sarco/endoplasmic reticulum Ca(2+)-ATPase 2," Cell Death Dis. 5:e1581 (2014) (10 pages).
Oh et al., "Endoplasmic reticulum stress controls M2 macrophage differentiation and foam cell formation," J Biol Chem. 287(15):11629-41 (2012).
Paula et al., "Novel phenolic inhibitors of the sarco/endoplasmic reticulum calcium ATPase: identification and characterization by quantitative structure-activity relationship modeling and virtual screening," J Enzyme Inhib Med Chem. 30(1):1-8 (2015) (9 pages).
Zhao et al., "Dual-Targeting to Cancer Cells and M2 Macrophages via Biomimetic Delivery of Mannosylated Albumin Nanoparticles for Drug-Resistant Cancer Therapy," Adv Funct Mater. 27(44):1700403 (2017) (15 pages).

* cited by examiner

*Primary Examiner* — Rei Tsang Shiao
(74) *Attorney, Agent, or Firm* — Clark & Elbing LLP

(57) ABSTRACT

The present invention provides methods for treating cancer using sarco/endoplasmic reticulum $Ca^{2+}$-ATPase (SERCA) pump inhibitors, such as SERCA pump inhibitory antibodies, among others. The invention also features compositions containing SERCA pump inhibitors, methods of diagnosing patients with SERCA pump-associated cancer, and methods of predicting the response of cancer in a subject to treatment with SERCA pump inhibitors.

10 Claims, No Drawings

METHODS AND COMPOSITIONS FOR TREATING CANCER USING SERCA PUMP INHIBITORS

CROSS-REFERENCE

This application claims the benefit of U.S. Provisional Application No. 62/624,652, filed Jan. 31, 2018, which is incorporated herein by reference in its entirety.

BACKGROUND

Cancer is still one of the deadliest threats to human health. In 2012, there were 14 million new cases of cancer worldwide and 8.2 million cancer-related deaths. The number of new cancer cases is expected to rise to 22 million by 2030, and worldwide cancer deaths are projected to increase by 60%. Thus, there remains a need in the field for treatments for cancer.

SUMMARY OF THE INVENTION

The present invention provides methods for treating cancer using sarco/endoplasmic reticulum $Ca^{2+}$-ATPase (SERCA) pump inhibitors, such as SERCA pump inhibitory antibodies, among others. The invention also features compositions containing SERCA pump inhibitors, methods of diagnosing patients with SERCA pump-associated cancer, and methods of predicting the response of cancer in a subject to treatment with SERCA pump inhibitors.

In a first aspect, the invention provides a method of treating a subject with cancer, by administering to the subject an effective amount of a SERCA pump inhibitor.

In another aspect, the invention provides a method of treating a subject with cancer by contacting an immune cell, tumor, tumor microenvironment, site of metastasis, lymph node, spleen, secondary lymphoid organ, or tertiary lymphoid organ with an effective amount of a SERCA pump inhibitor.

In another aspect, the invention provides a method of treating a subject identified as having cancer by administering to the subject an effective amount of a SERCA pump inhibitor.

In another aspect, the invention provides a method of treating a subject identified as having cancer by contacting an immune cell, tumor, tumor microenvironment, site of metastasis, lymph node, spleen, secondary lymphoid organ, or tertiary lymphoid organ cell with an effective amount of a SERCA pump inhibitor.

In another aspect, the invention provides a method of increasing levels of one or more pro-inflammatory cytokine in a subject in need thereof by administering to the subject an effective amount of a SERCA pump inhibitor. In some embodiments, the subject is a subject with SERCA pump-associated cancer. In some embodiments, the one or more pro-inflammatory cytokine includes interferon gamma (IFNγ). In some embodiments, the method further includes determining the level of one or more pro-inflammatory cytokine after administration of the SERCA pump inhibitor.

In another aspect, the invention provides a method of increasing T cell activation in a subject in need thereof by administering to the subject an effective amount of a SERCA pump inhibitor. In some embodiments, the subject is a subject with SERCA pump-associated cancer. In some embodiments, the method further includes evaluating T cell activation after administration of the SERCA pump inhibitor.

In another aspect, the invention provides a method of treating a subject with cancer by: a) identifying a subject with SERCA pump-associated cancer; and b) administering to the subject an effective amount of a SERCA pump inhibitor.

In another aspect, the invention provides a method of treating a subject with cancer by: a) identifying a subject with SERCA pump-associated cancer; and b) contacting an immune cell, tumor, tumor microenvironment, site of metastasis, lymph node, spleen, secondary lymphoid organ, or tertiary lymphoid organ with an effective amount of a SERCA pump inhibitor.

In another aspect, the invention provides a method of treating a subject with SERCA pump-associated cancer by administering to the subject an effective amount of a SERCA pump inhibitor.

In another aspect, the invention provides a method of treating a subject with SERCA pump-associated cancer by contacting an immune cell, tumor, tumor microenvironment, site of metastasis, lymph node, spleen, secondary lymphoid organ, or tertiary lymphoid organ with an effective amount of a SERCA pump inhibitor.

In some embodiments of any of the above aspects, the method includes increasing an immune cell activity.

In another aspect, the invention provides a method of increasing an immune cell activity in a subject in need thereof by administering to the subject an effective amount of a SERCA pump inhibitor.

In another aspect, the invention provides a method of increasing an immune cell activity in a subject in need thereof by contacting an immune cell with an effective amount of a SERCA pump inhibitor.

In some embodiments of any of the above aspects, the immune cell activity is one or more of immune cell proliferation, differentiation, activation, and cytokine production. In some embodiments, the cytokine is IFNγ. In some embodiments, increased production of IFNγ has a pro-inflammatory effect.

In another aspect, the invention provides a method of decreasing SERCA pump expression in an immune cell in a subject by administering to the subject an effective amount of a SERCA pump inhibitor.

In another aspect, the invention provides a method of decreasing SERCA pump expression in an immune cell in a subject by contacting the immune cell with an effective amount of a SERCA pump inhibitor.

In another aspect, the invention provides a method of increasing inflammation in a subject in need thereof by administering to the subject an effective amount of a SERCA pump inhibitor.

In another aspect, the invention provides a method of increasing inflammation in a subject by contacting an immune cell, tumor, tumor microenvironment, site of metastasis, lymph node, spleen, secondary lymphoid organ, or tertiary lymphoid organ with an effective amount of a SERCA pump inhibitor.

In some embodiments of any of the above aspects, the method includes contacting an immune cell with an effective amount of a SERCA pump inhibitor. In some embodiments of any of the above aspects, the method includes contacting a tumor with an effective amount of a SERCA pump inhibitor. In some embodiments of any of the above aspects, the method includes contacting a tumor microenvironment with an effective amount of a SERCA pump inhibitor. In some embodiments of any of the above aspects, the method includes contacting a site of metastasis with an effective amount of a SERCA pump inhibitor. In some embodiments of any of the above aspects, the method includes contacting a lymph node with an effective amount of a SERCA pump inhibitor. In some embodiments of any of the above aspects, the method includes contacting a spleen with an effective amount of a SERCA pump inhibitor. In some embodiments of any of the above aspects, the method includes contacting a secondary lymphoid organ with an effective amount of a SERCA pump inhibitor. In some embodiments of any of the above aspects, the method includes contacting a tertiary lymphoid organ with an effective amount of a SERCA pump inhibitor.

In some embodiments of any of the above aspects, the cancer is SERCA pump-associated cancer.

In some embodiments of any of the above aspects, the immune cell is an effector T cell, a helper T cell, a cytotoxic T cell (e.g., a CD8+ T cell), a Th1 cell, a Th2 cell, or a Th17 cell. In another aspect, the invention provides a method of increasing T cell production of one or more pro-inflammatory cytokine by contacting a T cell with an effective amount of a SERCA pump inhibitor. In some embodiments, the T cell is a T cell expressing one or more one or more SERCA pumps (e.g., one or more of ATP2A1, ATP2A2, or ATP2A3). In some embodiments, the one or more pro-inflammatory cytokine includes IFNγ.

In another aspect, the invention provides a method of increasing T cell activation by contacting a T cell with an effective amount of a SERCA pump inhibitor. In some embodiments, the T cell is a T cell expressing one or more one or more SERCA pumps (e.g., one or more of ATP2A1, ATP2A2, or ATP2A3).

In some embodiments of any of the above aspects, the SERCA pump-associated cancer is a cancer associated with expression of one or more SERCA pumps (e.g., expression of one or more of ATP2A1, ATP2A2, or ATP2A3 in an immune cell, e.g., a T cell). In some embodiments of any of the above aspects, the SERCA pump-associated cancer is a cancer associated with overexpression of one or more SERCA pumps (e.g., overexpression of one or more of ATP2A1, ATP2A2, or ATP2A3 in an immune cell).

In some embodiments of any of the above aspects, the SERCA pump-associated cancer is infiltrated with immune cells (e.g., T cells, macrophages, monocytes, or myeloid-derived suppressor cells) that express or overexpress one or more SERCA pump (e.g., ATP2A1, ATP2A2, and/or ATP2A3).

In another aspect, the invention provides a method of treating a subject with an immune cell-infiltrated tumor by administering to the subject an effective amount of a SERCA pump inhibitor.

In another aspect, the invention provides a method of treating a subject with an immune cell-infiltrated tumor by contacting the tumor with an effective amount of a SERCA pump inhibitor.

In another aspect, the invention provides a method of treating a subject with an immune cell-infiltrated tumor by contacting an immune cell in the tumor with an effective amount of a SERCA pump inhibitor.

In another aspect, the invention provides a method of treating a subject with a T cell-infiltrated tumor by administering to the subject an effective amount of a SERCA pump inhibitor.

In another aspect, the invention provides a method of treating a subject with a T cell-infiltrated tumor by contacting the tumor with an effective amount of a SERCA pump inhibitor.

In another aspect, the invention provides a method of treating a subject with a T cell-infiltrated tumor by contacting a T cell in the tumor with an effective amount of a SERCA pump inhibitor.

In some embodiments of any of the above aspects, the immune cell is an effector T cell, a helper T cell, a cytotoxic T cell, a Th1 cell, a Th2 cell, or a Th17 cell.

In some embodiments of any of the above aspects, the method further includes contacting an immune cell isolated from the subject with a SERCA pump inhibitor and evaluating the response of the immune cell prior to administration of the SERCA pump inhibitor.

In another aspect, the invention provides a method of treating a subject with cancer, the method including the steps of a) contacting an immune cell isolated from the subject with a SERCA pump inhibitor and evaluating a response of the immune cell; and b) administering to the subject an effective amount of a SERCA pump inhibitor if the response of the immune cell is modulated by the SERCA pump inhibitor (e.g., if the SERCA pump inhibitor increases migration, polarization (e.g., polarization toward an inflammatory state), proliferation, recruitment, differentiation, tumor homing, activation, cytokine production (e.g., pro-inflammatory cytokine production, e.g., IFNγ production), degranulation, maturation, antibody-dependent cell-mediated cytotoxicity (ADCC), antibody-dependent cell-mediated phagocytosis (ADCP), and/or antigen presentation).

In another aspect, the invention provides a method of treating a subject with cancer, the method including the steps of a) contacting an immune cell isolated from the subject with a SERCA pump inhibitor and evaluating a response of the immune cell; and b) contacting an immune cell, a tumor, a tumor microenvironment, a site of metastasis, a lymph node, a spleen, a secondary lymphoid organ, or a tertiary lymphoid organ with an effective amount of a SERCA pump inhibitor if the response of the immune cell is modulated by the SERCA pump inhibitor (e.g., if the SERCA pump inhibitor increases migration, polarization (e.g., polarization toward an inflammatory state), proliferation, recruitment, differentiation, tumor homing, activation, cytokine production (e.g., pro-inflammatory cytokine production, e.g., IFNγ production), degranulation, maturation, ADCC, ADCP, and/or antigen presentation).

In another aspect, the invention provides a method of treating a subject with cancer, the method including the steps of a) contacting an immune cell or isolated from the subject with a SERCA pump inhibitor and evaluating a response of the immune cell; and b) administering to the subject an effective amount of a SERCA pump inhibitor.

In another aspect, the invention provides a method of predicting the response of a cancer in a subject to treatment with a SERCA pump inhibitor by contacting an immune cell isolated from the subject with a SERCA pump inhibitor and evaluating the response of the immune cell.

In another aspect, the invention provides a method of predicting the response of a cancer in a subject to treatment with a SERCA pump inhibitor by contacting an immune cell-infiltrated tumor biopsy isolated from the subject with a SERCA pump inhibitor and evaluating the response of the immune cell.

In some embodiments of any of the above aspects, the evaluating includes assessing tumor growth, tumor proliferation, tumor metastasis, tumor invasion, tumor migration, tumor death, tumor autophagy, immune cell migration, immune cell proliferation, immune cell recruitment, immune cell differentiation, immune cell activation, immune cell polarization, immune cell tumor egress, immune cell cytokine production, immune cell SERCA pump expression (e.g., the expression of one or more of ATP2A1, ATP2A2, or ATP2A3), immune cell ADCC, and/or immune cell ADCP.

In another aspect, the invention provides a method of predicting the response of a cancer in a subject to treatment with a SERCA pump inhibitor by: a) isolating an immune cell or an immune-cell infiltrated tumor biopsy from the subject; b) measuring the expression of one or more SERCA pumps (e.g., the expression of one or more of ATP2A1, ATP2A2, or ATP2A3) in the immune cell; and c) comparing SERCA pump expression in the immune cell to a reference, wherein increased expression of one or more SERCA pumps in the immune cell as compared to the reference indicates that the subject will respond to treatment with a SERCA pump inhibitor.

In another aspect, the invention provides a method of determining if an immune cell expresses a functional SERCA pump by contacting the immune cell with a radio-labeled ligand (e.g., [3H]ryanodine) and evaluating ligand binding to the immune cell. In some embodiments, binding of the ligand to the immune cell indicates that the immune cell expresses a functional SERCA pump (e.g., a SERCA pump that is capable of ligand binding).

In another aspect, the invention provides a method of characterizing a cancer in a subject, the method including the steps of: a) isolating an immune cell or an immune-cell infiltrated tumor biopsy from the subject; b) measuring the expression of one or more SERCA pumps (e.g., the expression of one or more of ATP2A1, ATP2A2, or ATP2A3) in the immune cell; and c) comparing SERCA pump expression in the immune cell to a reference, wherein increased expression of one or more SERCA pumps in the immune cell as compared to the reference indicates that the subject has SERCA pump-associated cancer.

In another aspect, the invention provides a method of identifying a subject as having SERCA pump-associated cancer, the method including the steps of: a) isolating an immune cell or an immune-cell infiltrated tumor biopsy from the subject; b) measuring the expression of one or more SERCA pumps (e.g., the expression of one or more of ATP2A1, ATP2A2, or ATP2A3) in the immune cell; and c) comparing SERCA pump expression in the immune cell to a reference, wherein increased expression of one or more SERCA pumps (e.g., the expression of one or more of ATP2A1, ATP2A2, or ATP2A3) in the immune cell as compared to the reference indicates that the subject has SERCA pump-associated cancer.

In some embodiments of any of the above aspects, the method further includes providing a SERCA pump inhibitor suitable for administration to the subject.

In some embodiments of any of the above aspects, the method further includes administering to the subject an effective amount of SERCA pump inhibitor.

In some embodiments of any of the above aspects, the SERCA pump inhibitor is a SERCA pump-specific inhibitor (e.g., an ATP2A1-specific inhibitor, an ATP2A2-specific inhibitor, or an ATP2A3-specific inhibitor).

In some embodiments of any of the above aspects, the SERCA pump inhibitor or SERCA pump-specific inhibitor is a SERCA pump function blocker.

In some embodiments of any of the above aspects, the SERCA pump inhibitor or SERCA pump-specific inhibitor decreases SERCA pump expression (e.g., the expression of one or more of ATP2A1, ATP2A2, or ATP2A3) or activity.

In some embodiments of any of the above aspects, the SERCA pump inhibitor or SERCA pump-specific inhibitor is a SERCA pump inhibitory antibody or an antigen binding fragment thereof.

In some embodiments of any of the above aspects, the SERCA pump inhibitory antibody is a SERCA pump-specific inhibitory antibody or an antigen binding fragment thereof (e.g., an ATP2A1-specific inhibitory antibody or an antigen binding fragment thereof, an ATP2A2-specific inhibitory antibody or an antigen binding fragment thereof, or an ATP2A3-specific inhibitory antibody or an antigen binding fragment thereof). In some embodiments of any of the above aspects, the SERCA pump inhibitory antibody binds to a SERCA pump binding partner listed in Table 1.

In some embodiments of any of the above aspects, the SERCA pump inhibitor or SERCA pump-specific inhibitor is an inhibitory RNA (e.g., short hairpin RNA (shRNA), small interfering RNA (siRNA), or microRNA (miRNA)) directed to a SERCA pump (e.g., ATP2A1, ATP2A2, or ATP2A3). In some embodiments of any of the above aspects, the SERCA pump inhibitor or SERCA pump-specific inhibitor is an inhibitory RNA directed to a SERCA pump binding partner listed in Table 1 (e.g., phospholamban (PLN), sarcolipin (SLN), or calsequestrin (CASQ2)).

In some embodiments of any of the above aspects, the SERCA pump inhibitor or SERCA pump-specific inhibitor is a nuclease (e.g., a CRISPR associated protein (Cas, e.g., Cas9), a transcription activator-like effector nuclease (TALEN), or a zinc finger nuclease (ZFN)) directed to a SERCA pump (e.g., ATP2A1, ATP2A2, or ATP2A3). In some embodiments of any of the above aspects, the SERCA pump inhibitor or SERCA pump-specific inhibitor is a nuclease (e.g., a Cas (e.g., Cas9), a TALEN, or a ZFN) directed to a SERCA pump binding partner listed in Table 1 (e.g., PLN, SLN, or CASQ2).

In some embodiments of any of the above aspects, the SERCA pump inhibitor or SERCA pump-specific inhibitor is a SERCA pump small molecule inhibitor listed in Table 2 (e.g., an inhibitor of ATP2A1, ATP2A2, or ATP2A3). In some embodiments, the SERCA pump small molecule inhibitor is BDBM50165366, BDBM50165367, BDBM50165368, or BDBM50165369.

In some embodiments of any of the above aspects, the cancer is a solid tumor (e.g., Melanoma, small cell lung cancer, non-small cell lung cancer, gastric cancer, colorectal cancer, head and neck cancer, ovarian cancer, kidney cancer, prostate cancer, breast cancer, hepatocellular carcinoma, or pancreatic cancer), an immune cell-infiltrated tumor or cancer (e.g., a T cell-infiltrated tumor or cancer), a cancer that is treated with immunotherapy (e.g., melanoma, non-small cell lung cancer, kidney cancer, renal cell carcinoma, bladder cancer, head and neck cancer, Hodgkin's lymphoma, leukemia, urothelial carcinoma, gastric cancer, microsatellite instability-high cancer, colorectal cancer, or hepatocellular carcinoma), or a cancer that does not respond to immunotherapy (e.g., a cancer that does not respond to immunotherapy or a cancer that did not respond to prior treatment with immunotherapy, e.g., a cancer for which immunotherapy is not effective).

In some embodiments of any of the above aspects, the immune cell-infiltrated tumor or cancer is a hot tumor (e.g., a tumor that that contains T cells and expresses neoantigens). In some embodiments, the hot tumor is a bladder cancer, head and neck cancer, kidney cancer, liver cancer, melanoma, non-small cell lung cancer, or microsatellite instability high cancer. In some embodiments of any of the above aspects, the immune cell-infiltrated tumor or cancer is a cold tumor (e.g., a tumor or cancer associated with suppressive immune cells, such as myeloid-derived suppressor cells and/or Tregs). In some embodiments, the cold tumor or cancer is a cancer or tumor that does not respond to immunotherapy. In some embodiments, the cold tumor or cancer is ovarian cancer, prostate cancer, or pancreatic cancer. In some embodiments of any of the above aspects, the tumor or cancer in the subject is identified as an immune cell-infiltrated tumor or cancer by evaluating a tumor or cancer sample isolated from the subject (e.g., a biopsy) for expression of an immune cell marker (e.g., one or more markers listed in Table 3).

In some embodiments of any of the above aspects, the SERCA pump inhibitor or SERCA pump-specific inhibitor is administered locally. In some embodiments of any of the above aspects, the SERCA pump inhibitor or SERCA pump-specific inhibitor is administered intratumorally, into a lymphoid organ, into a site of metastasis, into a tumor microenvironment, into a lymph node, or into the spleen. In some embodiments, the SERCA pump inhibitor or SERCA pump-specific inhibitor is administered intratumorally. In some embodiments, the SERCA pump inhibitor or SERCA pump-specific inhibitor is administered to a tumor microenvironment. In some embodiments, SERCA pump inhibitor or SERCA pump-specific inhibitor is administered to a site of metastasis. In some embodiments, the SERCA pump inhibitor or SERCA pump-specific inhibitor is administered to a lymph node. In some embodiments, the SERCA pump inhibitor or SERCA pump-specific inhibitor is administered to a lymphoid organ. In some embodiments, the SERCA pump inhibitor or SERCA pump-specific inhibitor is administered to the spleen. In some embodiments, the lymphoid organ is a secondary or tertiary lymphoid organ.

In some embodiments of any of the above aspects, the method further includes the step of administering a second therapeutic agent.

In some embodiments of any of the above aspects, the SERCA pump inhibitor or SERCA pump-specific inhibitor decreases tumor volume, decreases tumor growth, decreases tumor innervation, decreases tumor proliferation, decreases tumor metastasis, decreases tumor invasion, decreases tumor migration, increases time to recurrence, increases tumor or cancer cell death, increases tumor autophagy, decreases immune cell SERCA pump expression (e.g., the expression of one or more of ATP2A1, ATP2A2, or ATP2A3), increases immune cell proliferation, increases immune cell differentiation, increases immune cell migration, increases immune cell recruitment, increases immune cell tumor homing, increases immune cell polarization, increases immune cell activation, increases immune cell cytokine production (e.g., pro-inflammatory cytokine production), or improves survival.

In some embodiments of any of the above aspects, the method further includes measuring one or more of tumor volume, tumor growth, tumor innervation, tumor or cancer cell proliferation, tumor or cancer cell metastasis, tumor invasion, tumor or cancer cell migration, tumor or cancer cell death, tumor or cancer cell autophagy, immune cell migration, immune cell proliferation, immune cell recruitment, immune cell differentiation, immune cell activation, immune cell cytokine production, immune cell degranulation, immune cell ADCC, immune cell ADCP, or immune cell SERCA pump expression (e.g., the expression of one or more of ATP2A1, ATP2A2, or ATP2A3) before administration of the SERCA pump inhibitor or SERCA pump-specific inhibitor.

In some embodiments of any of the above aspects, the method further includes measuring one or more of tumor volume, tumor growth, tumor innervation, tumor or cancer cell proliferation, tumor or cancer cell metastasis, tumor invasion, tumor or cancer cell migration, tumor or cancer cell death, tumor autophagy, immune cell migration, immune cell proliferation, immune cell recruitment, immune cell differentiation, immune cell activation, immune cell cytokine production, immune cell degranulation, immune cell ADCC, immune cell ADCP, or immune cell SERCA pump expression (e.g., the expression of one or more of ATP2A1, ATP2A2, or ATP2A3) after administration of the SERCA pump inhibitor or SERCA pump-specific inhibitor.

In some embodiments of any of the above aspects, the SERCA pump inhibitor or SERCA pump-specific inhibitor is administered in an amount sufficient to treat the cancer or tumor, cause remission, increases time to recurrence, improve survival, decrease tumor volume, decrease tumor growth, decrease tumor innervation, decrease tumor or cancer cell proliferation, decrease tumor or cancer cell metastasis, decrease tumor or cancer cell invasion, increase tumor or cancer cell death, increase tumor autophagy, decrease tumor or cancer cell migration, increase immune cell proliferation, increase immune cell differentiation, increase immune cell activation, increase immune cell cytokine production (e.g., pro-inflammatory cytokine production), increase immune cell migration, increase immune cell recruitment, increase immune cell tumor homing, increase immune cell polarization, decrease immune cell SERCA pump expression (e.g., the expression of one or more of ATP2A1, ATP2A2, or ATP2A3), increase time to recurrence, or improve survival.

In some embodiments of any of the above aspects, the method further includes monitoring tumor or cancer progression (e.g., monitoring one or more of tumor volume, tumor or cancer cell growth, tumor innervation, tumor number, cancer cell proliferation, cancer cell invasion, cancer cell metastasis, cancer cell death, cancer cell autophagy, the development of HEVs or TLOs, immune cell migration, immune cell proliferation, immune cell recruitment, immune cell lymph node homing, immune cell lymph node egress, immune cell tumor homing, immune cell tumor egress, immune cell differentiation, immune cell activation, immune cell polarization, immune cell cytokine production, immune cell degranulation, immune cell maturation, immune cell ADCC, immune cell ADCP, immune cell antigen presentation, inflammation, or immune cell SERCA pump expression (e.g., the expression of one or more of ATP2A1, ATP2A2, or ATP2A3)) after administration of the SERCA pump inhibitor or SERCA pump-specific inhibitor.

In some embodiments of any of the above aspects, the cytokine is IFNγ.

In some embodiments of any of the above aspects, the immune cell is an effector T cell, helper T cell, cytotoxic T cell (e.g., CD8+ T cell), Th1 cell, Th2 cell, or Th17 cell.

In some embodiments of any of the above aspects, the subject is a human.

In another aspect, the invention provides an anti-cancer therapy including a SERCA pump inhibitor and a second agent selected from the group consisting of checkpoint inhibitors, chemotherapeutic agents, biologic cancer agents (e.g., an agent listed in Table 6), cancer-specific agents (e.g., an agent listed in Table 7), anti-angiogenic drugs, drugs that target cancer metabolism, antibodies that mark a cancer cell surface for destruction, antibody-drug conjugates, cell therapies, commonly used anti-neoplastic agents, non-drug therapies, chimeric antigen receptor (CAR)-T therapy, neurotransmission modulators, and neuronal growth factor modulators.

In some embodiments of any of the above aspects, the SERCA pump inhibitor is a SERCA pump function blocker.

In another aspect, the invention provides a pharmaceutical composition including a SERCA pump inhibitor.

In some embodiments of any of the above aspects, the SERCA pump inhibitor is a SERCA pump inhibitory antibody or an antigen binding fragment thereof.

In some embodiments of any of the above aspects, the SERCA pump inhibitory antibody is a SERCA pump-specific inhibitory antibody or an antigen binding fragment thereof (e.g., an ATP2A1-specific inhibitory antibody or an antigen binding fragment thereof, an ATP2A2-specific inhibitory antibody or an antigen binding fragment thereof, or an ATP2A3-specific inhibitory antibody or an antigen binding fragment thereof). In some embodiments of any of the above aspects, the SERCA pump inhibitory antibody binds to a SERCA pump binding partner listed in Table 1 (e.g., PLN, SLN, or CASQ2).

In some embodiments of any of the above aspects, the SERCA pump inhibitor or SERCA pump-specific inhibitor is an inhibitory RNA (e.g., shRNA, siRNA, or miRNA) directed to a SERCA pump (e.g., ATP2A1, ATP2A2, or ATP2A3). In some embodiments of any of the above aspects, the SERCA pump inhibitor or SERCA pump-specific inhibitor is an inhibitory RNA (e.g., shRNA, siRNA, or miRNA) directed to a SERCA pump binding partner listed in Table 1 (e.g., PLN, SLN, or CASQ2).

In some embodiments of any of the above aspects, the SERCA pump inhibitor or SERCA pump-specific inhibitor is a nuclease (e.g., a Cas (e.g., Cas9), a TALEN, or a ZFN) directed to a SERCA pump (e.g., ATP2A1, ATP2A2, or ATP2A3). In some embodiments of any of the above aspects, the SERCA pump inhibitor or SERCA pump-specific inhibitor is a nuclease (e.g., a Cas (e.g., Cas9), a TALEN, or a ZFN) directed to a SERCA pump binding partner listed in Table 1 (e.g., PLN, SLN, or CASQ2).

In some embodiments of any of the above aspects, the SERCA pump inhibitor or SERCA pump-specific inhibitor is a SERCA pump small molecule inhibitor listed in Table 2 (e.g., an inhibitor of ATP2A1, ATP2A2, or ATP2A3). In some embodiments, the SERCA pump small molecule inhibitor is BDBM50165366, BDBM50165367, BDBM50165368, or BDBM50165369.

In some embodiments of any of the above aspects, the SERCA pump-specific inhibitory antibody (e.g., ATP2A1-specific inhibitory antibody, ATP2A2-specific inhibitory antibody, or ATP2A3-specific inhibitory antibody) exhibits one or more of the following activities: (a) disrupts calcium transport; or (b) antagonizes the SERCA pump. In some embodiments, the SERCA pump-specific inhibitory antibody is an ATP2A2 specific inhibitory antibody that binds to residue P602 of ATP2A2.

In some embodiments of any of the above aspects, the composition further includes a second therapeutic agent.

In some embodiments of any of the above aspects, the composition further includes a pharmaceutically acceptable excipient.

In some embodiments of any of the above aspects, the second therapeutic agent is an anti-cancer therapeutic, a SERCA pump function blocker, a neurotransmission modulator, or a neuronal growth factor modulator.

In some embodiments of any of the above aspects, the anti-cancer therapeutic is a checkpoint inhibitor, a chemotherapeutic agent, a biologic cancer agent (e.g., an agent listed in Table 6), a cancer-specific agent (e.g., an agent listed in Table 7), an anti-angiogenic drug, a drug that targets cancer metabolism, an antibody that marks a cancer cell surface for destruction, an antibody-drug conjugate, a cell therapy, a commonly used anti-neoplastic agent, CAR-T therapy, an anti-cancer vaccine, or a non-drug therapy.

In some embodiments of any of the above aspects, the checkpoint inhibitor is an inhibitory antibody, a fusion protein, an agent that interacts with a checkpoint protein, an agent that interacts with the ligand of a checkpoint protein, an inhibitor of CTLA-4, an inhibitor of PD-1, an inhibitor of PDL1, an inhibitor of PDL2, or an inhibitor of B7-H3, B7-H4, BTLA, HVEM, TIM3, GAL9, LAGS, VISTA, KIR, 2B4, CD160, CGEN-15049, CHK 1, CHK2, A2aR, or B-7 family ligands.

In some embodiments of any of the above aspects, the biologic cancer agent is an antibody listed in Table 6.

In some embodiments of any of the above aspects, the cancer is a cancer listed in column 1 of Table 7 and the second agent is a corresponding anti-cancer agent listed in column 2 of Table 7.

In some embodiments of any of the above aspects, the neurotransmission modulator is neurotoxin listed in Table 12, or a modulator (e.g., agonist or antagonist) of a neurotransmitter receptor listed in Table 8 or a neurotransmitter listed in Table 9. In some embodiments, the modulator of a neurotransmitter receptor listed in Table 8 or a neurotransmitter listed in Table 9 is an agonist or antagonist listed in Tables 10A-10K or a modulator listed in Table 11.

In some embodiments of any of the above aspects, the neuronal growth factor modulator is an agonist or an antagonist of a neuronal growth factor listed in Table 13. In some embodiments, the agonist or antagonist of a neuronal growth factor listed in Table 13 is an antibody listed in Table 14 or an agonist or antagonist listed in Table 15. In some embodiments, the antagonist of a neuronal growth factor listed in Table 13 is selected from the group consisting of etanercept, thalidomide, lenalidomide, pomalidomide, pentoxifylline, bupropion, DOI, disitertide, and trabedersen.

In some embodiments of any of the above aspects, the cancer is a solid tumor (e.g., melanoma, small cell lung cancer, non-small cell lung cancer, gastric cancer, colorectal cancer, head and neck cancer, ovarian cancer, kidney cancer, prostate cancer, breast cancer, hepatocellular carcinoma, or pancreatic cancer), an immune cell-infiltrated cancer or tumor (e.g., a T cell-infiltrated cancer or tumor), a cancer that is treated with immunotherapy (e.g., melanoma, non-small cell lung cancer, kidney cancer, renal cell carcinoma, bladder cancer, head and neck cancer, Hodgkin's lymphoma, leukemia, urothelial carcinoma, gastric cancer, microsatellite instability-high cancer, colorectal cancer, or hepatocellular carcinoma), or a cancer that does not respond to immunotherapy (e.g., a cancer that does not respond to immunotherapy or a cancer that did not respond to prior treatment with immunotherapy, e.g., a cancer for which immunotherapy is not effective). In some embodiments of any of the above aspects, the cancer is a SERCA pump-associated cancer.

In some embodiments of any of the above aspects, the SERCA pump function blocker is a SERCA pump inhibitory antibody or an antigen binding fragment thereof. In some embodiments, the SERCA pump inhibitory antibody is a SERCA pump-specific inhibitory antibody or an antigen binding fragment thereof (e.g., an ATP2A1-specific inhibitory antibody, an ATP2A2-specific inhibitory antibody, or an ATP2A3-specific inhibitory antibody). In some embodiments, the SERCA pump inhibitory antibody binds to a SERCA pump binding partner listed in Table 1. In some embodiments of any of the above aspects, the SERCA pump function blocker is an inhibitory RNA directed to a SERCA pump or a SERCA pump binding partner listed in Table 1. In some embodiments of any of the above aspects, the SERCA pump function blocker is a nuclease (e.g., a Cas (e.g., Cas9), TALEN, or ZFN) directed to a SERCA pump or a SERCA pump binding partner listed in Table 1. In some embodiments of any of the above aspects, the SERCA pump function blocker is a SERCA pump small molecule inhibitor listed in Table 2. In some embodiments, the SERCA pump small molecule inhibitor is BDBM50165366, BDBM50165367, BDBM50165368, or BDBM50165369.

In some embodiments of any of the above aspects, the SERCA pump inhibitor or SERCA pump-specific inhibitor is selected from the group consisting of an antibody, a polypeptide, a DNA molecule, an RNA molecule, a nuclease, a small molecule, and a viral vector. In some embodiments, the antibody is a SERCA pump inhibitory antibody or an antigen binding fragment thereof. In some embodiments, the SERCA pump inhibitory antibody is a SERCA pump-specific inhibitory antibody or an antigen binding fragment thereof (e.g., an ATP2A1-specific inhibitory antibody, an ATP2A2-specific inhibitory antibody, or an ATP2A3-specific inhibitory antibody). In some embodiments, the SERCA pump inhibitory antibody binds to a SERCA pump binding partner listed in Table 1. In some embodiments, the RNA is an inhibitory RNA directed to a SERCA pump or a SERCA pump binding partner listed in Table 1. In some embodiments, the nuclease (e.g., a Cas (e.g., Cas9), TALEN, or ZFN) is directed to a SERCA pump or a SERCA pump binding partner listed in Table 1. In some embodiments, the small molecule is a SERCA pump small molecule inhibitor listed in Table 2. In some embodiments, the SERCA pump small molecule inhibitor is a BDBM50165366, BDBM50165367, BDBM50165368, or BDBM50165369.

In some embodiments of any of the above aspects, the small molecule SERCA pump inhibitor listed in Table 2 is a non-selective SERCA pump inhibitor.

In some embodiments of any of the above aspects, the small molecule SERCA pump inhibitor listed in Table 2 is an ATP2A1 inhibitor.

In some embodiments of any of the above aspects, the small molecule SERCA pump inhibitor listed in Table 2 is an ATP2A2 inhibitor.

In some embodiments of any of the above aspects, the SERCA pump inhibitor or SERCA pump-specific inhibitor does not cross the blood brain barrier. In some embodiments, the SERCA pump inhibitor or SERCA pump-specific inhibitor has been modified to prevent blood brain barrier crossing by conjugation to a targeting moiety, formulation in a particulate delivery system, addition of a molecular adduct, or through modulation of its size, polarity, flexibility, or lipophilicity.

In some embodiments of any of the above aspects, the SERCA pump inhibitor or SERCA pump-specific inhibitor does not have a direct effect on the central nervous system or gut.

In some embodiments of any of the above aspects, the SERCA pump inhibitor or SERCA pump-specific inhibitor decreases tumor volume, decreases tumor growth, decreases tumor innervation, decreases tumor proliferation, decreases tumor metastasis, decreases tumor invasion, decreases tumor migration, increases time to recurrence, increases tumor or cancer cell death, increases tumor autophagy, decreases immune cell SERCA pump expression (e.g., expression of one or more of ATP2A1, ATP2A2, or ATP2A3), increases immune cell proliferation, increases immune cell differentiation, increases immune cell activation, increases immune cell cytokine production, increases time to recurrence, or improves survival.

In some embodiments of any of the above aspects, the immune cell is an effector T cell, a helper T cell, a cytotoxic T cell (e.g., a CD8+ T cell), aTh1 cell, a Th2 cell, a Th17 cell, a B cell, a natural killer (NK) cell, an innate lymphoid cell 1 (ILC1) cell, an ILC2 cell, an ILC3 cell, a monocyte, a macrophage (e.g., an M1 or M2 macrophage), a dendritic cell, a neutrophil, a basophil, an eosinophil, or an antigen presenting cell.

In some embodiments of any of the above aspects, the immune cell is a T cell (e.g., an effector T cell, a helper T cell, a cytotoxic T cell (e.g., a CD8+ T cell), a Th1 cell, a Th2 cell, or a Th17 cell). In some embodiments of any of the above aspects, the method decreases T cell SERCA pump expression (e.g., expression of one or more of ATP2A1, ATP2A2, or ATP2A3), increases T cell proliferation, increases T cell differentiation, increases T cell activation, or increases T cell cytokine production (e.g., pro-inflammatory cytokine production). In some embodiments of any of the above aspects, the cytokine is IFNγ.

In some embodiments of any of the above aspects, the SERCA pump is ATP2A2, ATP2A3, or ATP2A1.

Definitions

As used herein, "administration" refers to providing or giving a subject a therapeutic agent (e.g., a SERCA pump inhibitor), by any effective route. Exemplary routes of administration are described herein below.

As used herein, the term "agonist" refers to an agent (e.g., a small molecule or antibody) that increases receptor activity. An agonist may activate a receptor by directly binding to the receptor, by acting as a cofactor, by modulating receptor conformation (e.g., maintaining a receptor in an open or active state). An agonist may increase receptor activity by 10%, 20%, 30%, 40%, 50%, 60%, 70%, 80%, 90%, 95%, 98% or more. An agonist may induce maximal receptor activation or partial activation depending on the concentration of the agonist and its mechanism of action.

As used herein, the term "analog" refers to a protein of similar nucleotide or amino acid composition or sequence to any of the proteins or peptides of the invention, allowing for variations that do not have an adverse effect on the ability of the protein or peptide to carry out its normal function (e.g., bind to a receptor or promote synapse formation). Analogs may be the same length, shorter, or longer than their corresponding protein or polypeptide. Analogs may have about 60% (e.g., about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, or about 99%) identity to the amino acid sequence of the naturally occurring protein or peptide. An analog can be a naturally occurring protein or polypeptide sequence that is modified by deletion, addition, mutation, or substitution of one or more amino acid residues.

As used herein, the term "antagonist" refers to an agent (e.g., a small molecule or antibody) that reduces or inhibits receptor activity. An antagonist may reduce receptor activity by directly binding to the receptor, by blocking the receptor binding site, by modulating receptor conformation (e.g., maintaining a receptor in a closed or inactive state). An antagonist may reduce receptor activity by 10%, 20%, 30%, 40%, 50%, 60%, 70%, 80%, 90%, 95%, 98% or more. An antagonist may also completely block or inhibit receptor activity. Antagonist activity may be concentration-dependent or -independent.

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab')2, Fd, Fvs, single-chain Fvs (scFv), rIgG, single-chain antibodies, disulfide-linked Fvs (sdFv), fragments containing either a VL or VH domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and F(ab')2 fragments) that are capable of specifically binding to a target protein. Fab and F(ab')2 fragments lack the Fc fragment of an intact antibody.

The term "antigen-binding fragment," as used herein, refers to one or more fragments of an immunoglobulin that retain the ability to specifically bind to a target antigen. The antigen-binding function of an immunoglobulin can be performed by fragments of a full-length antibody. The antibody fragments can be a Fab, F(ab')2, scFv, SMIP, diabody, a triabody, an affibody, a nanobody, an aptamer, or a domain antibody. Examples of binding fragments encompassed by the term "antigen-binding fragment" of an antibody include, but are not limited to: (i) a Fab fragment, a monovalent fragment consisting of the VL, VH, CL, and CH1 domains; (ii) a F(ab')$_2$ fragment, a bivalent fragment containing two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb (Ward et al., Nature 341:544-546, 1989) including VH and VL domains; (vi) a dAb fragment that consists of a VH domain; (vii) a dAb that consists of a VH or a VL domain; (viii) an isolated complementarity determining region (CDR); and (ix) a combination of two or more isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv)). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "binding partner" refers to a polypeptide or fragment thereof that binds to a protein of interest (e.g., a SERCA pump). Binding partners include receptors and other molecules that selectively bind to the ligand of interest. Exemplary SERCA pump binding partners include phospholamban (PLN), sarcolipin (SLN), and calsequestrin (CASQ2).

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the terms "effective amount," "therapeutically effective amount," and a "sufficient amount" of a composition, antibody, vector construct, viral vector, or cell described herein refer to a quantity sufficient to, when administered to a subject, including a mammal (e.g., a human), effect beneficial or desired results, including effects at the cellular level, tissue level, or clinical results, and, as such, an "effective amount" or synonym thereto depends upon the context in which it is being applied. For example, in the context of treating cancer it is an amount of the composition, antibody, vector construct, viral vector, or cell sufficient to achieve a treatment response as compared to the response obtained without administration of the composition, antibody, vector construct, viral vector, or cell. The amount of a given composition described herein that will correspond to such an amount will vary depending upon various factors, such as the given agent, the pharmaceutical formulation, the route of administration, the type of disease or disorder, the identity of the subject (e.g., age, sex, weight) or host being treated, and the like, but can nevertheless be routinely determined by one skilled in the art. Also, as used herein, a "therapeutically effective amount" of a composition, antibody, vector construct, viral vector or cell of the present disclosure is an amount that results in a beneficial or desired result in a subject as compared to a control. As defined herein, a therapeutically effective amount of a composition, antibody, vector construct, viral vector, or cell of the present disclosure may be readily determined by one of ordinary skill by routine methods known in the art. Dosage regimen may be adjusted to provide the optimum therapeutic response.

As used herein, the terms "increasing" and "decreasing" refer to modulating resulting in, respectively, greater or lesser amounts, of function, expression, or activity of a metric relative to a reference. For example, subsequent to administration of a SERCA pump inhibitor in a method described herein, the amount of a marker of a metric (e.g., immune cell activation) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "innervated" refers to a tissue (e.g., a tumor) that contains nerves. "Innervation" refers to the process of nerves entering a tissue.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect.

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof and which is indicated for human use.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "proliferation" refers to an increase in cell numbers through growth and division of cells.

As used herein, the term "reference" refers to a level, expression level, copy number, sample or standard that is used for comparison purposes. For example, a reference sample can be obtained from a healthy individual (e.g., an individual who does not have cancer). A reference level can be the level of expression of one or more reference samples. For example, an average expression (e.g., a mean expression or median expression) among a plurality of individuals (e.g., healthy individuals, or individuals who do not have cancer). In other instances, a reference level can be a predetermined threshold level, e.g., based on functional expression as otherwise determined, e.g., by empirical assays.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the terms "subject" and "patient" refer to an animal (e.g., a mammal, such as a human). A subject to be treated according to the methods described herein may be one who has been diagnosed with a particular condition, or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

"Treatment" and "treating," as used herein, refer to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

As used herein, the term "overexpressed" refers to a nucleic acid or polypeptide that is expressed or caused to be expressed or produced in a cell at a greater level than is normally expressed in the corresponding wild-type cell. For example, a SERCA pump is "overexpressed" in an immune cell (e.g., an effector T cell, a helper T cell, a cytotoxic T cell, a Th1 cell, a Th2 cell, or a Th17 cell) when one or more SERCA pumps (e.g., ATP2A1, ATP2A2, or ATP2A3) is present at a higher level in the immune cell (e.g., an effector T cell, a helper T cell, a Th1 cell, a Th2 cell, or a Th17 cell) compared to the level in a healthy cell of the same tissue or cell type from the same species or individual. A SERCA pump is overexpressed when the expression of one or more SERCA pumps is increased by 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) compared to a reference (e.g., a healthy cell of the same type).

As used herein, the term "cancer" refers to a condition characterized by unregulated or abnormal cell growth. The terms "cancer cell," "tumor cell," and "tumor" refer to an abnormal cell, mass, or population of cells that result from excessive division that may be malignant or benign and all pre-cancerous and cancerous cells and tissues.

As used herein, the term "SERCA pump-associated cancer" refers to a cancer that is associated with immune cells in which a SERCA pump is expressed (e.g., immune cells that express one or more SERCA pumps (e.g., ATP2A1, ATP2A2, or ATP2A3) or immune cells having increased expression of one or more SERCA pumps (e.g., ATP2A1, ATP2A2, or ATP2A3)) compared to a reference (e.g., an immune cell from a subject that does not have cancer). The immune cells can be systemic immune cells (e.g., effector T cells, helper T cells, cytotoxic T cells (e.g., CD8+ T cells), Th1 cells, Th2 cells, or Th17 cells) or immune cells that have infiltrated the tumor (e.g., infiltrating T cells). SERCA pump-associated cancers can be identified by assessing an immune cell or a biopsy of an immune-cell infiltrated tumor for immune cell SERCA pump expression (e.g., gene or protein expression) and comparing it to SERCA pump expression in a reference cell.

As used herein, the term "activation" refers to the response of an immune cell to a perceived insult. When immune cells become activated, they proliferate, secrete pro-inflammatory cytokines, differentiate, present antigens, become more polarized, and become more phagocytic and cytotoxic. Factors that stimulate immune cell activation include pro-inflammatory cytokines, pathogens, and non-self antigen presentation (e.g., antigens from pathogens presented by dendritic cells, macrophages, or B cells).

As used herein, the terms "antibody-dependent cell mediated cytotoxicity" and "antibody-dependent cellular toxicity" (ADCC) refer to the killing of an antibody-coated target cell by a cytotoxic effector cell through a non-phagocytic process, characterized by the release of the content of cytotoxic granules or by the expression of cell death-inducing molecules. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, innate lymphoid cells (ILCs), monocytes, macrophages, neutrophils, eosinophils and dendritic cells.

As used herein, the terms "antibody-dependent cell mediated phagocytosis" and "antibody-dependent cellular phagocytosis" (ADCP) refer to the phagocytosis (e.g., engulfment) of an antibody-coated target cell by immune cells (e.g., phagocytes). ADCP is triggered through interaction of target-bound antibodies (belonging to IgG or IgA or IgE classes) with certain Fc receptors (FcRs, e.g., FcγRIIa, FcγRIIIa, and FcγRI), glycoproteins present on the effector cell surface that bind the Fc region of immunoglobulins (Ig). Effector cells that mediate ADCP include monocytes, macrophages, neutrophils, and dendritic cells.

As used herein, the term "antigen presentation" refers to a process in which fragments of antigens are displayed on the cell surface of immune cells. Antigens are presented to T cells and B cells to stimulate an immune response. Antigen presenting cells include dendritic cells, B cells, and macrophages. Mast cells and neutrophils can also be induced to present antigens.

As used herein, the term "anti-inflammatory cytokine" refers to a cytokine produced or secreted by an immune cell that reduces inflammation. Immune cells that produce and secrete anti-inflammatory cytokines include T cells (e.g., Th cells) macrophages, B cells, and mast cells. Anti-inflammatory cytokines include IL4, IL-10, IL-11, IL-13, interferon alpha (IFNα) and transforming growth factor-beta (TGFβ).

As used herein, the term "chemokine" refers to a type of small cytokine that can induce directed chemotaxis in nearby cells. Classes of chemokines include CC chemokines, CXC chemokines, C chemokines, and CX3C chemokines. Chemokines can regulate immune cell migration and homing, including the migration and homing of monocytes, macrophages, T cells, mast cells, eosinophils, and neutrophils. Chemokines responsible for immune cell migration include CCL19, CCL21, CCL14, CCL20, CCL25, CCL27, CXCL12, CXCL13, CCR9, CCR10, and CXCR5. Chemokines that can direct the migration of inflammatory leukocytes to sites of inflammation or injury include CCL2, CCL3, CCL5, CXCL1, CXCL2, and CXCL8.

As used herein, the term "cytokine" refers to a small protein involved in cell signaling. Cytokines can be produced and secreted by immune cells, such as T cells, B cells, macrophages, and mast cells, and include chemokines, interferons, interleukins, lymphokines, and tumor necrosis factors.

As used herein, the term "cytokine production" refers to the expression, synthesis, and secretion (e.g., release) of cytokines by an immune cell.

As used herein, the term "cytotoxicity" refers to the ability of immune cells to kill other cells. Immune cells with cytotoxic functions release toxic proteins (e.g., perforin and granzymes) capable of killing nearby cells. Natural killer cells, ILCs, and cytotoxic T cells (e.g., CD8+ T cells) are the primary cytotoxic effector cells of the immune system, although dendritic cells, neutrophils, eosinophils, mast cells, basophils, macrophages, and monocytes have been shown to have cytotoxic activity.

As used herein, the term "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, immune cell, or endothelial cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). By "committed" or "differentiated" is meant a cell that expresses one or more markers or other characteristic of a cell of a particular lineage.

As used herein, the term "degranulation" refers to a cellular process in which molecules, including antimicrobial and cytotoxic molecules, are released from intracellular secretory vesicles called granules. Degranulation is part of the immune response to pathogens and invading microorganisms by immune cells such as granulocytes (e.g., neutrophils, basophils, and eosinophils), mast cells, and lymphocytes (e.g., natural killer cells, ILCs, and cytotoxic T cells). The molecules released during degranulation vary by cell type and can include molecules designed to kill the invading pathogens and microorganisms or to promote an immune response, such as inflammation.

As used herein, the term "immune dysregulation" refers to a condition in which the immune system is disrupted or responding to an insult. Immune dysregulation includes aberrant activation (e.g., autoimmune disease) and activation in response to an injury or disease (e.g., disease-associated inflammation). Immune dysregulation also includes under-activation of the immune system (e.g., failure to mount an immune response to cancer cells or immunosuppression). Immune dysregulation can be treated using the methods and compositions described herein to direct immune cells to carry out beneficial functions and reduce harmful activities (e.g., promoting activation and cytotoxicity in subjects with cancer and reducing activation and pro-inflammatory cytokine secretion in subjects with autoimmune disease).

As used herein, the term "modulating an immune response" refers to any alteration in a cell of the immune system or any alteration in the activity of a cell involved in the immune response. Such regulation or modulation includes an increase or decrease in the number of various cell types, an increase or decrease in the activity of these cells, or any other changes that can occur within the immune system. Cells involved in the immune response include, but are not limited to, T lymphocytes (T cells), B lymphocytes (B cells), natural killer (NK) cells, ILCs, macrophages, eosinophils, mast cells, dendritic cells and neutrophils. In some cases, "modulating" the immune response means the immune response is stimulated or enhanced, and in other cases "modulating" the immune response means suppression of the immune system.

As used herein, the term "lymph node egress" refers to immune cell exit from the lymph nodes, which occurs during immune cell recirculation. Immune cells that undergo recirculation include lymphocytes (e.g., T cells, B cells, and natural killer cells), which enter the lymph node from blood to survey for antigen and then exit into lymph and return to the blood stream to perform antigen surveillance.

As used herein, the term "lymph node homing" refers to directed migration of immune cells to a lymph node. Immune cells that return to lymph nodes include T cells, B cells, macrophages, and dendritic cells.

As used herein, the term "migration" refers to the movement of immune cells throughout the body. Immune cells can migrate in response to external chemical and mechanical signals. Many immune cells circulate in blood including peripheral blood mononuclear cells (e.g., lymphocytes such as T cells, B cells, and natural killer cells), monocytes, macrophages, dendritic cells, and polymorphonuclear cells (e.g., neutrophils and eosinophils). Immune cells can migrate to sites of infection, injury, or inflammation, back to the lymph nodes, or to tumors or cancer cells.

As used herein, the term "phagocytosis" refers to the process in which a cell engulfs or ingests material, such as other cells or parts of cells (e.g., bacteria), particles, or dead or dying cells. A cell that capable of performing this function is called a phagocyte. Immune phagocytes include neutrophils, monocytes, macrophages, mast cells, B cells, eosinophils, and dendritic cells.

As used herein, the term "polarization" refers to the ability of an immune cell to shift between different functional states. A cell that is moving toward one of two functional extremes is said to be in the process of becoming more polarized. The term polarization is often used to refer to macrophages, which can shift between states known as M1 and M2. M1, or classically activated, macrophages secrete pro-inflammatory cytokines (e.g., IL-12, TNF, IL-6, IL-8, IL-1B, MCP-1, and CCL2), are highly phagocytic, and respond to pathogens and other environmental insults. M1 macrophages can also be detected by expression of Nos2. M2, or alternatively activated, macrophages secrete a different set of cytokines (e.g., IL-10) and are less phagocytic. M2 macrophages can detected by expression of Arg1, IDO, PF4, CCL24, IL10, and IL4Ra. Cells become polarized in response to external cues such as cytokines, pathogens, injury, and other signals in the tissue microenvironment.

As used herein, the term "pro-inflammatory cytokine" refers to a cytokine secreted from immune cells that promotes inflammation. Immune cells that produce and secrete pro-inflammatory cytokines include T cells (e.g., Th cells) macrophages, B cells, and mast cells. Pro-inflammatory cytokines include interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF).

As used herein, the term "pro-survival cytokine" refers to a cytokine that promotes the survival of immune cells (e.g., T cells). Pro-survival cytokines include IL-2, IL-4, IL-6, IL-7, and IL-15.

As used herein, the term "recruitment" refers to the re-distribution of immune cells to a particular location. Immune cells that can undergo this re-distribution and be recruited to sites of injury or disease include monocytes, macrophages, T cells, B cells, dendritic cells, and natural killer cells.

As used herein, the term "T cell" refers to a type of lymphocyte that plays a central role in cell-mediated immunity. T cells can be distinguished from other lymphocytes, such as B cells and natural killer cells, by the presence of a T-cell receptor (TCR) on the cell surface. There are several subsets of T cells, each having a distinct function (e.g., effector T cells, and memory T cells).

As used herein, the term "effector T cell" refers to a broad subset of T cells that actively responds to a stimulus, such as co-stimulation. The category of effector T cell includes helper T cell, killer T cell, and regulatory T cell.

As used herein, the term "helper T cell" (Th cells) refers to a subset of T cell that assists other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Th cells become activated when they are presented with peptide antigens by MHC class II molecules, which are expressed on the surface of antigen presenting cells (APCs). Once activated, they divide rapidly and secrete cytokines that regulate or assist in the active immune response. Th cells can differentiate into one of several subtypes (e.g., Th1, Th2, Th3, Th17, or TH9), which secrete different cytokines to facilitate different types of immune responses.

As used herein, the term "regulatory T cells" (Tregs) refers to a subpopulation of immunosuppressive T cells expressing the biomarkers CD4, FOXP3, and CD25. Tregs modulate the immune system, maintain tolerance to self-antigens, prevent autoimmune disease, and also suppress the anti-tumor immune response. Tregs are thought to suppress tumor immunity, thus hindering the body's innate ability to control the growth of cancerous cells. Tregs execute their immunosuppressive effects through IL-2/IL-2 receptor-dependent and CTLA-4-dependent mechanisms, and by production of inhibitory cytokines (e.g., IL-10 and TGF-beta).

The term "SERCA pump inhibitory antibody" refers to antibodies that are capable of binding to a SERCA pump or a SERCA pump binding partner (e.g., PLN) and inhibiting or reducing SERCA pump function, SERCA pump binding to a binding partner, SERCA pump expression, and/or attenuating one or more signal transduction pathways mediated by a SERCA pump. For example, SERCA pump inhibitory antibodies may bind to or block the ligand binding domains of a SERCA pump (e.g., the domains that bind to PLN to prevent or reduce binding). The term "SERCA pump-specific inhibitory antibody" refers to antibodies that bind specifically to a single SERCA pump (e.g., ATP2A1, ATP2A2, or ATP2A3) and reduce the activity of or attenuate one or more signal transduction pathways mediated by the SERCA pump. SERCA pump inhibitory antibodies and SERCA pump-specific inhibitory antibodies may inhibit or reduce binding of a SERCA pump to a binding partner, reduce SERCA pump function, and/or attenuate one or more SERCA pump-mediated signal transduction pathways by at least 10% (e.g., 10%, 20%, 30%, 40%, 50%, 60%, 70%, 80%, 90%, 95%, 98% or more).

As used herein, the term "SERCA pump inhibitor" refers to an agent that inhibits or reduces SERCA pump function, the binding of a SERCA pump to its binding partner, SERCA pump expression, or SERCA pump signaling. SERCA pump inhibitors include SERCA pump inhibitory antibodies or antigen binding fragments thereof, inhibitory RNAs or nucleases directed to SERCA pumps, SERCA pump small molecule inhibitors (e.g., SERCA pump small molecule antagonists listed in Table 2), or other agents that inhibit or reduce SERCA pump function, the binding of SERCA pump to a binding partner, SERCA pump expression, or signal transduction downstream of SERCA pump. SERCA pump inhibitors reduce SERCA pump binding, expression, function, or signaling by 10% or more (e.g., 10%, 20%, 30%, 40%, 50%, 60%, 70%, 80%, 90%, 95%, 98% or more).

As used herein, the term "SERCA pump-specific inhibitor" refers to a SERCA pump inhibitor that selectively binds to and inhibits or reduces the expression, function, or signaling of a single SERCA pump (e.g., ATP2A1, ATP2A2, or ATP2A3) without directly binding to and reducing the function or signaling of a related protein (e.g., without binding to and reducing the function or signaling of another SERCA pump). SERCA pump-specific inhibitors include SERCA pump-specific inhibitory antibodies (e.g., an ATP2A1-specific inhibitory antibody), inhibitory RNAs and nucleases directed to SERCA1 pumps, and SERCA pump-selective small molecule inhibitors. SERCA pump-specific inhibitors reduce the function or signaling of a single SERCA pump by 10% or more (e.g., 10%, 20%, 30%, 40%, 50%, 60%, 70%, 80%, 90%, 95%, 98% or more).

As used herein, the term "SERCA pump function blocker" refers to a type of SERCA pump inhibitor that reduces or inhibits SERCA pump function by reducing the expression or activity of SERCA pumps or preventing SERCA pumps from interacting with one or more of binding partners (e.g., PLN). Exemplary SERCA pump function blockers include antibodies that bind to a SERCA pump, inhibitory RNAs or nucleases directed to a SERCA pump, and SERCA pump small molecule antagonists. SERCA pump function blockers reduce SERCA pump function by 10% or more (e.g., 10%, 20%, 30%, 40%, 50%, 60%, 70%, 80%, 90%, 95%, 98% or more).

As used herein, the terms "SERCA pump small molecule inhibitor" and "SERCA pump small molecule antagonist" refer to a small molecule that reduces or inhibits function, activation, or signaling of a SERCA pump (e.g., one or more of ATP2A1, ATP2A2, or ATP2A3) and has an IC50 of 10 μM or lower. The SERCA pump antagonist may be selective for a single SERCA pump (e.g., primarily binds to and inhibits or reduces the function or activation of a single SERCA pump compared to other SERCA pumps), or the SERCA pump antagonist may exhibit similar inhibitory effects on multiple SERCA pumps (e.g., may bind to and reduce the function or activation of more than one SERCA pump). An antagonist binds to a SERCA pump to directly inhibit SERCA pump function or activity, while an inhibitor may affect SERCA pump function either directly or indirectly. SERCA pump inhibitors and antagonists for use in the methods and compositions described herein are provided in Table 2.

As used herein, an agent that "does not cross the blood brain barrier" is an agent that does not significantly cross the barrier between the peripheral circulation and the brain and spinal cord. This can also be referred to as a "blood brain barrier impermeable" agent. Agents will have a limited ability to cross the blood brain barrier if they are not lipid soluble or have a molecular weight of over 600 Daltons. Agents that typically cross the blood brain barrier can be modified to become blood brain barrier impermeable based on chemical modifications that increase the size or alter the hydrophobicity of the agent, packaging modifications that reduce diffusion (e.g., packaging an agent within a microparticle or nanoparticle), and conjugation to biologics that direct the agent away from the blood brain barrier (e.g., conjugation to a pancreas-specific antibody). An agent that does not cross the blood brain barrier is an agent for which 30% or less (e.g., 30%, 25%, 20%, 15%, 10%, 5%, 2% or less) of the administered agent crosses the blood brain barrier.

As used herein, an agent that "does not have a direct effect on the central nervous system (CNS) or gut" is an agent that does not directly alter neurotransmission, neuronal numbers, or neuronal morphology in the CNS or gut when administered according to the methods described herein. This may be assessed by administering the agents to animal models and performing electrophysiological recordings or immunohistochemical analysis. An agent will be considered not to have a direct effect on the CNS or gut if administration according to the methods described herein has an effect on neurotransmission, neuronal numbers, or neuronal morphology in the CNS or gut that is 50% or less (e.g., 50%, 45%, 40%, 35%, 30%, 25%, 20%, 15%, 10%, 5%, or less) of the effect observed if the same agent is administered directly to the CNS or gut.

As used herein, the term "neuronal growth factor modulator" refers to an agent that regulates neuronal growth, development, or survival. Neuronal growth factors include proteins that promote neurogenesis, neuronal growth, and neuronal differentiation (e.g., neurotrophic factors NGF, NT3, BDNF, CNTF, and GDNF), proteins that promote neurite outgrowth (e.g., axon or dendrite outgrowth or stabilization), or proteins that promote synapse formation (e.g., synaptogenesis, synapse assembly, synaptic adhesion, synaptic maturation, synaptic refinement, or synaptic stabilization). These processes lead to innervation of tissue, including neural tissue, muscle, lymph nodes and tumors, and the formation of synaptic connections between two or more neurons and between neurons and non-neural cells (e.g., tumor cells). A neuronal growth factor modulator may block one or more of these processes (e.g., through the use of antibodies that block neuronal growth factors or their receptors) or promote one or more of these processes (e.g., through the use of these proteins or analogs or peptide fragments thereof). Exemplary neuronal growth factors are listed in Table 13. Neuronal growth factor modulators decrease or increase neurite outgrowth, innervation, synapse formation, or any of the aforementioned processes by 10% or more (e.g., 10%, 20%, 30%, 40%, 50%, 60%, 70%, 80%, 90%, 95%, 98% or more).

As used herein, the term "neurotransmission modulator" refers to an agent that either induces or increases neurotransmission or decreases or blocks neurotransmission. Neurotransmission modulators can increase or decrease neurotransmission by 10%, 20%, 30%, 40%, 50%, 60%, 70%, 80%, 90%, 95%, 98% or more. Exemplary neurotransmitters and neurotransmitter receptors are listed in Tables 8 and 9. Neurotransmission modulators may increase neurotransmission by increasing neurotransmitter synthesis or release, preventing neurotransmitter reuptake or degradation, increasing neurotransmitter receptor activity, increasing neurotransmitter receptor synthesis or membrane insertion, decreasing neurotransmitter degradation, and regulating neurotransmitter receptor conformation. Neurotransmission modulators that increase neurotransmission include neurotransmitters and analogs thereof and neurotransmitter receptor agonists. Neurotransmission modulators may decrease neurotransmission by decreasing neurotransmitter synthesis or release, increasing neurotransmitter reuptake or degradation, decreasing neurotransmitter receptor activity, decreasing neurotransmitter receptor synthesis or membrane insertion, increasing neurotransmitter degradation, regulating neurotransmitter receptor conformation, and disrupting the pre- or postsynaptic machinery. Neurotransmission modulators that decrease or block neurotransmission include antibodies that bind to or block the function of neurotransmitters, neurotransmitter receptor antagonists, and toxins that disrupt synaptic release.

DETAILED DESCRIPTION

Described herein are compositions and methods for the treatment of cancer in a subject (e.g., a mammalian subject, such as a human) by administering SERCA pump inhibitors. SERCA pump inhibitors include inhibitors specific to a single SERCA pump (e.g., SERCA pump-specific inhibitory antibodies) and non-specific inhibitors that could potentially affect other proteins due to their having shared binding partners or signaling pathways with SERCA pumps. These methods and compositions provide new mechanistic approaches for treating cancer.

SERCA Pumps

Sarco/endoplasmic reticulum $Ca^{2+}$-ATPase (SERCA) pumps are calcium P-ATPase pumps. SERCA pumps reside in the sarcoplasmic reticulum (SR) within myocytes. They are calcium ATPase pumps that function by transferring calcium ($Ca^{2+}$) from the cytosol of the cell to the lumen of the SR at the expense of ATP hydrolysis during muscle relaxation, effectively removing calcium from the cytoplasm. SERCA pumps are involved in the normal muscle relaxation and cardiac muscle function. There are 3 major paralogs of SERCA pump: SERCA1 (ATP2A1, Entrez Gene ID: 487), SERCA2 (ATP2A2, Entrez Gene ID: 488), and SERCA3 (ATP2A3, Entrez Gene ID: 489), which are expressed at various levels in different cell types. Phospholamban (PLN, Entrez Gene ID: 5350) and sarcolipin (SLN, Entrez Gene ID: 6588) are the major binding partners of SERCA pumps. The rate at which SERCA pumps move calcium across the SR membrane can be controlled by PLN. When PLN is associated with a SERCA pump, the rate of calcium movement is reduced, while calcium movement increases upon dissociation of PLN from the SERCA pump. Another protein, calsequestrin (CASQ2, Entrez Gene: 845), affects SERCA pump function without directly binding. CASQ2 binds calcium within the SR and helps to reduce the concentration of free calcium, which assists the SERCA pump so that it does not have to pump against a high concentration gradient.

The present invention relates to the discovery that the addition of compounds that inhibit SERCA pumps (thapsigargin, cyclopiazonic acid, and NS-1619) to T cells led to T cell activation and increased interferon gamma (IFNγ) production. These data indicate that inhibition of SERCA pumps can be used as a therapeutic strategy for treating cancer by engaging the immune system. These data also suggest that patients with overexpression of one or more SERCA pumps are at increased risk of developing cancer and would benefit from specific treatments, such as treatment with the compositions and methods described herein.

SERCA Pump Inhibitors

SERCA pump inhibitors described herein can reduce or inhibit SERCA pump expression, function or signaling in order to treat cancer. SERCA pump inhibitors can be grouped into categories based on their mechanism of action and their effect on SERCA pumps: 1) SERCA pump-specific inhibitors (e.g., inhibitors that only disrupt the expression, function or signaling of a single SERCA pump, such as SERCA pump-specific inhibitory antibodies), and 2) SERCA pump function blockers (e.g., inhibitors that prevent SERCA pumps from binding to a binding partner, or carrying out other processes necessary for normal SERCA pump activity, such as SERCA pump inhibitory antibodies that bind to a SERCA pump binding partner).

SERCA Pump-Specific Inhibitors

In some embodiments, the SERCA pump inhibitor is a SERCA pump-specific inhibitor. SERCA pump-specific inhibitors selectively reduce or inhibit the function, expression, or signaling of a single SERCA pump without directly binding to and reducing the function of other related proteins (e.g., other SERCA pumps). SERCA pump-specific inhibitors include SERCA pump-specific inhibitory antibodies or antigen binding fragments thereof (e.g., ATP2A1-specific inhibitory antibodies, ATP2A2-specific inhibitory antibodies, or ATP2A3-specific inhibitory antibodies), inhibitory RNAs directed to a single SERCA pump (e.g., inhibitory RNAs (e.g., short hairpin RNA (shRNA), small interfering RNA (siRNA), or microRNA (miRNA)) directed to ATP2A1, ATP2A2, or ATP2A3), and nucleases directed to a SERCA pump (e.g., a CRISPR associated protein (Cas, e.g., Cas9), a transcription activator-like effector nuclease (TALEN), or a zinc finger nuclease (ZFN) directed to ATP2A1, ATP2A2, or ATP2A3). SERCA pump-specific inhibitors also include small molecule inhibitors (e.g., antagonists) selective for a single SERCA pump. SERCA pump-specific inhibitors can reduce SERCA pump function, expression, or signaling by 5% or more (e.g., 5%, 10%, 15%, 20%, 25%, 30%, 40%, 50%, 60%, 70%, 80%, 90%, 95%, 99%, or more).

In some embodiments, the SERCA pump antibody is a SERCA pump-specific inhibitory antibody (e.g., ATP2A1-specific inhibitory antibody, ATP2A2-specific inhibitory antibody, or ATP2A3-specific inhibitory antibody) or an antigen binding fragment thereof that binds to a SERCA pump and reduces or inhibits SERCA pump function. SERCA pump-specific inhibitory antibodies include antibodies having one or more of the following functional properties: disrupts calcium transport; or antagonizes the SERCA pump. In some embodiments, the SERCA pump-specific inhibitory antibody is an ATP2A2-specific inhibitory that binds to residue P602 of ATP2A2. Antibodies having one or more of these functional properties are routinely screened and selected once the desired functional property is identified herein (e.g., by screening of phage display or other antibody libraries). An exemplary ATP2A3-specific inhibitory antibody is PL/IM430 (sc-81759, Santa Cruz Biotechnology), and is described in Chandrasekera and Lytton, JBC 278:12482-12488, 2003.

In some embodiments, the SERCA pump specific inhibitor is an inhibitory RNA (e.g., siRNA, shRNA, or miRNA) directed to ATP2A1, ATP2A2, or ATP2A3. In some embodiments, the SERCA pump specific inhibitor is a nuclease (e.g., TALEN, ZFN, or Cas, e.g., Cas9) directed to ATP2A1, ATP2A2, or ATP2A3. In some embodiments, the SERCA pump-specific inhibitor is an ATP2A1-, ATP2A2-, or ATP2A3-selective small molecule inhibitor (e.g., antagonist) included in Table 2.

SERCA Pump Function Blockers

In some embodiments, the SERCA pump inhibitor is a SERCA pump function blocker. SERCA pump function blockers reduce or inhibit SERCA pump function by preventing SERCA pumps from interacting with their binding partners (e.g., PLN or a binding partner listed in Table 1), or preventing SERCA pumps from becoming activated. SERCA pump function blockers include SERCA pump-specific inhibitors that reduce or inhibit SERCA pump function or expression (e.g., SERCA pump-specific inhibitory antibodies or antigen binding fragments thereof, inhibitory RNAs or nucleases directed to individual SERCA pumps, and SERCA pump selective small molecule inhibitors), inhibitory RNAs and nucleases directed to SERCA pump binding partners, and small molecule non-selective SERCA pump inhibitors.

SERCA pump binding partners include phospholamban (PLN, Entrez Gene: 5350), sarcolipin (SLN, Entrez Gene: 6588), and calsequestrin (CASQ2, Entrez Gene: 845).

In some embodiments, SERCA pump inhibitory antibodies that bind to SERCA pump binding partners are antibodies that bind to PLN or other binding partners listed in Table 1. In some embodiments, SERCA pump inhibitory antibodies that bind to SERCA pump binding partners have one or more of the following functional properties: inhibit the association of the binding partner with the SERCA pump; or does not have agonistic activity (e.g., does not activate the binding partner). Antibodies having one or more of these functional properties are routinely screened and selected once the desired functional property is identified herein (e.g., by screening of phage display or other antibody libraries).

In some embodiments, the SERCA pump function blocker is an inhibitory RNA (e.g., shRNA, siRNA, or miRNA) directed to a SERCA pump binding partner listed in Table 1. In some embodiments, the SERCA pump function blocker is a nuclease (e.g., TALEN, ZFN, or Cas, e.g., Cas9) directed to a SERCA pump binding partner listed in Table 1.

In some embodiments, the SERCA pump function blocker is a non-selective SERCA pump small molecule inhibitor (e.g., antagonist) included in Table 2.

TABLE 1

SERCA PUMP BINDING PARTNERS

| Binding partner | Symbol | Accession number |
|---|---|---|
| Phospholamban | PLN | 5350 |
| Sarcolipin | SLN | 6588 |
| Calsequestrin | CASQ2 | 845 |

TABLE 2

SERCA PUMP INHIBITORS

| SERCA pump | Inhibitors |
|---|---|
| Non-selective inhibitors | Glucagon (amino acid 19-29 peptide); Paxilline; Thapsigargin; (6ar,11as,11br)-10-acetyl-9-hydroxy-7,7-dimethyl-2,6,6a,7,11a,11b-hexahydro-11h pyrrolo[1',2':2,3]isoindolo[4,5,6-cd]indol-11-one 2,5-di-(tert-butyl)-1,4,benzohydroquinone; Adenosine-5'-[Beta, Gamma-Methylene] Triphosphate; Tetrafluoroaluminate Ion, 2,5-Di-tert-butylhydroquinone; celcoxib; benzothiazepine; sipatrigine; Ethyl 2-amino-6-(3,5-dimethoxyphenyl)-4-(2-ethoxy-2-oxoethyl)-4H-chromene-3-carboxylate (CXL017); curcumin; t 1,3-dibromo-2,4,6-tris (methylisothiouronium) benzene (Br2-TITU) |
| ATP2A1 inhibitors | CHEMBL190620, CHEMBL191633, CHEMBL191927, CHEMBL191997, CHEMBL192075, CHEMBL192173, CHEMBL192239, CHEMBL192507, CHEMBL192566, CHEMBL192710, CHEMBL192778, CHEMBL192808, CHEMBL192939, CHEMBL192942, CHEMBL192952, CHEMBL193009, CHEMBL193186, CHEMBL193205, CHEMBL314556, CHEMBL328508, CHEMBL328881, CHEMBL362946, CHEMBL362947, CHEMBL363400, CHEMBL364964, CHEMBL365351, CHEMBL365703, CHEMBL370025, CHEMBL370465, CHEMBL370514, CHEMBL370930, CHEMBL372869, CHEMBL372891, CHEMBL426816, CHEMBL435107, CHEMBL440027, CHEMBL92908, CHEMBL93514, CHEMBL93580, CHEMBL93581, CHEMBL96926, BDBM50165366, BDBM50165367, BDBM50165368, BDBM50165369 |
| ATP2A2 inhibitors | CHEMBL38017, CHEMBL47823, CHEMBL296933, CHEMBL417529, CHEMBL38224, CHEMBL50665, CHEMBL49865, CHEMBL295215, SBF-1 |

Agent Modalities

A SERCA pump inhibitor can be selected from a number of different modalities. A SERCA pump inhibitor can be a nucleic acid molecule (e.g., DNA molecule or RNA molecule, e.g., mRNA, or a hybrid DNA-RNA molecule), a polypeptide (e.g., an antibody molecule, e.g., an antibody or antigen binding fragment thereof), a nuclease (e.g., Cas9, TALEN, or ZFN), or a small molecule (e.g., a small molecule antagonist of a SERCA pump). A SERCA pump inhibitor can also be a viral vector expressing a SERCA pump inhibitor or a cell infected with a viral vector. Any of these modalities can be a SERCA pump inhibitor directed to target (e.g., to reduce or inhibit) SERCA pump function, SERCA pump expression, SERCA pump binding to a binding partner, or SERCA pump signaling.

The nucleic acid molecule, small molecule, peptide, polypeptide, or antibody molecule can be modified. For example, the modification can be a chemical modification, e.g., conjugation to a marker, e.g., fluorescent marker or a radioactive marker. In other examples, the modification can include conjugation to a molecule that enhances the stability or half-life of the SERCA pump inhibitor (e.g., an Fc domain of an antibody or serum albumin, e.g., human serum albumin). The modification can also include conjugation to an antibody to target the agent to a particular cell or tissue. Additionally, the modification can be a chemical modification, packaging modification (e.g., packaging within a nanoparticle or microparticle), or targeting modification to prevent the agent from crossing the blood brain barrier.

Small Molecules

Numerous small molecule SERCA pump inhibitors (e.g., antagonists) useful in the methods of the invention are described herein and additional small molecule SERCA pump inhibitors useful as therapies for cancer can also be identified through screening based on their ability to reduce or inhibit SERCA pump function or signaling. Small molecules include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organometallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds.

In some embodiments, the small molecule SERCA pump inhibitor is a small molecule SERCA pump antagonist (e.g., BDBM50165366, BDBM50165367, BDBM50165368, BDBM50165369, or others listed in Table 2) or a small molecule SERCA pump binding partner antagonist (e.g., an antagonist of PLN). Small molecule SERCA pump inhibitors can be used to treat a cancer described herein. A pharmaceutical composition including the small molecule SERCA pump inhibitor can be formulated for treatment of a cancer described herein. In some embodiments, a pharmaceutical composition that includes the small molecule SERCA pump inhibitor is formulated for local administration, e.g., to the affected site in a subject.

Antibodies

The SERCA pump inhibitor can be an antibody or antigen binding fragment thereof. For example, a SERCA pump inhibitor described herein is an antibody that reduces or blocks the activity and/or function of a SERCA pump through binding to SERCA pump to block the binding between a SERCA pump and a binding partner.

The making and use of therapeutic antibodies against a target antigen (e.g., against a SERCA pump, e.g., ATP2A1, ATP2A2, or ATP2A3) is known in the art. See, for example, the references cited herein above, as well as Zhiqiang An (Editor), Therapeutic Monoclonal Antibodies: From Bench to Clinic. 1st Edition. Wiley 2009, and also Greenfield (Ed.), Antibodies: A Laboratory Manual. (Second edition) Cold Spring Harbor Laboratory Press 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

Nucleic Acids

Inhibitory RNA

In some embodiments, the SERCA pump inhibitor is an inhibitory RNA molecule, e.g., that acts by way of the RNA interference (RNAi) pathway. An inhibitory RNA molecule can decrease the expression level (e.g., protein level or mRNA level) of a SERCA pump (e.g., ATP2A1, AT2A2, or ATP2A3), a SERCA pump binding partner (e.g., PLN, CASQ2, or SLN), or a molecule required for SERCA pump signaling or function. For example, an inhibitory RNA molecule includes a short interfering RNA, short hairpin RNA, and/or a microRNA that targets a full-length SERCA pump (e.g., ATP2A1, AT2A2, or ATP2A3), or a SERCA pump binding partner (e.g., PLN, CASQ2, or SLN). A siRNA is a double-stranded RNA molecule that typically has a length of about 19-25 base pairs. A shRNA is a RNA molecule including a hairpin turn that decreases expression of target genes via RNAi. shRNAs can be delivered to cells in the form of plasmids, e.g., viral or bacterial vectors, e.g., by transfection, electroporation, or transduction). A microRNA is a non-coding RNA molecule that typically has a length of about 22 nucleotides. MiRNAs bind to target sites on mRNA molecules and silence the mRNA, e.g., by causing cleavage of the mRNA, destabilization of the mRNA, or inhibition of translation of the mRNA. In embodiments, the inhibitory RNA molecule decreases the level and/or activity of a negative regulator of function or a positive regulator of function. In other embodiments, the inhibitory RNA molecule decreases the level and/or activity of an inhibitor of a positive regulator of function.

An inhibitory RNA molecule can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that certain modification can increase nuclease resistance and/or serum stability, or decrease immunogenicity.

In some embodiments, the inhibitory RNA molecule decreases the level and/or activity or function of a SERCA pump (e.g., ATP2A1, AT2A2, or ATP2A3), or a SERCA pump binding partner (e.g., PLN, CASQ2, or SLN). In some embodiments, the inhibitory RNA molecule inhibits expression of a SERCA pump (e.g., ATP2A1, AT2A2, or ATP2A3), or a SERCA pump binding partner (e.g., PLN, CASQ2, or SLN). In other embodiments, the inhibitor RNA molecule increases degradation of a SERCA pump (e.g., ATP2A1, AT2A2, or ATP2A3), or a SERCA pump binding partner (e.g., PLN, CASQ2, or SLN), and/or decreases the stability (i.e., half-life) of a SERCA pump, or a SERCA pump binding partner (e.g., PLN, CASQ2, or SLN). The inhibitory RNA molecule can be chemically synthesized or transcribed in vitro.

The making and use of inhibitory therapeutic agents based on non-coding RNA such as ribozymes, RNAse P, siRNAs, and miRNAs are also known in the art, for example, as described in Sioud, RNA Therapeutics: Function, Design, and Delivery (Methods in Molecular Biology). Humana Press 2010.

Gene Editing

In some embodiments, the SERCA pump inhibitor is a component of a gene editing system. For example, the SERCA pump inhibitor introduces an alteration (e.g., insertion, deletion (e.g., knockout), translocation, inversion, single point mutation, or other mutation) in a SERCA pump (e.g., ATP2A1, AT2A2, or ATP2A3) or a SERCA pump binding partner (e.g., PLN, CASQ2, or SLN). Exemplary gene editing systems include the zinc finger nucleases (ZFNs), Transcription Activator-Like Effector-based Nucleases (TALEN), and the clustered regulatory interspaced short palindromic repeat (CRISPR) system. ZFNs, TALENs, and CRISPR-based methods are described, e.g., in Gaj et al. Trends Biotechnol. 31.7(2013):397-405.

CRISPR refers to a set of (or system including a set of) clustered regularly interspaced short palindromic repeats. A CRISPR system refers to a system derived from CRISPR and Cas (a CRISPR-associated protein) or other nuclease that can be used to silence or mutate a gene described herein. The CRISPR system is a naturally occurring system found in bacterial and archaeal genomes. The CRISPR locus is made up of alternating repeat and spacer sequences. In naturally-occurring CRISPR systems, the spacers are typically sequences that are foreign to the bacterium (e.g., plasmid or phage sequences). The CRISPR system has been modified for use in gene editing (e.g., changing, silencing, and/or enhancing certain genes) in eukaryotes. See, e.g., Wiedenheft et al., Nature 482: 331, 2012. For example, such modification of the system includes introducing into a eukaryotic cell a plasmid containing a specifically-designed CRISPR and one or more appropriate Cas proteins. The CRISPR locus is transcribed into RNA and processed by Cas proteins into small RNAs that include a repeat sequence flanked by a spacer. The RNAs serve as guides to direct Cas proteins to silence specific DNA/RNA sequences, depending on the spacer sequence. See, e.g., Horvath et al., Science 327: 167, 2010; Makarova et al., Biology Direct 1:7, 2006; Pennisi, Science 341: 833, 2013. In some examples, the CRISPR system includes the Cas9 protein, a nuclease that cuts on both strands of the DNA. See, e.g., Id.

In some embodiments, in a CRISPR system for use described herein, e.g., in accordance with one or more methods described herein, the spacers of the CRISPR are derived from a target gene sequence, e.g., from a SERCA pump sequence (e.g., ATP2A1, AT2A2, or ATP2A3) or a sequence of a SERCA pump binding partner (e.g., PLN, CASQ2, or SLN).

In some embodiments, the SERCA pump inhibitor includes a guide RNA (gRNA) for use in a clustered regulatory interspaced short palindromic repeat (CRISPR) system for gene editing. In some embodiments, the SERCA pump inhibitor includes a zinc finger nuclease (ZFN), or an mRNA encoding a ZFN, that targets (e.g., cleaves) a nucleic acid sequence (e.g., DNA sequence) of a SERCA pump (e.g., ATP2A1, AT2A2, or ATP2A3) or a SERCA pump binding partner (e.g., PLN, CASQ2, or SLN). In some embodiments, the SERCA pump inhibitor includes a TALEN, or an mRNA encoding a TALEN, that targets (e.g., cleaves) a nucleic acid sequence (e.g., DNA sequence) of a SERCA pump (e.g., ATP2A1, AT2A2, or ATP2A3) or a SERCA pump binding partner (e.g., PLN, CASQ2, or SLN).

For example, the gRNA can be used in a CRISPR system to engineer an alteration in a gene (e.g., a SERCA pump). In other examples, the ZFN and/or TALEN can be used to engineer an alteration in a gene (e.g., SERCA pump). Exemplary alterations include insertions, deletions (e.g., knockouts), translocations, inversions, single point mutations, or other mutations. The alteration can be introduced in the gene in a cell, e.g., in vitro, ex vivo, or in vivo. In some embodiments, the alteration decreases the level and/or activity of (e.g., knocks down or knocks out) a SERCA pump (e.g., ATP2A1, AT2A2, or ATP2A3) or a SERCA pump binding partner (e.g., PLN, CASQ2, or SLN), e.g., the alteration is a negative regulator of function. In yet another example, the alteration corrects a defect (e.g., a mutation causing a defect), in a SERCA pump.

In certain embodiments, the CRISPR system is used to edit (e.g., to add or delete a base pair) a target gene, e.g., a SERCA pump (e.g., ATP2A1, AT2A2, or ATP2A3) or a SERCA pump binding partner (e.g., PLN, CASQ2, or SLN). In other embodiments, the CRISPR system is used to introduce a premature stop codon, e.g., thereby decreasing the expression of a target gene. In yet other embodiments, the CRISPR system is used to turn off a target gene in a reversible manner, e.g., similarly to RNA interference. In some embodiments, the CRISPR system is used to direct Cas to a promoter of a target gene, e.g., a SERCA pump (e.g., ATP2A1, AT2A2, or ATP2A3) or a SERCA pump binding partner (e.g., PLN, CASQ2, or SLN), thereby blocking an RNA polymerase sterically.

In some embodiments, a CRISPR system can be generated to edit a SERCA pump (e.g., ATP2A1, AT2A2, or ATP2A3) or a SERCA pump binding partner (e.g., PLN, CASQ2, or SLN) using technology described in, e.g., U.S. Publication No. 20140068797; Cong, Science 339: 819, 2013; Tsai, Nature Biotechnol., 32:569, 2014; and U.S. Pat. Nos. 8,871,445; 8,865,406; 8,795,965; 8,771,945; and 8,697,359.

In some embodiments, the CRISPR interference (CRISPRi) technique can be used for transcriptional repression of specific genes, e.g., the gene encoding a SERCA pump (e.g., ATP2A1, AT2A2, or ATP2A3) or a SERCA pump binding partner (e.g., PLN, CASQ2, or SLN). In CRISPRi, an engineered Cas9 protein (e.g., nuclease-null dCas9, or dCas9 fusion protein, e.g., dCas9-KRAB or dCas9-SID4X fusion) can pair with a sequence specific guide RNA (sgRNA). The Cas9-gRNA complex can block RNA polymerase, thereby interfering with transcription elongation. The complex can also block transcription initiation by interfering with transcription factor binding. The CRISPRi method is specific with minimal off-target effects and is multiplexable, e.g., can simultaneously repress more than one gene (e.g., using multiple gRNAs). Also, the CRISPRi method permits reversible gene repression.

In some embodiments, CRISPR-mediated gene activation (CRISPRa) can be used for transcriptional activation, e.g., of one or more genes described herein, e.g., a gene that inhibits a SERCA pump (e.g., ATP2A1, AT2A2, or ATP2A3) or a SERCA pump binding partner (e.g., PLN, CASQ2, or SLN). In the CRISPRa technique, dCas9 fusion proteins recruit transcriptional activators. For example, dCas9 can be used to recruit polypeptides (e.g., activation domains) such as VP64 or the p65 activation domain (p65D) and used with sgRNA (e.g., a single sgRNA or multiple sgRNAs), to activate a gene or genes, e.g., endogenous gene(s). Multiple activators can be recruited by using multiple sgRNAs—this can increase activation efficiency. A variety of activation domains and single or multiple activation domains can be used. In addition to engineering dCas9 to recruit activators, sgRNAs can also be engineered to recruit activators. For example, RNA aptamers can be incorporated into a sgRNA to recruit proteins (e.g., activation domains) such as VP64. In some examples, the synergistic activation mediator (SAM) system can be used for transcriptional activation. In SAM, MS2 aptamers are added to the sgRNA. MS2 recruits the MS2 coat protein (MCP) fused to p65AD and heat shock factor 1 (HSF1). The CRISPRi and CRISPRa techniques are described in greater detail, e.g., in Dominguez et al., Nat. Rev. Mol. Cell Biol. 17:5, 2016, incorporated herein by reference.

Viral Vectors

The SERCA pump inhibitor can be delivered by a viral vector (e.g., a viral vector expressing a SERCA pump inhibitor, e.g., an inhibitory RNA). Viral vectors can also be used to express a neurotoxin from Table 12 for combination therapy with a SERCA pump inhibitor. A viral vector expressing a neurotoxin from Table 12 can be administered to a cell or to a subject (e.g., a human subject or animal model) to decrease or block neurotransmission. Viral vectors can be directly administered (e.g., injected) to a tumor to treat cancer.

Viral genomes provide a rich source of vectors that can be used for the efficient delivery of exogenous genes into a mammalian cell. Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus, replication deficient herpes virus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology (Third Edition) Lippincott-Raven, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the teachings of which are incorporated herein by reference.

Cell-Based Therapies

A SERCA pump inhibitor described herein can be administered to a cell in vitro (e.g., an immune cell), which can subsequently be administered to a subject (e.g., a human subject or animal model). The SERCA pump inhibitor can be administered to the cell to effect an immune response (e.g., activation, polarization, antigen presentation, cytokine production, migration, proliferation, or differentiation) as described herein. Once the immune response is elicited, the cell can be administered to a subject (e.g., injected) to treat cancer. The immune cell can be locally administered (e.g., injected into a tumor).

A SERCA pump inhibitor can also be administered to a cell in vitro (e.g., an immune cell) to alter gene or protein expression in the cell. The SERCA pump inhibitor can decrease the expression of SERCA pump in an immune cell (e.g., an effector T cell, a helper T cell, a cytotoxic T cell, a Th1 cell, a Th2 cell, or a Th17 cell). The SERCA pump inhibitor can be a polypeptide or nucleic acid (e.g., inhibitory RNA) described above. The SERCA pump inhibitor can be an exogenous gene encoded by a plasmid that is introduced into the cell using standard methods (e.g., calcium phosphate precipitation, electroporation, microinjection, infection, lipofection, impalefection, laserfection, or magnetofection). The SERCA pump inhibitor can be a viral vector (e.g., a viral vector expressing a SERCA pump inhibitor) that is introduced to the cell using standard transduction methods. The plasmid or vector can also contain a reporter construct (e.g., a fluorescent reporter) that can be used to confirm expression of the transgene by the immune cell (e.g., an effector T cell, a helper T cell, a cytotoxic T cell, a Th1 cell, a Th2 cell, or a Th17 cell). After the immune cell (e.g., an effector T cell, a helper T cell, a cytotoxic T cell, a Th1 cell, a Th2 cell, or a Th17 cell) has been contacted with a SERCA pump inhibitor, the cell can be administered to a subject (e.g., injected) to treat cancer. The immune cell (e.g., an effector T cell, a helper T cell, a cytotoxic T cell, a Th1 cell, a Th2 cell, or a Th17 cell) can be locally administered (e.g., injected into a tumor).

The cell can be administered to a subject immediately after being contacted with a SERCA pump inhibitor (e.g., within 5, 10, 15, 30, 45, or 60 minutes of being contacted with a SERCA pump inhibitor), or 6 hours, 12 hours, 24 hours, 2 days, 3, days, 4 days, 5, days, 6 days, 7 days or more after being contacted with a SERCA pump inhibitor. The method can include an additional step of evaluating the immune cell for an immune cell activity (e.g., activation, polarization, antigen presentation, cytokine production, migration, proliferation, or differentiation) or modulation of gene expression after contact with a SERCA pump inhibitor and before administration to a subject.

Blood Brain Barrier Permeability

In some embodiments, the SERCA pump inhibitors for use in the present invention are agents that are not capable of crossing, or that do not cross, the blood brain barrier (BBB) of a mammal, e.g., an experimental rodent (e.g., mouse or rat), dog, pig, non-human primate, or a human. The BBB is a highly selective semipermeable membrane barrier that separates the circulating blood from the brain extracellular fluid (e.g., cerebrospinal fluid) in the central nervous system (CNS). The BBB is made up of high-density endothelial cells, which are connected by tight junctions. These cells prevent most molecular compounds in the bloodstream (e.g., large molecules and hydrophilic molecules) from entering the brain. Water, some gases (e.g., oxygen and carbon dioxide), and lipid-soluble molecules (e.g., hydrophobic molecules, such as steroid hormones) can cross the BBB by passive diffusion. Molecules that are needed for neural function, such as glucose and amino acids, are actively transported across the BBB.

A number of approaches can be used to render an agent BBB impermeable. These methods include modifications to increase an agent's size, polarity, or flexibility or reduce its lipophilicity, targeting approaches to direct an agent to another part of the body and away from the brain, and packaging approaches to deliver an agent in a form that does not freely diffuse across the BBB. These approaches can be used to render a BBB permeable SERCA pump inhibitor impermeable, and they can also be used to improve the properties (e.g., cell-specific targeting) of a SERCA pump inhibitor that does not cross the BBB. The methods that can be used to render an agent BBB impermeable are discussed in greater detail herein below.

Formulation of BBB-Impermeable Agents for Enhanced Cell Targeting

One approach that can be used to render a SERCA pump inhibitor BBB impermeable is to conjugate the agent to a targeting moiety that directs it somewhere other than the brain. The targeting moiety can be an antibody for a receptor expressed by the target cell (e.g., N-Acetylgalactosamine for liver transport; DGCR2, GBF1, GPR44 or SerpinB10 for pancreas transport; Secretoglobin, family 1A, member 1 for lung transport). The targeting moiety can also be a ligand of any receptor or other molecular identifier expressed on the target cell in the periphery. These targeting moieties can direct the SERCA pump inhibitor of interest to its corresponding target cell, and can also prevent BBB crossing by directing the agent away from the BBB and increasing the size of the SERCA pump inhibitor via conjugation of the targeting moiety.

SERCA pump inhibitors can also be rendered BBB impermeable through formulation in a particulate delivery system (e.g., a nanoparticle, liposome, or microparticle), such that the agent is not freely diffusible in blood and cannot cross the BBB. The particulate formulation used can be chosen based on the desired localization of the SERCA pump inhibitor (e.g., a tumor, lymph node, lymphoid organ), as particles of different sizes accumulate in different locations. For example, nanoparticles with a diameter of 45 nm or less enter the lymph node, while 100 nm nanoparticles exhibit poor lymph node trafficking. Some examples of the link between particle size and localization in vivo are described in Reddy et al., J Controlled Release 112:26 2006, and Reddy et al., Nature Biotechnology 25:1159 2007.

SERCA pump inhibitors can be tested after the addition of a targeting moiety or after formulation in a particulate delivery system to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A SERCA pump inhibitor that exhibits BBB impermeability can be used in the methods described herein.

Modification of Existing Compounds to Render them BBB Impermeable

There are multiple parameters that have been empirically derived in the field of medicinal chemistry to predict whether a compound will cross the BBB. The most common numeric value for describing permeability across the BBB is the logBB, defined as the logarithmic ratio of the concentration of a compound in the brain and in the blood. Empirical rules of thumb have been developed to predict BBB permeability, including rules regarding molecular size, polar surface area, sum of oxygen and nitrogen atoms, lipophilicity (e.g., partition coefficient between apolar solvent and water), "lipoaffinity", molecular flexibility, and number of rotable bonds (summarized in Muehlbacher et al., J Comput Aided Mol Des. 25: 1095 2011; and Geldenhuys et al., Ther Deliv. 6: 961 2015). Some preferred limits on various parameters for BBB permeability are listed in Table 1 of Ghose et al., ACS Chem Neurosci. 3: 50 2012, which is incorporated herein by reference. Based on the parameters shown in the table, one of skill in the art could modify an existing SERCA pump inhibitor to render it BBB impermeable.

One method of modifying a SERCA pump inhibitor to prevent BBB crossing is to add a molecular adduct that does not affect the target binding specificity, kinetics, or thermodynamics of the agent. Molecular adducts that can be used to render an agent BBB impermeable include polyethylene glycol (PEG), a carbohydrate monomer or polymer, a dendrimer, a polypeptide, a charged ion, a hydrophilic group, deuterium, and fluorine. SERCA pump inhibitors can be tested after the addition of one or more molecular adducts or after any other properties are altered to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A SERCA pump inhibitor that exhibits BBB impermeability can be used in the methods described herein.

Screening for or Development of BBB Impermeable Agents

Another option for developing BBB impermeable agents is to find or develop new agents that do not cross the BBB. One method for finding new BBB impermeable agents is to screen for compounds that are BBB impermeable. Compound screening can be performed using in vitro models (e.g., monolayer models, co-culture models, dynamic models, multi-fluidic models, isolated brain microvessels), in vivo models, and computational models, as described in He et al., Stroke 45:2514 2014; Bickel, NeuroRx 2:15 2005; Wang et al., Int J Pharm 288:349 2005, and Czupalla et al., Methods Mol Biol 1135:415 2014. For example, the ability of a molecule to cross the blood brain barrier can be determined in vitro using a transwell BBB assay in which microvascular endothelial cells and pericytes are co-cultured separated by a thin macroporous membrane, see e.g., Naik et al., J Pharm Sci 101:1337 2012 and Hanada et al., Int J Mol Sci 15:1812 2014; or in vivo by tracking the brain uptake of the target molecule by histology or radio-detection. Compounds would be deemed appropriate for use as SERCA pump inhibitors in the methods described herein if they do not display BBB permeability in the aforementioned models.

Modulation of Immune Cells

The methods described herein can be used to modulate an immune response in a subject or cell by administering to a subject or cell a SERCA pump inhibitor in a dose (e.g., an effective amount) and for a time sufficient to modulate the immune response. These methods can be used to treat a subject in need of modulating an immune response, e.g., a subject with cancer. One way to modulate an immune response is to modulate an immune cell activity. This modulation can occur in vivo (e.g., in a human subject or animal model) or in vitro (e.g., in acutely isolated or cultured cells, such as human cells from a patient, repository, or cell line, or rodent cells). The types of cells that can be modulated include T cells (e.g., peripheral T cells, cytotoxic T cells/CD8+ T cells, T helper cells/CD4+ T cells, memory T cells, regulatory T cells/Tregs, natural killer T cells/NKTs, mucosal associated invariant T cells, and gamma delta T cells), B cells (e.g., memory B cells, plasmablasts, plasma cells, follicular B cells/B-2 cells, marginal zone B cells, B-1 cells, regulatory B cells/Bregs), dendritic cells (e.g., myeloid DCs/conventional DCs, plasmacytoid DCs, or follicular DCs), granulocytes (e.g., eosinophils, mast cells, neutrophils, and basophils), monocytes, macrophages (e.g., peripheral macrophages or tissue resident macrophages or tumor-resident macrophages), myeloid-derived suppressor cells, natural killer (NK) cells, innate lymphoid cells (ILC1, ILC2, ILC3), thymocytes, and megakaryocytes.

The immune cell activities that can be modulated by administering to a subject or contacting a cell with an effective amount of a SERCA pump inhibitor described herein include activation (e.g., macrophage, T cell, NK cell, ILC, B cell, dendritic cell, neutrophil, eosinophil, or basophil activation), phagocytosis (e.g., macrophage, neutrophil, monocyte, mast cell, B cell, eosinophil, or dendritic cell phagocytosis), antibody-dependent cell-mediated phagocytosis (e.g., ADCP by monocytes, macrophages, neutrophils, or dendritic cells), antibody-dependent cell-mediated cytotoxicity (e.g., ADCC by NK cells, ILCs, monocytes, macrophages, neutrophils, eosinophils, dendritic cells, or T cells), polarization (e.g., macrophage polarization toward an M1 or M2 phenotype or T cell polarization), proliferation (e.g., proliferation of B cells, T cells, monocytes, macrophages, dendritic cells, NK cells, ILCs, mast cells, neutrophils, eosinophils, or basophils), lymph node homing (e.g., lymph node homing of T cells, B cells, dendritic cells, or macrophages), lymph node egress (e.g., lymph node egress of T cells, B cells, dendritic cells, or macrophages), recruitment (e.g., recruitment of B cells, T cells, monocytes, ILCs, macrophages, dendritic cells, NK cells, mast cells, neutrophils, eosinophils, or basophils), migration (e.g., migration of B cells, T cells, monocytes, macrophages, dendritic cells, NK cells, ILCs, mast cells, neutrophils, eosinophils, or basophils), differentiation (e.g., regulatory T cell differentiation), immune cell cytokine production, antigen presentation (e.g., dendritic cell, macrophage, and B cell antigen presentation), maturation (e.g., dendritic cell maturation), and degranulation (e.g., mast cell, NK cell, ILCs, cytotoxic T cell, neutrophil, eosinophil, or basophil degranulation). Innervation of lymph nodes or lymphoid organs, development of high endothelial venules (HEVs), and development of ectopic or tertiary lymphoid organs (TLOs) can also be modulated using the methods described herein. Modulation can increase or decrease these activities, depending on the SERCA pump inhibitor used to contact the cell or treat a subject.

In some embodiments, an effective amount of a SERCA pump inhibitor is an amount sufficient to modulate (e.g., increase or decrease) one or more (e.g., 2 or more, 3 or more, 4 or more) of the following immune cell activities in the subject or cell: T cell polarization; T cell activation; dendritic cell activation; neutrophil activation; eosinophil activation; basophil activation; T cell proliferation; B cell proliferation; T cell proliferation; monocyte proliferation; macrophage proliferation; dendritic cell proliferation; NK cell proliferation; ILC proliferation; mast cell proliferation; neutrophil proliferation; eosinophil proliferation; basophil proliferation; cytotoxic T cell activation; circulating monocytes; peripheral blood hematopoietic stem cells; macrophage polarization; macrophage phagocytosis; macrophage ADCP, neutrophil phagocytosis; monocyte phagocytosis; mast cell phagocytosis; B cell phagocytosis; eosinophil phagocytosis; dendritic cell phagocytosis; macrophage activation; antigen presentation (e.g., dendritic cell, macrophage, and B cell antigen presentation); antigen presenting cell migration (e.g., dendritic cell, macrophage, and B cell migration); lymph node immune cell homing and cell egress (e.g., lymph node homing and egress of T cells, B cells, dendritic cells, or macrophages); NK cell activation; NK cell ADCC, mast cell degranulation; NK cell degranulation; ILC activation, ILC ADCC, ILC degranulation; cytotoxic T cell degranulation; neutrophil degranulation; eosinophil degranulation; basophil degranulation; neutrophil recruitment; eosinophil recruitment; NKT cell activation; B cell activation; regulatory T cell differentiation; dendritic cell maturation; development of HEVs; development of TLOs; or lymph node or secondary lymphoid organ innervation. In certain embodiments, the immune response (e.g., an immune cell activity listed herein) is increased or decreased in the subject or cell at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the immune response is increased or decreased in the subject or cell between 5-20%, between 5-50%, between 10-50%, between 20-80%, between 20-70%, between 50-200%, between 100%-500%.

After a SERCA pump inhibitor is administered to treat a patient or contact a cell, a readout can be used to assess the effect on immune cell activity. Immune cell activity can be assessed by measuring a cytokine or marker associated with a particular immune cell type, as listed in Table 3 (e.g., performing an assay listed in Table 3 for the cytokine or marker). In certain embodiments, the parameter is increased or decreased in the subject at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the parameter is increased or decreased in the subject between 5-20%, between 5-50%, between 10-50%, between 20-80%, between 20-70%, between 50-200%, between 100%-500%. A SERCA pump inhibitor can be administered at a dose (e.g., an effective amount) and for a time sufficient to modulate an immune cell activity described herein below.

After a SERCA pump inhibitor is administered to treat a patient or contact a cell, a readout can be used to assess the effect on immune cell migration. Immune cell migration can be assessed by measuring the number of immune cells in a location of interest (e.g., tumor, site of metastasis, lymph node, secondary lymphoid organ, tertiary lymphoid organ). Immune cell migration can also be assessed by measuring a chemokine, receptor, or marker associated with immune cell migration, as listed in Tables 4 and 5. In certain embodiments, the parameter is increased or decreased in the subject at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the parameter is increased or decreased in the subject between 5-20%, between 5-50%, between 10-50%, between 20-80%, between 20-70%, between 50-200%, between 100%-500%. A SERCA pump inhibitor can be administered at a dose (e.g., an effective amount) and for a time sufficient to modulate an immune cell migration as described herein below.

A SERCA pump inhibitor described herein can affect immune cell migration. Immune cell migration between peripheral tissues, the blood, and the lymphatic system as well as lymphoid organs is essential for the orchestration of productive innate and adaptive immune responses. Immune cell migration is largely regulated by trafficking molecules including integrins, immunoglobulin cell-adhesion molecules (IgSF CAMs), cadherins, selectins, and a family of small cytokines called chemokines (Table 4). Cell adhesion molecules and chemokines regulate immune cell migration by both inducing extravasation from the circulation into peripheral tissues and acting as guidance cues within peripheral tissues themselves. For extravasation to occur, chemokines must act in concert with multiple trafficking molecules including C-type lectins (L-, P-, and E-selectin), multiple integrins, and cell adhesion molecules (ICAM-1, VCAM-1 and MAdCAM-1) to enable a multi-step cascade of immune cell capturing, rolling, arrest, and transmigration via the blood endothelial barrier (Table 5). Some trafficking molecules are constitutively expressed and manage the migration of immune cells during homeostasis, while others are specifically upregulated by inflammatory processes such as autoimmunity and cancer.

The expression of trafficking molecules important for extravasation is mainly regulated on specialized blood vessels called HEVs, which are the entry portals from the circulation into the periphery and are usually present in secondary lymphoid organs (SLOs) and chronically inflamed tissue. Chronically inflamed tissues often develop lymphoid-like structures called TLOs that contain structures resembling SLOs including HEVs, lymphoid stromal cells, and confined compartments of T and B lymphocytes. As they can act as major gateways for immune cell migration into peripheral tissues, TLOs have been shown to be important in the pathogenesis of autoimmune disorders and cancer.

Once within peripheral tissues, four modes of immune cell migration have been observed: 1) chemokinesis: migration driven by soluble chemokines, without concentration gradients to provide directional bias, 2) haptokinesis: migration along surfaces presenting immobilized ligands such as chemokines or integrins, without concentration gradients to provide directional bias, 3) chemotaxis: directional migration driven by concentration gradients of soluble chemokines, and 4) haptotaxis: directional migration along surfaces presenting gradients of immobilized ligands such as chemokines or integrins. The response of immune cells to trafficking molecules present on the endothelium depends on the composition, expression, and/or functional activity of their cognate receptors, which in turn depends on activation state and immune cell subtype.

Innate immune cells generally migrate toward inflammation-induced trafficking molecules in the periphery. In contrast, naïve T and B cells constantly re-circulate between the blood and secondary lymphoid organs to screen for their cognate antigen presented by activated dendritic cells (DCs) or fibroblastic reticular cells (FRCs), respectively. If activated by recognition of their cognate antigen and appropriate co-stimulation within SLOs, both cell types undergo a series of complex maturation steps, including differentiation and proliferation, ultimately leading to effector and memory immune cell phenotypes. To reach their peripheral target sites, certain effector and memory T and B cell subsets egress from SLOs to the blood circulation via efferent lymphatics. In order to do so, they migrate toward a Sphingosine-1-phosphate (S1P) gradient sensed using their Sphingosine-1-phosphate receptor 1 (S1P$_1$ or 51 PR1). For successful egress into efferent lymphatics, immune cells need to overcome SLO retention signals through the CCR7/CCL21 axis or through CD69-mediated downregulation of S1P$_1$.

Finally, certain immune cell subsets, for example mature dendritic cells (DCs) and memory T cells, migrate from peripheral tissues into SLOs via afferent lymphatics. To exit from peripheral tissues and enter afferent lymphatics, immune cells again largely depend on the CCR7/CCL21 and S1P$_1$/S1P axis. Specifically, immune cells need to overcome retention signals delivered via the CCR7/CCL21 axis, and migrate toward an S1P gradient established by the lymphatic endothelial cells using S1P$_1$. The selective action of trafficking molecules on distinct immune cell subsets as well as the distinct spatial and temporal expression patterns of both the ligands and receptors are crucial for the fine-tuning of immune responses during homeostasis and disease.

Aberrant immune cell migration is observed in multiple immune-related pathologies. Immune cell adhesion deficiencies, caused by molecular defects in integrin expression, fucosylation of selectin ligands, or inside-out activation of integrins on leukocytes and platelets, lead to impaired immune cell migration into peripheral tissues. This results in leukocytosis and in increased susceptibility to recurrent bacterial and fungal infections, which can be difficult to treat and potentially life-threatening. Alternatively, exaggerated migration of specific immune cell subsets into specific peripheral tissues is associated with a multitude of pathologies. For example, excessive neutrophil accumulation in peripheral tissues contributes to the development of ischemia-reperfusion injury, such as that observed during acute myocardial infarction, stroke, shock and acute respiratory distress syndrome. Excessive Th1 inflammation characterized by tissue infiltration of interferon-gamma secreting effector T cells and activated macrophages is associated with atherosclerosis, allograft rejection, hepatitis, and multiple autoimmune diseases including multiple sclerosis, rheumatoid arthritis, psoriasis, Crohn's disease, type 1 diabetes and lupus erythematodes. Excessive Th2 inflammation characterized by tissue infiltration of IL-4, IL-5, and IL-13 secreting Th2 cells, eosinophils and mast cells is associated with asthma, food allergies and atopic dermatitis.

In the context of tumor biology, the balance between effector immune cell infiltrates eliminating tumor cells and suppressive immune cell infiltrates protecting tumor cells is critical in determining the net outcome of tumor development, namely elimination, equilibrium, or escape. The main anti-tumor immune cell subsets are NK cells, γδ T cells, Th1 CD4+ and cytotoxic CD8+ T cells (CTLs), mature dendritic cells (mDCs), and inflammatory macrophages (often referred to as M1 macrophages). The main pro-tumor immune cell subsets are suppressive tumor-associated macrophages (TAM, often referred to as M2 macrophages), myeloid-derived suppressor cells (MDSC), regulatory T cells (Treg), and immature dendritic cells (iDCs). While effector immune cells subsets are generally attracted to migrate into the tumor microenvironment via CXCR3 and its ligands CXCL9, CXCL10 and CXCL11, suppressive immune cell subsets depend on multiple sets of chemokine and chemokine receptors, including CCR2/CCL2, CCR5/CCL5, CXCR1/CXCL8 (IL8), CXCR2/CXCL5, and CXCR4/CXCL12. Accordingly, the upregulation of CXCL9 and CXCL10 within the tumor generally correlates with good prognosis, and upregulation of suppressive chemokines correlates with bad prognosis of cancer patients.

Specific chemokine pathways not only increase the infiltration of immunosuppressive immune cell subsets, but also promote tumor angiogenesis and metastasis and are thus interesting targets for the development of anti-cancer therapies. Inducing T cell migration into tumors might be especially beneficial in the context of cancer immunotherapy, as a T-cell inflamed microenvironment correlates with good response to these types of interventions.

Finally, tumor-draining lymph nodes (tdLNs) are essential gateways for the induction of adaptive immune responses against tumor cells. However, even though tdLNs are exposed to antigens shed by the upstream tumor cells, they often contain more immunosuppressive cytokines and cells than a non-involved lymph node. This is because a multitude of immunosuppressive molecules are secreted by the upstream tumor microenvironment, thus influencing the immune status of the downstream lymph node. Therefore, strategies that could alter immune cell migration into the tumor-draining lymph node could shift the balance between suppressive and effector immune cells in favor of the latter, thus unleashing potent anti-tumor immune responses.

In some embodiments, a SERCA pump inhibitor described herein increases one or more of T cell proliferation, T cell activation, T cell differentiation, or T cell cytokine production (e.g., T cell production of pro-inflammatory cytokines, e.g., IFNγ). In some embodiments, a SERCA pump inhibitor described herein decreases T cell SERCA pump expression (e.g., the expression of ATP2A1, ATP2A3, and/or ATP2A3). In some embodiments, the T cell is an effector T cell, helper T cell, a cytotoxic T cell (e.g., a CD8+ T cell), Th1 cell, Th2 cell, or Th17 cell. In some embodiments, a SERCA pump inhibitor described herein increases inflammation.

Immune Effects

A variety of in vitro and in vivo assays can be used to determine how a SERCA pump inhibitor affects an immune cell activity. The effect of a SERCA pump inhibitor on T cell polarization in a subject can be assessed by evaluation of cell surface markers on T cells obtained from the subject. A blood sample, lymph node biopsy, or tissue sample can be collected from a subject and T cells from the sample evaluated for one or more (e.g., 2, 3, or 4 or more) Th1-specific markers: T-bet, IL-12R, STAT4, or chemokine receptors CCR5, CXCR6, and CXCR3; or Th2-specific markers: CCR3, CXCR4, or IL-4Ra. T cell polarization can also be assessed using the same methods in an in vivo animal model. This assay can also be performed by adding a SERCA pump inhibitor to T cells in vitro (e.g., T cells obtained from a subject, animal model, repository, or commercial source) and measuring the aforementioned markers to evaluate T cell polarization. These markers can be assessed using flow cytometry, immunohistochemistry, in situ hybridization, and other assays that allow for measurement of cellular markers. Comparing results from before and after administration of a SERCA pump inhibitor can be used to determine its effect.

The effect of a SERCA pump inhibitor on T cell activation in a subject can be assessed by evaluation of cellular markers on T cells obtained from the subject. A blood sample, lymph node biopsy, or tissue sample can be collected from a subject and T cells from the sample evaluated for one or more (e.g., 2, 3, 4 or more) activation markers: CD25, CD71, CD26, CD27, CD28, CD30, CD154, CD40L, CD134, CD69, CD62L or CD44. T cell activation can also be assessed using the same methods in an in vivo animal model. This assay can also be performed by adding a SERCA pump inhibitor to T cells in vitro (e.g., T cells obtained from a subject, animal model, repository, or commercial source) and measuring the aforementioned markers to evaluate T cell activation. Similar approaches can be used to assess the effect of a SERCA pump inhibitor on activation of other immune cells, such as eosinophils (markers: CD35, CD11b, CD66, CD69 and CD81), dendritic cells (makers: IL-8, MHC class II, CD40, CD80, CD83, and CD86), basophils (CD63, CD13, CD4, and CD203c), and neutrophils (CD11 b, CD35, CD66b and CD63). These markers can be assessed using flow cytometry, immunohistochemistry, in situ hybridization, and other assays that allow for measurement of cellular markers. Comparing results from before and after administration of a SERCA pump inhibitor can be used to determine its effect.

The effect of a SERCA pump inhibitor on immune cell activation can also be assessed through measurement of secreted cytokines and chemokines. An activated immune cell (e.g., T cell, B cell, macrophage, monocyte, dendritic cell, eosinophil, basophil, mast cell, NK cell, ILC, or neutrophil) can produce pro-inflammatory cytokines and chemokines (e.g., IL-1β, IL-5, IL-6, IL-8, IL-10, IL-12, IL-13, IL-18, TNFα, and IFN-γ). Activation can be assessed by measuring cytokine levels in a blood sample, lymph node biopsy, or tissue sample from a human subject or animal model, with higher levels of pro-inflammatory cytokines following treatment with a SERCA pump inhibitor indicating increased activation, and lower levels indicating decreased activation. Activation can also be assessed in vitro by measuring cytokines secreted into the media by cultured cells. Cytokines can be measured using ELISA, western blot analysis, and other approaches for quantifying secreted proteins. Comparing results from before and after administration of a SERCA pump inhibitor can be used to determine its effect.

The effect of a SERCA pump inhibitor on T cell proliferation in a subject can be assessed by evaluation of markers of proliferation in T cells obtained from the subject. A blood sample, lymph node biopsy, or tissue sample can be collected from a subject and T cells from the sample evaluated for Ki67 marker expression. T cell proliferation can also be assessed using the same methods in an in vivo animal model. This assay can also be performed by adding a SERCA pump inhibitor to T cells in vitro (e.g., T cells obtained from a subject, animal model, repository, or commercial source) and measuring Ki67 to evaluate T cell proliferation. Assessing whether a SERCA pump inhibitor induces T cell proliferation can also be performed by in vivo (e.g., in a human subject or animal model) by collecting blood samples before and after SERCA pump inhibitor administration and comparing T cell numbers, and in vitro by quantifying T cell numbers before and after contacting T cells with a SERCA pump inhibitor. These approaches can also be used to measure the effect of a SERCA pump inhibitor on proliferation of any immune cell (e.g., B cells, T cells, macrophages, monocytes, dendritic cells, NK cells, ILCs, mast cells, eosinophils, basophils, and neutrophils). Ki67 can be assessed using flow cytometry, immunohistochemistry, in situ hybridization, and other assays that allow for measurement of nuclear markers. Comparing results from before and after administration of a SERCA pump inhibitor can be used to determine its effect.

The effect of a SERCA pump inhibitor on cytotoxic T cell activation in a subject can be assessed by evaluation of T cell granule markers in T cells obtained from the subject. A blood sample, lymph node biopsy, or tissue sample can be collected from a subject and T cells from the sample evaluated for granzyme or perforin expression. Cytotoxic T cell activation can also be assessed using the same methods in an in vivo animal model. This assay can also be performed by adding a SERCA pump inhibitor to cytotoxic T cells in vitro (e.g., cytotoxic T cells obtained from a subject, animal model, repository, or commercial source) and measuring the aforementioned markers to evaluate T cell proliferation. These markers can be detected in the media from cytotoxic T cell cultures. Techniques including ELISA, western blot analysis can be used to detect granzyme and perforin in conditioned media, flow cytometry, immunohistochemistry, in situ hybridization, and other assays can detect intracellular granzyme and perforin and their synthesis. Comparing results from before and after administration of a SERCA pump inhibitor can be used to determine its effect.

The effect of a SERCA pump inhibitor on circulating monocytes in a subject can be assessed by evaluation of cell surface markers on primary blood mononuclear cells obtained from the subject. A blood sample, lymph node biopsy, or tissue sample can be collected from a subject and monocytes from the sample evaluated for CD14 and/or CD16 expression. Circulating monocytes can also be assessed using the same methods in an in vivo animal model. This assay can be performed by taking a blood sample before treatment with a SERCA pump inhibitor and comparing it to a blood sample taken after treatment. CD14 and CD16 can be detected using flow cytometry, immunohistochemistry, western blot analysis, or any other technique that can measure cell surface protein levels. Comparing results from before and after administration of a SERCA pump inhibitor can be used to determine its effect. This assay can be used to detect the number of monocytes in the bloodstream or to determine whether monocytes have adopted a CD14+/CD16+ phenotype, which indicates a pro-inflammatory function.

The effect of a SERCA pump inhibitor on peripheral blood hematopoietic stem cells in a subject can be assessed by evaluation of cell surface markers on primary blood mononuclear cells obtained from the subject. A blood sample, lymph node biopsy, or tissue sample can be collected from a subject and stem cells from the sample evaluated for one or more (2, 3 or 4 or more) specific markers: CD34, c-kit, Sca-1, or Thy1.1. Peripheral blood hematopoietic stem cells can also be assessed using the same methods in an in vivo animal model. This assay can be performed by taking a blood sample before treatment with a SERCA pump inhibitor and comparing it to a blood sample taken after treatment. The aforementioned markers can be detected using flow cytometry, immunohistochemistry, western blot analysis, or any other technique that can measure cell surface protein levels. Comparing results from before and after administration of a SERCA pump inhibitor can be used to determine its effect. This assay can be used to detect the number of stem cells mobilized into the bloodstream or to determine whether treatment induces differentiation into a particular hematopoietic lineage (e.g., decreased CD34 and increased GPA indicates differentiation into red blood cells, decreased CD34 and increased CD14 indicates differentiation into monocytes, decreased CD34 and increased CD11b or CD68 indicates differentiation into macrophages, decreased CD34 and increased CD42b indicates differentiation into platelets, decreased CD34 and increased CD3 indicates differentiation into T cells, decreased CD34 and increased CD19 indicates differentiation into B cells, decreased CD34 and increased CD25 or CD69 indicates differentiation into activated T cells, decreased CD34 and increased CD1c, CD83, CD141, CD209, or MHC II indicates differentiation into dendritic cells, decreased CD34 and increased CD56 indicates differentiation into NK cells, decreased CD34 and increased CD15 indicates differentiation into neutrophils, decreased CD34 and increased 2D7 antigen, CD123, or CD203c indicates differentiation into basophils, and decreased CD34 and increased CD193, EMR1, or Siglec-8 indicates differentiation into eosinophils.

The effect of a SERCA pump inhibitor on macrophage polarization in a subject can be assessed by evaluation of cellular markers in macrophages cells obtained from the subject. A blood sample, lymph node biopsy, or tissue sample can be collected from a subject and macrophages from the sample evaluated for one of more (2, 3 or 4 or more) specific markers. Markers for M1 polarization include IL-12, TNF, IL-1β, IL-6, IL-23, MARCO, MHC-II, CD86, iNOS, CXCL9, and CXCL10. Markers for M2 polarized macrophages include IL-10, IL1-RA, TGFβ, MR, CD163, DC-SIGN, Dectin-1, HO-1, arginase (Arg-1), CCL17, CCL22 and CCL24. Macrophage polarization can also be assessed using the same methods in an in vivo animal model. This assay can also be performed on cultured macrophages obtained from a subject, an animal model, repository, or commercial source to determine how contacting a macrophage with a SERCA pump inhibitor affects polarization. The aforementioned markers can be evaluated by comparing measurements obtained before and after administration of a SERCA pump inhibitor to a subject, animal model, or cultured cell. Surface markers or intracellular proteins (e.g., MHC-11, CD86, iNOS, CD163, Dectin-1, HO-1, Arg-1, etc.) can be measured using flow cytometry, immunohistochemistry, in situ hybridization, or western blot analysis, and secreted proteins (e.g., IL-12, TNF, IL-1β, IL-10, TGFβ, IL1-RA, chemokines CXC8, CXC9, CCL17, CCL22, and CCL24, etc.) can be measured using the same methods or by ELISA or western blot analysis of culture media or blood samples. Comparing results from before and after administration of a SERCA pump inhibitor can be used to determine its effect.

The effect of a SERCA pump inhibitor on macrophage phagocytosis in a subject can be assessed by culturing macrophages obtained from the subject with fluorescent beads. A blood sample, lymph node biopsy, or tissue sample can be collected from a subject and macrophages from the sample evaluated for engulfment of fluorescent beads. This assay can also be performed on cultured macrophages obtained from an animal model, repository, or commercial source to determine how contacting a macrophage with a SERCA pump inhibitor affects phagocytosis. The same phagocytosis assay can be used to evaluate the effect of a SERCA pump inhibitor on phagocytosis in other immune cells (e.g., neutrophils, monocytes, mast cells, B cells, eosinophils, or dendritic cells). Comparing results from before and after administration of a SERCA pump inhibitor can be used to determine its effect on phagocytosis.

In some embodiments, phagocytosis is ADCP. ADCP can be assessed using similar methods to those described above by incubating immune cells (e.g., macrophages, neutrophils, monocytes, mast cells, B cells, eosinophils, or dendritic cells) isolated from a blood sample, lymph node biopsy, or tissue sample with fluorescent beads coated with IgG antibodies. In some embodiments, immune cells are incubated with a target cell line that has been pre-coated with antibodies to a surface antigen expressed by the target cell line. ADCP can be evaluated by measuring fluorescence inside the immune cell or quantifying the number of beads or cells engulfed. This assay can also be performed on cultured immune cells obtained from an animal model, repository, or commercial source to determine how contacting an immune cell with a SERCA pump inhibitor affects ADCP. The ability of an immune cell to perform ADCP can also be evaluated by assessing expression of certain Fc receptors (e.g., FcγRIIa, FcγRIIIa, and FcγRI). Fc receptor expression can be assessed using flow cytometry, immunohistochemistry, in situ hybridization, or other assays that allow for measurement of cell surface markers. Comparing phagocytosis or Fc receptor expression before and after administration of a SERCA pump inhibitor can be used to determine its effect on ACDP.

The effect of a SERCA pump inhibitor on macrophage activation in a subject can be assessed by evaluation of cell surface markers on macrophages cells obtained from the subject. A blood sample, lymph node biopsy, or tissue sample can be collected from a subject and macrophages from the sample evaluated for one or more (e.g., 1, 2, 3 or 4 or more) specific markers: F4/80, HLA molecules (e.g., MHC-II), CD80, CD68, CD11b, or CD86. Macrophage activation can also be assessed using the same methods in an in vivo animal model. This assay can also be performed by adding a SERCA pump inhibitor to macrophages in vitro (e.g., macrophages obtained from a subject, animal model, repository, or commercial source) and measuring the aforementioned markers to evaluate macrophage activation. These markers can be assessed using flow cytometry, immunohistochemistry, in situ hybridization, and other assays that allow for measurement of cell surface markers. As mentioned above, macrophage activation can also be evaluated based on cytokine production (e.g., pro-inflammatory cytokine production) as measured by ELISA and western blot analysis. Comparing results from before and after administration of a SERCA pump inhibitor can be used to determine its effect.

The effect of a SERCA pump inhibitor on antigen presentation in a subject can be assessed by evaluation of cell surface markers on antigen presenting cells (e.g., dendritic cells, macrophages, and B cells) obtained from the subject. A blood sample, lymph node biopsy, or tissue sample can be collected from a subject and antigen presenting cells (e.g., dendritic cells, macrophages, and B cells) from the sample evaluated for one or more (e.g., 2, 3 or 4 or more) specific markers: CD11c, CD11b, HLA molecules (e.g., MHC-II), CD40, B7, IL-2, CD80 or CD86. Antigen presentation can also be assessed using the same methods in an in vivo animal model. This assay can also be performed by adding a SERCA pump inhibitor to antigen presenting cells (e.g., dendritic cells) in vitro (e.g., antigen presenting cells obtained from a subject, animal model, repository, or commercial source) and measuring the aforementioned markers to evaluate antigen presentation. These markers can be assessed using flow cytometry, immunohistochemistry, in situ hybridization, and other assays that allow for measurement of cell surface markers. Comparing results from before and after administration of a SERCA pump inhibitor can be used to determine its effect.

The effect of a SERCA pump inhibitor on antigen presenting cell migration in a subject can be assessed by evaluation of cell surface markers on antigen presenting cells (e.g., dendritic cells, B cells, and macrophages) obtained from the subject. A blood sample, lymph node biopsy, or tissue sample can be collected from a subject and antigen presenting cells (e.g., dendritic cells, B cells, and macrophages) from the sample evaluated for CCR7 expression. Antigen presenting cell migration can also be assessed using the same methods in an in vivo animal model. This assay can also be performed by adding a SERCA pump inhibitor to antigen presenting cells (e.g., dendritic cells, B cells, and macrophages) in vitro (e.g., antigen presenting cells obtained from a subject, animal model, repository, or commercial source) and measuring CCR7 to evaluate antigen presenting cell migration. CCR7 can be assessed using flow cytometry, immunohistochemistry, in situ hybridization, and other assays that allow for measurement of cell surface markers. Comparing results from before and after administration of a SERCA pump inhibitor can be used to determine its effect.

The effect of a SERCA pump inhibitor on lymph node immune cell homing and cell egress in a subject can be assessed by evaluation of cell surface markers on T or B cells obtained from the subject. A blood sample, lymph node biopsy, or tissue sample can be collected from a subject and T or B cells from the sample evaluated for one or more specific markers: CCR7 or S1PR1. Lymph node immune cell homing and cell egress can also be assessed using the same methods in an in vivo animal model. This assay can also be performed by adding a SERCA pump inhibitor to T or B cells in vitro (e.g., T or B cells obtained from a subject, animal model, repository, or commercial source) and measuring the aforementioned markers to evaluate T or B cell lymph node homing. These markers can also be used to assess lymph node homing and cell egress of dendritic cells and macrophages. CCR7 and S1PR1 can be assessed using flow cytometry, immunohistochemistry, in situ hybridization, and other assays that allow for measurement of cell surface markers. If using an animal model, lymph nodes or sites of inflammation can be imaged in vivo (e.g., using a mouse that expresses fluorescently labeled T or B cells) or after biopsy to determine whether T or B cell numbers change as a result of administration of a SERCA inhibitor. Comparing results from before and after administration of a SERCA pump inhibitor can be used to determine its effect.

In some embodiments, a SERCA pump inhibitor increases homing or decreases egress of naïve T cells into or out of secondary lymphoid organs prior to antigen challenge (e.g., prior to administration of a vaccine) to generate a better antigen-specific response.

The effect of a SERCA pump inhibitor on NK cell activation in a subject can be assessed by evaluation of cell surface markers on NK cells obtained from the subject. A blood sample, lymph node biopsy, or tissue sample can be collected from a subject and NK cells from the sample evaluated for one or more (e.g., 2, 3 or 4 or more) specific markers: CD117, NKp46, CD94, CD56, CD16, KIR, CD69, HLA-DR, CD38, KLRG1, and TIA-1. NK cell activation can also be assessed using the same methods in an in vivo animal model. This assay can also be performed by adding a SERCA pump inhibitor to NK cells in vitro (e.g., NK cells obtained from a subject, animal model, repository, or commercial source) and measuring the aforementioned markers to evaluate NK cell activation. The effect of a SERCA pump inhibitor can be determined by comparing results from before and after SERCA pump inhibitor administration.

In some embodiments, activated NK cells have increased lytic function or are cytotoxic (e.g., capable of performing ADCC). The effect of a SERCA pump inhibitor on ADCC can be assessed by incubating immune cells capable of ADCC (e.g., NK cells, monocytes, macrophages, neutrophils, eosinophils, dendritic cells, or T cells) with a target cell line that has been pre-coated with antibodies to a surface antigen expressed by the target cell line. ADCC can be assessed by measuring the number of surviving target cells with a fluorescent viability stain or by measuring the secretion of cytolytic granules (e.g., perforin, granzymes, or other cytolytic proteins released from immune cells). Immune cells can be collected from a blood sample, lymph node biopsy, or tissue sample from a human subject or animal model treated with a SERCA pump inhibitor. This assay can also be performed by adding a SERCA pump inhibitor to immune cells in vitro (e.g., immune cells obtained from a subject, animal model, repository, or commercial source). The effect of a SERCA pump inhibitor on ADCC can be determined by comparing results from before and after SERCA pump inhibitor administration.

The effect of a SERCA pump inhibitor on ILC activation in a subject can be assessed by evaluation of cell surface markers on ILCs obtained from the subject. A blood sample, lymph node biopsy, or tissue sample can be collected from a subject and ILCs from the sample evaluated for one or more (e.g., 2, 3 or 4 or more) specific markers: NKp46, CD69, T-bet, RORα, GATA3, and RORγt. ILC activation can also be assessed using the same methods in an in vivo animal model. This assay can also be performed by adding a SERCA pump inhibitor to ILCs in vitro (e.g., ILCs obtained from a subject, animal model, repository, or commercial source) and measuring the aforementioned markers to evaluate ILC activation. The effect of a SERCA pump inhibitor can be determined by comparing results from before and after SERCA pump inhibitor administration.

In some embodiments, activated ILCs have increased lytic function or are cytotoxic (e.g., capable of performing ADCC). The effect of a SERCA pump inhibitor on ADCC can be assessed by incubating immune cells capable of ADCC (e.g., ILCs, monocytes, macrophages, neutrophils, eosinophils, dendritic cells, or T cells) with a target cell line that has been pre-coated with antibodies to a surface antigen expressed by the target cell line. ADCC can be assessed by measuring the number of surviving target cells with a fluorescent viability stain or by measuring the secretion of cytolytic granules (e.g., perforin, granzymes, or other cytolytic proteins released from immune cells). Immune cells can be collected from a blood sample, lymph node biopsy, or tissue sample from a human subject or animal model treated with a SERCA pump inhibitor. This assay can also be performed by adding a SERCA pump inhibitor to immune cells in vitro (e.g., immune cells obtained from a subject, animal model, repository, or commercial source). The effect of a SERCA pump inhibitor on ADCC can be determined by comparing results from before and after SERCA pump inhibitor administration. In some embodiments, the SERCA pump inhibitor decreases ILC ADCC of auto-antibody coated cells (e.g., to treat autoimmune disease). In some embodiments, the SERCA pump inhibitor increases ILC ADCC of antibody-opsonized infectious agents.

The effect of a SERCA pump inhibitor on mast cell degranulation in a subject can be assessed by evaluation of markers in mast cells obtained from the subject. A blood sample, lymph node biopsy, or tissue sample can be collected from a subject and mast cells from the sample evaluated for one or more (e.g., 1, 2, 3 or 4 or more) specific markers: IgE, histamine, IL-4, TNFα, CD300a, tryptase, or MMP9. Mast cell degranulation can also be assessed using the same methods in an in vivo animal model. This assay can also be performed by adding a SERCA pump inhibitor to mast cells in vitro (e.g., mast cells obtained from a subject, animal model, repository, or commercial source) and measuring the aforementioned markers to evaluate mast cell degranulation. Some of these markers (e.g., histamine, TNFα, and IL-4) can be detected by measuring levels in the mast cell culture medium after mast cells are contacted with a SERCA pump inhibitor. The effect of a SERCA pump inhibitor can be determined by comparing results from before and after SERCA pump inhibitor administration. This approach can also be used to evaluate the effect of a SERCA pump inhibitor on degranulation by other cells, such as neutrophils (markers: CD11 b, CD13, CD18, CD45, CD15, CD66b IL-1β, IL-8, and IL-6), eosinophils (markers: major basic protein (MBP), eosinophil cationic protein (ECP), eosinophil peroxidase (EPX), eosinophil-derived neurotoxin (EDN)), basophils (markers: histamine, heparin, chondroitin, elastase, lysophospholipase, and LTD-4), NK cells (markers: LAMP-1, perforin, and granzymes), and cytotoxic T cells (markers: LAMP-1, perforin, and granzymes). Markers can be detected using flow cytometry, immunohistochemistry, ELISA, western blot analysis, or in situ hybridization.

The effect of a SERCA pump inhibitor on neutrophil recruitment in a subject can be assessed by evaluation of cell surface markers on neutrophils obtained from the subject. A blood sample, lymph node biopsy, or tissue sample can be collected from a subject and neutrophils from the sample evaluated for one or more (e.g., 1, 2, 3 or 4 or more) specific markers: CD11b, CD14, CD114, CD177, CD354, or CD66. To determine whether neutrophils are being recruited to a specific site (e.g., tumor), the same markers can be measured in a tumor biopsy. Neutrophil recruitment can also be assessed using the same methods in an in vivo animal model. This assay can also be performed by adding a SERCA pump inhibitor to neutrophils in vitro (e.g., neutrophils obtained from a subject, animal model, repository, or commercial source) and measuring the aforementioned markers to evaluate neutrophil recruitment. These markers can be assessed using flow cytometry, immunohistochemistry, in situ hybridization, and other assays that allow for measurement of cell surface markers. The effect of a SERCA pump inhibitor can be determined by comparing results from before and after SERCA pump inhibitor administration.

The effect of a SERCA pump inhibitor on eosinophil recruitment in a subject can be assessed by evaluation of cell surface markers on eosinophil obtained from the subject. A blood sample, lymph node biopsy, or tissue sample can be collected from a subject and eosinophils from the sample evaluated for one or more (e.g., 1, 2, 3 or 4 or more) specific markers: CD15, IL-3R, CD38, CD106, CD294 or CD85G. To determine whether eosinophils are being recruited to a specific site (e.g., a tumor), the same markers can be measured in a tumor biopsy. Eosinophil recruitment can also be assessed using the same methods in an in vivo animal model. This assay can also be performed by adding a SERCA pump inhibitor to eosinophils in vitro (e.g., eosinophils obtained from a subject, animal model, repository, or commercial source) and measuring the aforementioned markers to evaluate eosinophil recruitment. These markers can be assessed using flow cytometry, immunohistochemistry, in situ hybridization, and other assays that allow for measurement of cell surface markers. The effect of a SERCA pump inhibitor can be determined by comparing results from before and after SERCA pump inhibitor administration.

The effect of a SERCA pump inhibitor on NKT cell activation in a subject can be assessed by evaluation of cell surface markers on NKT cells obtained from the subject. A blood sample, lymph node biopsy, or tissue sample can be collected from a subject and NKT cells from the sample evaluated for one or more specific markers: CD272 or CD352. Activated NKT cells produce IFN-γ, IL-4, GM-CSF, IL-2, IL-13, IL-17, IL-21 and TNFα. NKT cell activation can also be assessed using the same methods in an in vivo animal model. This assay can also be performed by adding a SERCA pump inhibitor to NKT cells in vitro (e.g., NKT cells obtained from a subject, animal model, repository, or commercial source) and measuring the aforementioned markers to evaluate NKT cell activation. Cell surface markers CD272 and CD352 can be assessed using flow cytometry, immunohistochemistry, in situ hybridization, and other assays that allow for measurement of cell surface markers. The secreted proteins can be detected in blood samples or cell culture media using ELISA, western blot analysis, or other methods for detecting proteins in solution. The effect of a SERCA pump inhibitor can be determined by comparing results from before and after SERCA pump inhibitor administration.

The effects of a SERCA pump inhibitor on B cell activation in a subject can be assessed by evaluation of cell surface markers on B cells obtained from the subject. A blood sample, lymph node biopsy, or tissue sample can be collected from a subject and B cells from the sample evaluated for one or more (e.g., 2, 3 or 4 or more) specific markers: CD19, CD20, CD40, CD80, CD86, CD69, IgM, IgD, IgG, IgE, or IgA. B cell activation can also be assessed using the same methods in an in vivo animal model. This assay can also be performed by adding a SERCA pump inhibitor to B cells in vitro (e.g., B cells obtained from a subject, animal model, repository, or commercial source) and measuring the aforementioned markers to evaluate B cell activation. These markers can be assessed using flow cytometry, immunohistochemistry, in situ hybridization, and other assays that allow for measurement of cell surface markers. The effect of a SERCA pump inhibitor can be determined by comparing results from before and after SERCA pump inhibitor administration.

The effect of a SERCA pump inhibitor on regulatory T cell differentiation in a subject can be assessed by evaluation of markers in regulatory T cells obtained from the subject. A blood sample, lymph node biopsy, or tissue sample can be collected from a subject and regulatory T cells from the sample evaluated for one or more (e.g., 1, 2, 3, 4 or more) specific markers: CD4, CD25, or FoxP3. Regulatory T cell differentiation can also be assessed using the same methods in an in vivo animal model. This assay can also be performed by adding a SERCA pump inhibitor to regulatory T cells in vitro (e.g., regulatory T cells obtained from a subject, animal model, repository, or commercial source) and measuring the aforementioned markers to evaluate regulatory T cell differentiation. These markers can be assessed using flow cytometry, immunohistochemistry, in situ hybridization, and other assays that allow for measurement of cellular markers. The effect of a SERCA pump inhibitor can be determined by comparing results from before and after SERCA pump inhibitor administration.

The effect of a SERCA pump inhibitor on innervation of a lymph node or secondary lymphoid organ can be assessed by evaluation of neuronal markers in a lymph node or secondary lymphoid organ biopsy sample obtained from a human subject or animal model. A biopsy can be collected from the subject and evaluated for one or more (e.g., 1, 2, 3, 4, or 4 or more) neuronal markers selected from: Neurofilament, synapsin, synaptotagmin, or neuron specific enolase. Lymph node innervation can also be assessed using electrophysiological approaches (e.g., recording neuronal activity in a lymph node or secondary lymphoid organ in a human subject or animal model). The effect of a SERCA pump inhibitor can be determined by comparing results from before and after SERCA pump inhibitor administration.

The SERCA pump inhibitor can also reduce the number of nerve fibers in the affected tissue or reduce the activity of peripheral nerve fibers in the affected tissue. For example, the method includes administering to the subject (e.g., a human subject or animal model) a SERCA pump inhibitor in an amount and for a time sufficient to reduce the number of nerve fibers in the affected tissue or reduce the activity of peripheral nerve fibers in the affected tissue. The affected tissue can be a lymph node, a lymphoid organ, a tumor, tumor micro-environment, site of metastasis, or the bone marrow niche. The number of nerve fibers in the affected tissue or the activity of peripheral nerve fibers in the affected tissue can be decreased in the subject at least 1%, 2%, 5%, 10%, 15%, 20%, 25%, 30%, 35%, 40%, 50%, 60%, 70%, 80%, 90%, 95% or more, compared to before the administration. The number of nerve fibers in the affected tissue or the activity of peripheral nerve fibers in the affected tissue can be decreased in the subject between 5-20%, between 5-50%, between 10-50%, between 20-80%, between 20-70%.

The SERCA pump inhibitor can also increase the number of nerve fibers in the affected tissue or increase the activity of peripheral nerve fibers in the affected tissue. For example, the method includes administering to the subject (e.g., a human subject or animal model) a SERCA pump inhibitor in an amount and for a time sufficient to increase the number of nerve fibers in the affected tissue or increase the activity of peripheral nerve fibers in the affected tissue. The affected tissue can be a lymph node, a lymphoid organ, a tumor, tumor micro-environment, site of metastasis, or the bone marrow niche. The number of nerve fibers in the affected tissue or the activity of peripheral nerve fibers in the affected tissue can be increased in the subject at least 1%, 2%, 5%, 10%, 15%, 20%, 25%, 30%, 35%, 40%, 50%, 60%, 70%, 80% or more, compared to before the administration. The number of nerve fibers in the affected tissue or the activity of peripheral nerve fibers in the affected tissue can be increased in the subject between 5-20%, between 5-50%, between 10-50%, between 20-80%, between 20-70%.

The nerve fibers that are modulated can be part of the peripheral nervous system, e.g., a somatic nerve, an autonomic nerve, a sensory nerve, a cranial nerve, an optic nerve, an olfactory nerve, a sympathetic nerve, a parasympathetic nerve, a chemoreceptor, a photoreceptor, a mechanoreceptor, a thermoreceptor, a nociceptor, an efferent nerve fiber, or an afferent nerve fiber.

The effect of a SERCA pump inhibitor on immune cell cytokine production can be assessed by evaluation of cellular markers in an immune cell sample obtained from a human subject or animal model. A blood sample, lymph node biopsy, or tissue sample can be collected for the subject and evaluated for one or more (e.g., 1, 2, 3, 4, or 4 or more) cytokine markers selected from: pro-inflammatory cytokines (e.g., IL-1β, IL-5, IL-6, IL-8, IL-10, IL-12, IL-13, IL-18, TNFα, IFNγ, GMCSF), pro-survival cytokines (e.g., IL-2, IL-4, IL-6, IL-7, and IL-15) and anti-inflammatory cytokines (e.g., IL-4, IL-10, IL-11, IL-13, IFNα, and TGFβ). Some cytokines can function as both pro- and anti-inflammatory cytokines depending on context or indication (e.g., IL-4 is often categorized as an anti-inflammatory cytokine, but plays a pro-inflammatory role in mounting an allergic or anti-parasitic immune response). Cytokines can be also detected in the culture media of immune cells contacted with a SERCA pump inhibitor. Cytokines can be detected using ELISA, western blot analysis, or other methods for detecting protein levels in solution. The effect of a SERCA pump inhibitor can be determined by comparing results from before and after SERCA pump inhibitor administration.

In some embodiments, a SERCA pump inhibitor decreases or prevents the development of TLOs to decrease local inflammation in autoimmune diseases. TLOs are highly similar to SLOs and exhibit T and B cell compartmentalization, APCs such as DCs and follicular DCs, stromal cells, and a highly organized vascular system of high endothelial venules. In some embodiments, a SERCA pump inhibitor decreases or prevents the development of HEVs within tertiary lymphoid organs to decrease local inflammation in autoimmune diseases. HEVs can be detected using the monoclonal antibody MECA-79.

In some embodiments, a SERCA pump inhibitor modulates dendritic cell maturation (e.g., activation). Dendritic cell maturation can be increased to promote their migration from peripheral tissues into secondary lymphoid organs to improve T cell activation in the draining lymph node (e.g., to increase vaccine efficacy or to increase priming of an anti-tumor immune response). Dendritic cell maturation can be decreased to decrease their migration from peripheral tissues into secondary lymphoid organs to inhibit T cell activation in the draining lymph node (e.g., to improve outcomes in organ transplantation or to reduce the severity of or treat autoimmune diseases).

The effect of a SERCA pump inhibitor on immune cell recruitment or migration to a tumor can be assessed by evaluation of cellular markers on immune cells obtained from a human subject or animal model. A blood sample or tumor biopsy can be collected from a human subject or animal model and T cells, B cells, dendritic cells, or macrophages can be evaluated for marker CCR7. Immune cell recruitment to a tumor can also be assessed by taking a tumor biopsy before and after administration of a SERCA pump inhibitor to a human subject or animal model and quantifying the number of immune cells in the tumor. Immune cells can be identified based on the markers described above and others listed in Table 3. A bulk gene expression signature can also be deconvolved into signatures indicative of specific immune cell types using published algorithms, such as the CIBERSORT algorithm described in Gentles et al, Nature Medicine 21:938 2015. Mouse models of cancer that express fluorescent reporters in immune cells can also be used for live imaging-based approaches to evaluate the effect of a SERCA pump inhibitor on immune cell migration or recruitment to a tumor. Immune cell recruitment or migration to a tumor can also be assessed by adding a SERCA pump inhibitor to immune cells in vitro (e.g., immune cells obtained from a subject, animal model, repository, or commercial source) and measuring CCR7 to evaluate immune cell migration or recruitment. The effect of a SERCA pump inhibitor can be determined by comparing results from before and after SERCA pump inhibitor administration.

In some embodiments, a SERCA pump inhibitor increases homing or decreases egress of naïve T cells into or out of secondary lymphoid organs prior to inducing immunogenic tumor cell death to generate a better anti-tumor response (e.g., prior to radio- or chemotherapy). In some embodiments, a SERCA pump inhibitor increases homing or decreases egress of immune cells into or out of the tumor microenvironment to turn a "cold tumor" into a "hot tumor" prior to immunotherapy. In some embodiments, a SERCA pump inhibitor increases homing or decreases egress of effector immune cell subsets into or out of the tumor microenvironment to promote anti-tumor immunity. In some embodiments, a SERCA pump inhibitor decreases homing or increases egress of immunosuppressive immune subsets into or out of the tumor microenvironment to promote anti-tumor immunity. In some embodiments, a SERCA pump inhibitor induces or increases the development of HEVs within the tumor microenvironment to increase TIL recruitment. HEVs can be detected using the monoclonal antibody MECA-79. In some embodiments, the SERCA pump inhibitor induces or increases the development of TLOs within the tumor microenvironment to increase TIL recruitment. TLOs can be recognized by their similarity to SLOs, as they exhibit T and B cell compartmentalization, APCs such as DCs and follicular DCs, stromal cells, and a highly organized vascular system of HEVs.

The effect of a SERCA pump inhibitor on NK cell lytic function can be assessed by evaluation of cellular markers on NK cells obtained from a human subject or animal model. A blood sample or tumor biopsy can be collected from a human subject or animal model and NK cells can be evaluated for one or more (e.g., 1, 2, 3 or more) of the markers: CD95L, CSD154, and CD253. NK cell lytic function can also be assessed using the same methods in an in vivo animal model. This assay can also be performed by adding a SERCA pump inhibitor to NK cells in vitro (e.g., NK cells obtained from a subject, animal model, repository, or commercial source) and measuring the aforementioned markers to evaluate NK cell activation. These markers can be assessed using flow cytometry, immunohistochemistry, in situ hybridization, and other assays that allow for measurement of cell surface markers. The effect of a SERCA pump inhibitor can be determined by comparing results from before and after SERCA pump inhibitor administration.

Table 3 lists additional markers and relevant assays that may be used to assess the level, function and/or activity of immune cells in the methods described herein.

TABLE 3

ASSESSMENT OF IMMUNE CELL PHENOTYPES

| IMMUNE CELL | ASSOCIATED CYTOKINES | MARKER | ASSAYS |
|---|---|---|---|
| Th1 helper | IFN-γ<br>IL-2<br>IL-12<br>IL-18<br>IL-27<br>TNFα<br>TNFβ/LTα | CD4<br>CD94<br>CD119<br>(IFNγ R1)<br>CD183<br>(CXCR3)<br>CD186<br>(CXCR6)<br>CD191<br>(CCR1)<br>CD195<br>(CCR5)<br>CD212 (IL-12Rβ1&2)<br>CD254 (RANKL)<br>CD278 (ICOS)<br>IL-18R<br>MRP1<br>NOTCH3<br>TCR<br>TIM3 | ELISPOT<br>In situ hybridization<br>Immunohistochemistry<br>Limiting dilution Analysis<br>Single-cell PCR<br>In vivo capture assay<br>ELISA<br>Flow cytometry |
| Th2 helper | IL-4<br>IL-2<br>IL-6<br>IL-33<br>IL-17E (IL-25)<br>IL-31<br>IL-3<br>IL-10<br>IL-13 | CD4<br>CD30<br>CD119 (IFNγ R1)<br>CD184 (CXCR4)<br>CD185 (CXCR5)<br>CD193 (CCR3)<br>CD194 (CCR4)<br>CD197 (CCR7)<br>CD278 (ICOS)<br>CD294 (CRTh2)<br>CDw198 (CCR8)<br>IL-17RB<br>IL-33Rα (ST2)<br>NOTCH1<br>NOTCH2<br>TCR<br>TIM1 | ELISPOT<br>In situ hybridization<br>Immunohistochemistry<br>Limiting dilution Analysis<br>Single-cell PCR<br>In vivo capture assay<br>ELISA<br>Flow cytometry |

TABLE 3-continued

ASSESSMENT OF IMMUNE CELL PHENOTYPES

| IMMUNE CELL | ASSOCIATED CYTOKINES | MARKER | ASSAYS |
|---|---|---|---|
| Th17 helper | TGFβ1<br>IL-1β<br>IL-6<br>IL-21<br>IL-23<br>IL-17A<br>IL-17F<br>IL-22<br>IL-26<br>GM-CSF<br>MIP-3α<br>TNFα | CD4<br>CD27<br>CD62L<br>CD127<br>(IL-7R)<br>CD161<br>CD184<br>(CXCR4)<br>CD194<br>(CCR4)<br>CD196<br>(CCR6)<br>CD197<br>(CCR7)<br>CD212b1<br>(IL-12Rβ1)<br>CD213a1<br>(IL-13Rα1)<br>CD278<br>(ICOS)<br>IL-1R1<br>IL-21R<br>IL-23R | ELISPOT<br>In situ hybridization<br>Immunohistochemistry<br>Limiting dilution Analysis<br>Single-cell PCR<br>In vivo capture assay<br>ELISA<br>Flow cytometry |
| Treg | TGFβ1<br>IL-2<br>IL-10<br>IL-35 | CD4<br>CD25<br>CD39<br>CD73<br>CD45RO<br>CD121a<br>(IL-1R1)<br>CD121b<br>(IL-1R2)<br>CD127low<br>CD134<br>(OX40)<br>CD137<br>(4-1BB)<br>CD152<br>(CTLA-4)<br>CD357<br>(GITR/<br>AITR)<br>Foxp3<br>FR4 (m)<br>GARP<br>(activated)<br>Helios<br>LAP/TGFβ<br>(activated)<br>TIGIT | ELISPOT<br>In situ hybridization<br>Immunohistochemistry<br>Limiting dilution Analysis<br>Single-cell PCR<br>In vivo capture assay<br>ELISA<br>Flow cytometry |
| Dendritic cell | GM-CSF<br>IFNγ<br>IL-4<br>GM-CSF<br>IFNα<br>IL-1α<br>IL-1α<br>IL-6<br>IL-8<br>IL-10<br>IL-12<br>IL-15<br>IL-18<br>IL-23<br>IL-27<br>IP-10<br>M-CSF<br>RANTES<br>(CCL5)<br>TGFβ<br>TNFα | CD1a<br>CD8<br>CD11c<br>CD80<br>CD83<br>CD85 (ILT)<br>family<br>CD86<br>CD141 (h)<br>CD169<br>CD172<br>CD184<br>(CXCR4)<br>CD197<br>(CCR7)<br>CD205<br>CD206<br>CD207<br>CD209<br>CD215<br>(IL-15R)<br>CD282<br>(TLR2)<br>CD284<br>(TLR4)<br>CD286<br>(TLR6)<br>Clec Family | ELISPOT<br>In situ hybridization<br>Immunohistochemistry<br>Limiting dilution Analysis<br>Single-cell PCR<br>In vivo capture assay<br>ELISA<br>Flow cytometry |
| Macrophages/ Monocytes | FLT3 Ligand<br>GM-CSF<br>M-CSF<br>CXCL9<br>CXCL10<br>CXCL11<br>G-CSF<br>GM-CSF<br>IFNβ<br>IL-1α<br>IL-1β<br>IL-6<br>IL-8<br>IL-10<br>IL-12p40 & p70<br>IL-18<br>IL-23<br>IL-27<br>M-CSF<br>MIP-2α<br>(CXCL2)<br>RANTES<br>(CCL5)<br>TNFα | CD11b<br>CD14 (mono)<br>CD16<br>CD32<br>CD68<br>CD85a<br>(ILT5)<br>CD163<br>CD169<br>CD195<br>(CCR5)<br>CD204<br>CD206<br>CD282<br>(TLR2)<br>CD284<br>(TLR4)<br>CD286<br>(TLR6)<br>CD354<br>(Trem-1)<br>Clec Family<br>F4/80 (m)<br>HLA-DR | ELISPOT<br>In situ hybridization<br>Immunohistochemistry<br>Limiting dilution Analysis<br>Single-cell PCR<br>In vivo capture assay<br>ELISA<br>Flow cytometry |
| Natural Killer Cell | IL-2<br>IL-12<br>IL-15/<br>IL-15R<br>IL-18<br>Granzyme B<br>IL-17A<br>IL-22<br>MIP-1α<br>(CCL3)<br>MIP-1β<br>(CCL4)<br>Perforin<br>RANTES<br>(CCL5)<br>TNFα | CD16<br>CD25<br>CD49b<br>CD56 (h)<br>CD94<br>CD158<br>family<br>(KIR) (h)<br>CD181<br>(CXCR1)<br>CD183<br>(CXCR3)<br>CD184<br>(CXCR4)<br>CD186<br>(CXCR6)<br>CD192<br>(activated)<br>CD195<br>(CCR5)<br>CD197<br>(CCR7)<br>CD212<br>(IL-12R)<br>CD244<br>CD314<br>(NKG2D)<br>CX3CR1<br>Eomes<br>KLRG1<br>Ly49<br>family (m)<br>NK1.1<br>NKG2A<br>NKp30,<br>NKp42<br>NKp44 (h)<br>NKp46<br>T-bet | ELISPOT<br>In situ hybridization<br>Immunohistochemistry<br>Limiting dilution Analysis<br>Single-cell PCR<br>In vivo capture assay<br>ELISA<br>Flow cytometry |
| Innate Lymphoid Cell 1 (ILC1) | IFN-γ<br>TNF | CD335<br>(NKp46)<br>CD336<br>(NKp44)<br>CD94 | ELISPOT<br>In situ hybridization<br>Immunohistochemistry<br>Limiting dilution Analysis<br>Single-cell PCR |

TABLE 3-continued

ASSESSMENT OF IMMUNE CELL PHENOTYPES

| IMMUNE CELL | ASSOCIATED CYTOKINES | MARKER | ASSAYS |
|---|---|---|---|
| Innate Lymphoid Cell 2 (ILC2) | Areg IL-5 IL-13 | CD56 (NCAM) CD103 T-bet CD127 CRTH2 ST2 (IL-33R) RORα GATA3 | In vivo capture assay ELISA Flow cytometry ELISPOT In situ hybridization Immunohistochemistry Limiting dilution Analysis Single-cell PCR |
| Innate Lymphoid Cell 3 (ILC3) | CCL3 LTs IL-22 IL-17 IFN-γ | CD127 CD117 (c-kit) CD335 (NKp46) CD336 (NKp44) IL-23R RORγt | In vivo capture assay ELISA Flow cytometry ELISPOT In situ hybridization Immunohistochemistry Limiting dilution Analysis Single-cell PCR In vivo capture assay ELISA Flow cytometry |
| Activated B cell/Plasma cells | Antibodies IgM IgG IgD IgE IgA | CD19 CD25 CD30 IgM CD19 IgG CD27 CD38 CD78 CD138 CD319 | Flow cytometry |

TABLE 4

EXAMPLES OF HUMAN CHEMOKINES

| Systematic name | Human gene | Alternate human names | Expression | Human receptor(s) and their expression | Known functions |
|---|---|---|---|---|---|
| *C Family* | | | | | |
| XCL1 | XCL1 | Lymphotactin, SCM-1 alpha, ATAC | activated CD8+ T cells and other MHCI restricted T cells | XCRI: cross-presenting drendritic cells | migration and activation of lymphocytes, NK cells |
| XCL2 | XCL2 | SCM-1 beta | expressed in activated T cells | XCR1: cross-presenting drendritic cells | migration and activation of lymphocytes, NK cells |
| *CX3C Family* | | | | | |
| CX3CL1 | CX3CL1 | Fractalkine, Neurotactin, ABCD-3 | brain, heart, lung, kidney, skeletal muscle and testis. Up-regulated in endothelial cells and microglia by inflammation | CX3CR1: lymphocytes, monocytes | migration and adhesion of lymphocytes and monocytes |
| *CC Family* | | | | | |
| CCL1 | CCL1 | I-309 | activated T cells | CCR8: natural killer cells, monocytes and lymphocytes DARC: erytrocytes, endothelial and epithelial cells | migration of monocytes, NK cells, immature B cells and DCs |
| CCL2 | CCL2 | MCP-1, MCAF, HC11 | monocytes, macrophages and dendritic cells, activated NK cells | CCR2: monocytes CCR4: lymphocytes CCR11: unkown D6: lymphocytes, lymphatic endothelial cells, macrophages DARC: erytrocytes, endothelial and epithelial cells | migration of monocytes and basophils |
| CCL3 | CCL3 | MIP-1 alpha, LD78 alpha, GOS19, Pat464 | T cells, B cells, and monocytes after antigen or mitogen stimulation | CCR1: lymphocytes, monocytes, airway smooth muscle cells CCR4: lymphocytes CCR5: T cells, macrophages, dendritic cells, eosinophils and microglia D6: lymphocytes, lymphatic endothelial cells, macrophages | adhesion of lymphocytes |

TABLE 4-continued

EXAMPLES OF HUMAN CHEMOKINES

| Systematic name | Human gene | Alternate human names | Expression | Human receptor(s) and their expression | Known functions |
|---|---|---|---|---|---|
| CCL3L1 | CCL3L1 | LD78 beta | Unknown | CCR1: lymphocytes, monocytes, airway smooth muscle cells<br>CCR3: eosinophils, basophils, Th2 cells, 0D34+ hematopoetic progenitors, keratinocytes, mast cells<br>CCR5: T cells, macrophages, dendritic cells, eosinophils and microglia<br>D6: lymphocytes, lymphatic endothelial cells, macrophages | migration of lymphocytes and monocytes |
| CCL3L3 | CCL3L3 | LD78 beta | Unknown | CCR1: lymphocytes, monocytes, airway smooth muscle cells<br>CCR3: eosinophils, basophils, Th2 cells, CD34+ hematopoetic progenitors, keratinocytes, mast cells<br>CCR5: T cells, macrophages, dendritic cells, eosinophils and microglia | migration of lymphocytes and monocytes |
| CCL4 | CCL4 | MIP-1 beta, AT744.1, ACT-2, G-26, HC21, H400, MAD-5, LAG-1 | macrophages, dendritic cells | CCR1: lymphocytes, monocytes, airway smooth muscle cells<br>CCR5: T cells, macrophages,dendritic cells, eosinophils and microglia<br>CCR8: natural killer cells, monocytes and lymphocytes<br>D6: lymphocytes, lymphatic endothelial cells, macrophages | migration and adhesion of lymphocytes, regulatory T cells, NK cells, monocyrtes |
| CCL4L1 | CCL4L1 | AT744.2 | macrophages, dendritic cells | CCR1: lymphocytes, monocytes, airway smooth muscle cells<br>CCR5: T cells, macrophages, dendritic cells, eosinophils and microglia | CCR1 and CCR5 expressing cells |
| CCL4L2 | CCL4L2 | | macrophages, dendritic cells | CCR1: lymphocytes, monocytes, airway smooth muscle cells<br>CCR5: T cells, macrophages, dendritic cells, eosinophils and microglia | CCR1 and CCR5 expressing cells |
| CCL5 | CCL5 | RANTES | T cells, macrophages, platelets, synovial fibroblasts, tubular epithelium, certain types of tumor cells | CCR1: lymphocytes, monocytes, airway smooth muscle cells<br>CCR3: eosinophils, basophils, Th2 cells, CD34+ hematopoetic progenitors, keratinocytes, mast cells<br>CCR4: lymphocytes<br>CCR5: T cells, macrophages, dendritic cells, eosinophils and microglia<br>D6: lymphocytes, lymphatic endothelial cells, macrophages<br>DARC: erytrocytes, endothelial and epithelial cells | migration of monocytes, memory T helper cells and eosinophils, causes the release of histamine from basophils and activates eosinophils |

TABLE 4-continued

EXAMPLES OF HUMAN CHEMOKINES

| Systematic name | Human gene | Alternate human names | Expression | Human receptor(s) and their expression | Known functions |
|---|---|---|---|---|---|
| CCL7 | CCL7 | MCP-3 | macrophages, certain types of tumor cells | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>D6: lymphocytes, lymphatic endothelial cells, macrophages<br>DARC: erytrocytes, endothelial and epithelial cells | migration of monocytes, activation of macrophages |
| CCL8 | CCL8 | MCP-2, HC14 | fibroblasts, endothelial cells | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>CCR5: T cells, macrophages, dendritic cells, eosinophils and microglia<br>CCR11: unkown<br>D6: lymphocytes, lymphatic endothelial cells, macrophages<br>DARC: erytrocytes, endothelial and epithelial cells | migration of monocytes, lymphocytes, basophils and eosinophils |
| CCL11 | CCL11 | Eotaxin | lung epithelial cells, pleural mesothelial cells, bronchial airway epithelial cells, smooth muscle cells | CCR3: eosinophils, basophils, Th2 cells, CD34+ hematopoetic progenitors, keratinocytes, mast cells<br>CCR5: T cells, macrophages, dendritic cells, eosinophils and microglia<br>D6: lymphocytes, lymphatic endothelial cells, macrophages<br>DARC: erytrocytes, endothelial and epithelial cells | migration and activation of inflammatory leukocytes, particularly eosinophils |
| CCL12 | | | stromal cells in lung and secondary lymphoid organs | CCR2: monocytes | migration and activation of monocytes |
| CCL13 | CCL13 | MCP-4, CK beta 10, NCC-1 | synovial fibroblasts, chondrocytes | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>CCR5: T cells, macrophages, dendritic cells, eosinophils and microglia<br>CCR11: unkown<br>D6: lymphocytes, lymphatic endothelial cells, macrophages<br>DARC: erytrocytes, endothelial and epithelial cells | migration of eosinophils, monocytes and T lymphocytes |

TABLE 4-continued

EXAMPLES OF HUMAN CHEMOKINES

| Systematic name | Human gene | Alternate human names | Expression | Human receptor(s) and their expression | Known functions |
|---|---|---|---|---|---|
| CCL14 | CCL14 | HCC-1, MCIF, CK beta 1, NCC-2 | spleen, bone marrow, liver, muscle and gut | CCR1: lymphocytes, monocytes, airway smooth muscle cells<br>CCR3: eosinophils, basophils, Th2 cells, 0D34+ hematopoetic progenitors, keratinocytes, mast cells<br>CCR5: T cells, macrophages, dendritic cells, eosinophils and microglia<br>D6: lymphocytes, lymphatic endothelial cells, macrophages<br>DARC: erytrocytes, endothelial and epithelial cells | activation of monocytes |
| CCL15 | CCL15 | MIP-1 delta, LKN-1, HCC-2, MIP-5, NCC-3 | airway smooth muscle cells, lung leukocytes, alveolar macrophages, basophils | CCR1: lymphocytes, monocytes, airway smooth muscle cells<br>CCR3: eosinophils, basophils, Th2 cells, CD34+ hematopoetic progenitors, keratinocytes, mast cells | migration of monocytes and eosinophils, proliferation of CD34 myeloid progenitor cells |
| CCL16 | CCL16 | HCC-4, LEC, ILINCK, NCC-4, LMC, CK beta 12 | liver, thymus, and spleen | CCR1: lymphocytes, monocytes, airway smooth muscle cells<br>CCR2: monocytes<br>CCR5: T cells, macrophages, dendritic cells, eosinophils and microglia<br>CCR8: natural killer cells, monocytes and lymphocytes<br>DARC: erytrocytes, endothelial and epithelial cells<br>H4: bone marrow, eosinophils, T-cells, dendritic cells, monocytes, mast cells, neutrophil | migration of lymphocytes and monocytes |
| CCL17 | CCL17 | TARC, ABCD-2 | constitutively expressed in thymus, dendritic cells, keratinocytes | CCR4: lymphocytes<br>CCR8: natural killer cells, monocytes and lymphocytes<br>D6: lymphocytes, lymphatic endothelial cells, macrophages<br>DARC: erytrocytes, endothelial and epithelial cells | Migration and activation of T cells |
| CCL18 | CCL18 | PARC, DC-CK1, AMAC-1, CK beta 7, MIP-4 | dendritic cells, monocytes, and macrophages | CCR8: natural killer cells, monocytes and lymphocytes<br>PITPNM3: breast cancer cells<br>DARC: erytrocytes, endothelial and epithelial cells | migration of naive and regulatory lymphocytes, dendritic cells |
| CCL19 | CCL19 | MIP-3 beta, ELC, Exodus-3, CK beta 11 | fibroblastic reticular cells, dendritic cells | CCR7: lymphocytes (mainly naive and memory), mature dendritic cells<br>CCR11: unkown<br>CCRL2: neutrophils, monocytes | migration of naive and memory lymphocytes and mature dendritic cells |
| CCL20 | CCL20 | MIP-3 alpha, LARC, Exodus-1, ST38, CK beta 4 | epidermis (keratinocytes), lymphocytes | CCR6: immature dendritic cells and memory T cells | migration of lymphocytes, DCs and neutrophils |

TABLE 4-continued

EXAMPLES OF HUMAN CHEMOKINES

| Systematic name | Human gene | Alternate human names | Expression | Human receptor(s) and their expression | Known functions |
|---|---|---|---|---|---|
| CCL21 | CCL21 | 6Ckine, Exodus-2, SLC, TCA-4, CK beta 9 | Stromal cells, lymphatic endothelial cells, fibroblastic reticular cells, dendritic cells | CCR7: lymphocytes (mainly naive and memory), mature dendritic cells CCR11: unkown | migration of lymphocytes homing to secondary lymphoid organs, induces integrin-mediated lymphocyte adhesion |
| CCL22 | CCL22 | MDC | Macrophages | CCR4: lymphocytes D6: lymphocytes, lymphatic endothelial cells, macrophages | migration of NK cells, chronically activated T cells, monocytes and DCs |
| CCL23 | CCL23 | MPIF-1, CK beta 8, CK beta 8-1, MIP-3 | Monocytes | CCR1: lymphocytes, monocytes FPRL-1: monocytes, mast cells | migration of monocytes, resting T cells and neutrophils |
| CCL24 | CCL24 | Eotaxin-2, MPIF-2, CK beta 6 | lung tissue | CCR3: eosinophils, basophils, Th2 cells, CD34+ hematopoetic progenitors, keratinocytes, mast cells | migration of basophils |
| CCL25 | CCL25 | TECK, CK beta 15 | thymic dendritic cells and mucosal epithelial cells | CCR9: T lymphocytes of small intestine | migration of dendritic cells, thymocytes and activated macrophages |
| CCL26 | CCL26 | Eotaxin-3, MIP-4 alpha, IMAC, TSC-1 | heart, lung and ovary and in endothelial cells stimulated with IL4 | CCR3: eosinophils, basophils, Th2 cells, CD34+ hematopoetic progenitors, keratinocytes, mast cells CX3CR1: lymphocytes, monocytes | migration of eosinophils and basophils |
| CCL27 | CCL27 | CTACK, ILC, PESKY, ESKINE | Keratinocytes | CCR10: melanocytes, plasma cells and skin-homing T cells | migration of memory T cells |
| CCL28 | CCL28 | MEC | columnar epithelial cells in the gut, lung, breast and the salivary glands | CCR3: eosinophils, basophils, Th2 T cells, CD34+ hematopoetic progenitors, keratinocytes, mast cells CCR10: melanocytes, plasma cells and skin homing T cells | migration of lymphocytes and eosinophils |
| CXC Family | | | | | |
| CXCL1 | CXCL1 | GRO alpha, MGSA, GRO1, NAP-3 | mammary, fibroblasts, mammary epithelial cells, endothelial cells, activated, monocytes, macrophages and neutrophils | CXCR2 (IL8RB): neutrophils DARC: erytrocytes, endothelial and epithelial cells | migration of neutrophils |
| CXCL2 | CXCL2 | GRO beta, MIP-2 alpha, GRO2 | monocytes, macrophages | CXCR2 (IL8RB): neutrophils DARC: erytrocytes, endothelial and epithelial cells | migration and activation of neutrophils, basophils, hematopoietic stem cells |
| CXCL3 | CXCL3 | GRO gamma, MIP-2 beta, GRO3 | smooth muscle cells, epithelial cells | CXCR2 (IL8RB): neutrophils DARC: erytrocytes, endothelial and epithelial cells | migration and activation of neutrophils |
| CXCL4 | PF4 | PF4 | activated platelets, megakaryocytes, leukocytes, endothelial cells | CXCR3 (CD183b): T cells, NK cells CXCR3-B: T cells, NK cells | migration of neutrophils and fibroblasts, inhibiting |

TABLE 4-continued

EXAMPLES OF HUMAN CHEMOKINES

| Systematic name | Human gene | Alternate human names | Expression | Human receptor(s) and their expression | Known functions |
|---|---|---|---|---|---|
| CXCL4L1 | PF4V1 | PF4V1 | smooth muscle cells, T cells, and platelets | DARC: erytrocytes, endothelial and epithelial cells<br>CXCR3 (CD183b): T cells, NK cells<br>CXCR3-B: T cells, NK cells | endothelial cell proliferation and chemotaxis inhibiting endothelial cell proliferation and chemotaxis |
| CXCL5 | CXCL5 | ENA-78 | fibroblasts, epithelial cells, eosinophils | CXCR2 (IL8RB): neutrophils<br>DARC: erytrocytes, endothelial and epithelial cells | migration and activation of neutrophils |
| CXCL6 | CXCL6 | GCP-2 | fibroblasts, epithelial cells | CXCR1 (IL8RA): neutrophils<br>CXCR2 (IL8RB): neutrophils<br>DARC: erytrocytes, endothelial and epithelial cells | migration of neutrophils |
| CXCL7 | PPBP | NAP-2, CTAPIII, beta-TG | activated platelets | CXCR1 (IL8RA): neutrophils<br>CXCR2 (IL8RB): neutrophils | migration of neutrophils |
| CXCL8 | IL8 | IL-8, NAP-1, MDNCF, GCP-1 | macrophages, epithelial cells, airway smooth muscle cells, endothelial cells | CXCR1 (IL8RA): neutrophils<br>CXCR2 (IL8RB): neutrophils<br>DARC: erytrocytes, endothelial and epithelial cells | migration of neutrophils, basophils, and T-cells, and angiogenic factor |
| CXCL9 | CXCL9 | MIG, CRG-10 | monocytes, macrophages and endothelial cells | CXCR3 (CD183b): T cells, NK cells<br>CXCR3-B: T cells, NK cells<br>DARC: erytrocytes, endothelial and epithelial cells | migration of Th1 lymphocytes, angiogenic factor |
| CXCL10 | CXCL10 | IP-10 | neutrophils, hepatocytes, endothelial cells and keratinocytes | CXCR3 (CD183b): T cells, NK cells<br>CXCR3-B: T cells, NK cells<br>DARC: erytrocytes, endothelial and epithelial cells | migration of CD4+ T cells |
| CXCL11 | CXCL11 | I-TAC, beta-R1, H174, IP-9 | peripheral blood leukocytes, pancreas and liver astrocytes and at moderate levels in thymus, spleen and lung | CXCR3 (CD183b): T cells, NK cells<br>CXCR7 (ACKR3): tumor cells and tumor-associated blood endothelium<br>DARC: erytrocytes, endothelial and epithelial cells | migration of interleukin-activated T cells but not unstimulated T cells, neutrophils or monocytes. |
| CXCL12 | CXCL12 | SDF-1, PBSF | ubiquitously expressed in many tissues and cell types | CXCR4: brain, heart, lymphocytes, HSCs, blood endothelial cells and umbilical cord endothelial cell<br>CXCR7 (ACKR3): tumor cells and tumor-associated blood endothelium | migration of lymphocytes and hepatopoietic stem cells, angiogenic factor |
| CXCL13 | CXCL13 | BCA-1, BLC | follicles of the spleen, lymph nodes, and Peyer's patches | CXCR3 (CD183b): T cells, NK cells<br>CXCR5: Burkitt's lymphoma, lymph node follicules, spleen<br>DARC: erytrocytes, endothelial and epithelial cells | migration of B cells |
| CXCL14 | CXCL14 | BRAK, BMAC | Fibroblasts | unknown | migration of monocytes, NK cells, DCs |
| CXCL16 | CXCL16 | SR-PSOX | DCs | CXCR6: T cells | migration of several subsets |

TABLE 4-continued

EXAMPLES OF HUMAN CHEMOKINES

| Systematic name | Human gene | Alternate human names | Expression | Human receptor(s) and their expression | Known functions |
|---|---|---|---|---|---|
| CXCL17 | CXCL17 | DMC, VCC-1 | Lung and tumor tissue | unknown | of T cells and NKT cells migration of DCs and monocytes |

TABLE 5

EXAMPLES OF HUMAN IMMUNE CELL TRAFFICKING MOLECULES

| Trafficking molecule | Trafficking molecule expressing or presenting cells | Leukocyte ligand | Function in the extravasation cascade |
|---|---|---|---|
| P-selectin | Blood endothelial cell | PSGL-1, L-selectin, CD44 | Tethering/Rolling during extravasation cascade |
| E-selectin | Blood endothelial cell | Glycoprotein, glycolipid, PSGL-1 | Tethering/Rolling during extravasation cascade |
| PNAd | Blood endothelial cell | L-selectin | Tethering/Rolling during extravasation cascade |
| MAdCAM | Blood endothelial cell | L-selectin, integrins | Tethering/Rolling, arrest during extravasation cascade |
| VCAM-1 | Blood endothelial cell | Integrins (e.g. VLA-4) | Tethering/Rolling, arrest during extravasation cascade |
| Chemokines | Blood endothelial cell | GPCRs | Integrin activation, allowing binding of cell adhesion molecules and arrest |
| ICAM-1 | Blood endothelial cell | Integrins (e.g. LFA-1, Mac-1) | Arrest during extravasation cascade |
| ICAM-2 | Blood endothelial cell | Integrins (e.g. LFA-1, Mac-1) | Arrest during extravasation cascade |
| PECAM1 (CD31) | Blood endothelial cell | Integrins (e.g. alpha v beta 3), PECAM1 | Transmigration |
| JAM-A/-B/-C | Blood endothelial cell | Integrins (e.g. LFA-1, Mac-1, VLA-4) | Transmigration |
| ESAM | Blood endothelial cell | unknown | Transmigration |
| CD99 | Blood endothelial cell | CD99 | Transmigration |
| CD99L2 | Blood endothelial cell | possibly CD99L | Transmigration |
| VE-cadherin | Blood endothelial cell | None | Transmigration |
| PVR | Blood endothelial cell | DNAM1 | Transmigration |
| S1P | Lymphatic endothelial cell | S1P receptor 1 (S1P1) | Entry into afferent and efferent lymphatics (in peripheral or SLOs respectively) |

Cancer

The methods described herein can be used to treat cancer in a subject by administering to the subject an effective amount of a SERCA pump inhibitor, e.g., a SERCA pump inhibitor described herein. The method may include administering locally (e.g., intratumorally) to the subject a SERCA pump inhibitor described herein in a dose (e.g., effective amount) and for a time sufficient to treat the cancer.

The methods described herein can also be used to potentiate or increase an immune response in a subject in need thereof, e.g., an anti-tumor immune response. For example, the subject has cancer, such as a cancer described herein. The methods described herein can also include a step of selecting a subject in need of potentiating an immune response, e.g., selecting a subject who has cancer or is at risk of developing cancer.

The SERCA pump inhibitor may inhibit proliferation or disrupt the function of non-neural cells that promote cancer growth that are associated with the cancer, e.g., the method includes administering to the subject an effective amount of a SERCA pump inhibitor for a time sufficient to inhibit proliferation or disrupt the function of non-neural cells that promote cancer growth that are associated with the cancer. Non-neural cells that promote cancer growth that are associated with the cancer include malignant cancer cells, malignant cancer cells in necrotic and hypoxic areas, M2 macrophages, tumor associated macrophages, T regulatory cells, myeloid derived suppressor cells, adipocytes, B10 cells, Breg cells, endothelial cells, cancer associated fibroblasts, fibroblasts, mesenchymal stem cells, red blood cells, or extracellular matrix. The proliferation of non-neural cells that promote cancer growth that are associated with the cancer may be decreased in the subject at least 1%, 2%, 5%, 10%, 15%, 20%, 25%, 30%, 35%, 40%, 50%, 60%, 70%, 80%, 90%, 95% or more, compared to before the administration. The proliferation of non-neural cells that promote cancer growth that are associated with the cancer can be decreased in the subject between 5-20%, between 5-50%, between 10-50%, between 20-80%, between 20-70%.

The SERCA pump inhibitor may promote proliferation or enhance the function of non-neural cells that disrupt cancer growth that are associated with the cancer, e.g., the method includes administering to the subject an effective amount of a SERCA pump inhibitor for a time sufficient to promote proliferation or enhance the function of non-neural cells that disrupt cancer growth that are associated with the cancer. Non-neural cells that disrupt cancer growth that are associated with the cancer include NK cells, NKT cells, M1 macrophages, TH1 helper cells, TH2 helper cells, CD8 cytotoxic T cells, TH17 cells, tumor associated neutrophils, terminally differentiated myeloid dendritic cells, T lymphocytes, B lymphocytes, lymphatic endothelial cells, pericytes, dendritic cells, mesenchymal stem cells, red blood cells, or extracellular matrix. The proliferation of non-neural cells that disrupt cancer growth that are associated with the cancer may be increased in the subject at least 1%, 2%, 5%, 10%, 15%, 20%, 25%, 30%, 35%, 40%, 50%, 60%, 70%, 80%, 90%, 95% or more, compared to before the administration. The proliferation of non-neural cells that disrupt cancer growth that are associated with the cancer can be increased in the subject between 5-20%, between 5-50%, between 10-50%, between 20-80%, between 20-70%.

The SERCA pump inhibitor can be administered in an amount sufficient to treat cancer. For example, the stroma associated with the tumor, e.g., fibroblasts, is disrupted such that an essential function, e.g., the production of matrix metalloproteases, is altered to inhibit tumor survival or promote tumor control.

The SERCA pump inhibitor can have one or more of the following activities: (a) inhibits an immune checkpoint, (b) activates anti-tumor immune response, (c) activate tumor-specific T cells from draining lymph nodes, and/or (d) stimulates a neoantigen-specific immune response. The activity can be modulated as appropriate in the subject (e.g., a human subject or animal model) at least 1%, 2%, 5%, 10%, 15%, 20%, 25%, 30%, 35%, 40%, 50%, 60%, 70%, 80%, 90%, 95% or more, compared to before the administration. The activity can be modulated as appropriate in the subject between 5-20%, between 5-50%, between 10-50%, between 20-80%, between 20-70%.

The SERCA pump inhibitor can treat cancer by increasing cancer cell death in a subject (e.g., a human subject or animal model) or in a cancer cell culture (e.g., a culture generated from a patient tumor sample, a cancer cell line, or a repository of patient samples). A SERCA pump inhibitor can increase cancer cell death by at least 1%, 2%, 5%, 10%, 15%, 20%, 25%, 30%, 35%, 40%, 50%, 60%, 70%, 80%, 90%, 95% or more compared to before administration to a subject or cancer cell culture. A SERCA pump inhibitor can increase cancer cell death in a subject or cancer cell culture between 5-20%, between 5-50%, between 10-50%, between 20-80%, between 20-70%.

The SERCA pump inhibitor can also act to inhibit cancer cell growth, proliferation, metastasis, migration, or invasion, e.g., the method includes administering to the subject (e.g., a human subject or animal model) or a cancer cell culture (e.g., a culture generated from a patient tumor sample, a cancer cell line, or a repository of patient samples) a SERCA pump inhibitor in an amount (e.g., an effective amount) and for a time sufficient to inhibit cancer cell growth, proliferation, metastasis, migration, or invasion. Cancer cell growth, proliferation, metastasis, migration, or invasion can be decreased in the subject or cancer cell culture at least 1%, 2%, 5%, 10%, 15%, 20%, 25%, 30%, 35%, 40%, 50%, 60%, 70%, 80%, 90%, 95% or more, compared to before the administration Cancer cell growth, proliferation, metastasis, migration, or invasion can be decreased in the subject or cancer cell culture between 5-20%, between 5-50%, between 10-50%, between 20-80%, between 20-70%.

Cancer Types

In the methods described herein, the cancer or neoplasm may be any solid or liquid cancer and includes benign or malignant tumors, and hyperplasias, including gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g., head and neck squamous cell cancer); CNS cancer including malignant glioma, astrocytomas, retinoblastomas and brain metastases; malignant mesothelioma; non-metastatic or metastatic breast cancer (e.g., hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, acute myelogenous leukemia, chronic myelogenous leukemia, myelodysplastic syndrome, acute lymphoblastic leukemia, Hodgkin's lymphoma).

Additional cancers that can be treated according to the methods described herein include breast cancer, lung cancer, stomach cancer, colon cancer, liver cancer, renal cancer, colorectal cancer, prostate cancer, pancreatic cancer, cervical cancer, anal cancer, vulvar cancer, penile cancer, vaginal cancer, testicular cancer, pelvic cancer, thyroid cancer, uterine cancer, rectal cancer, brain cancer, head and neck cancer, esophageal cancer, bronchus cancer, gallbladder cancer, ovarian cancer, bladder cancer, oral cancer, oropharyngeal cancer, larynx cancer, biliary tract cancer, skin cancer, a cancer of the central nervous system, a cancer of the respiratory system, and a cancer of the urinary system. Examples of breast cancers include, but are not limited to, triple-negative breast cancer, triple-positive breast cancer, HER2-negative breast cancer, HER2-positive breast cancer, estrogen receptor-positive breast cancer, estrogen receptor-negative breast cancer, progesterone receptor-positive breast cancer, progesterone receptor-negative breast cancer, ductal carcinoma in situ (DCIS), invasive ductal carcinoma, invasive lobular carcinoma, inflammatory breast cancer, Paget disease of the nipple, and phyllodes tumor.

Other cancers that can be treated according to the methods described herein include leukemia (e.g., B-cell leukemia, T-cell leukemia, acute myeloid leukemia (AML), chronic myeloid leukemia (CML), acute lymphocytic (lymphoblastic) leukemia (ALL), chronic lymphocytic leukemia (CLL), and erythroleukemia), sarcoma (e.g., angiosarcoma, chondrosarcoma, Ewing's sarcoma, fibrosarcoma, gastrointestinal stromal tumor, leiomyosarcoma, liposarcoma, malignant peripheral nerve sheath tumor, malignant fibrous cytoma, osteosarcoma, pleomorphic sarcoma, rhabdomyosarcoma, synovial sarcoma, vascular sarcoma, Kaposi's sarcoma, dermatofibrosarcoma, epithelioid sarcoma, leyomyosarcoma, and neurofibrosarcoma), carcinoma (e.g., basal cell carcinoma, large cell carcinoma, small cell carcinoma, non-small cell lung carcinoma, renal carcinoma, hepatocarcinoma, gastric carcinoma, choriocarcinoma, adenocarcinoma, hepatocellular carcinoma, giant (or oat) cell carcinoma, squamous cell carcinoma, adenosquamous carcinoma, anaplastmic carcinoma, adrenocortical carcinoma, cholangiocarcinoma, Merkel cell carcinoma, ductal carcinoma in situ (DCIS), and invasive ductal carcinoma), blastoma (e.g., hepatoblastoma, medulloblastoma, nephroblastoma, neuroblastoma, pancreatoblastoma, pleuropulmonary blastoma, retinoblastoma, and glioblastoma multiforme), lymphoma (e.g., Hodgkin's lymphoma, non-Hodgkin's lymphoma, and Burkitt lymphoma), myeloma (e.g., multiple myeloma, plasmacytoma, localized myeloma, and extramedullary myeloma), melanoma (e.g., superficial spreading melanoma, nodular melanoma, lentigno maligna melanoma, acral lentiginous melanoma, and amelanotic melanoma), neuroma (e.g., ganglioneuroma, Pacinian neuroma, and acoustic neuroma), glioma (e.g., astrocytoma, oligoastrocytoma, ependymoma, brainstem glioma, optic nerve glioma, and oligoastrocytoma), pheochromocytoma, meningioma, malignant mesothelioma, and virally induced cancer.

In some embodiments, the cancer is a paraneoplastic cancer (e.g., a cancer that causes a paraneoplastic syndrome). Paraneoplastic syndromes are rare disorders that are triggered by an altered immune system response to a neoplasm, and are mediated by humoral factors such as hormones, cytokines, or auto-antibodies produced by the tumor. Symptoms of paraneoplastic syndrome may be endocrine, neuromuscular, or musculoskeletal, cardiovascular, cutaneous, hematologic, gastrointestinal, renal, or neurological. Paraneoplastic syndromes commonly present with lung, breast, and ovarian cancer and cancer of the lymphatic system (e.g., lymphoma). Paraneoplastic neurological disorders are disorders that affect the central or peripheral nervous system, and can include symptoms such as ataxia (difficulty with walking and balance), dizziness, nystagmus (rapid uncontrolled eye movements), difficulty swallowing, loss of muscle tone, loss of fine motor coordination, slurred speech memory loss, vision problems, sleep disturbances, dementia, seizures, or sensory loss in the limbs. Breast, ovarian, and lung cancers are most commonly associated with paraneoplastic neurological disorders. Other common types of paraneoplastic syndromes include paraneoplastic cerebellar degeneration, paraneoplastic pemphigus, paraneoplastic autonomic neuropathy, paraneoplastic encephalomyelitis, and cancer-associated autoimmune retinopathy.

Endocrine paraneoplastic syndromes include Cushing syndrome (caused by ectopic ACTH), which is most commonly caused by small cell lung cancer, pancreatic carcinoma, neural tumors, or thymoma; SIADH (caused by antidiuretic hormone), which is most commonly caused by small cell lung cancer and CNS malignancies; hypercalcemia (caused by PTHrp, TGFα, TNF, or IL-1), which is most commonly caused by lung cancer, breast carcinoma, renal and bladder carcinoma, multiple myeloma, adult T cell leukemia/lymphoma, ovarian carcinoma, and squamous cell carcinoma (e.g., lung, head, neck, or esophagus carcinoma); hyperglycemia (caused by insulin insulin-like substance, or "big" IGF-II), which is most commonly caused by fibrosarcoma, mesenchymal sarcomas, insulinoma, and hepatocellular carcinoma; carcinoid syndrome (caused by serotonin or bradykinin), which is most commonly caused by bronchial adenoma, pancreatic carcinoma, and gastric carcinoma; and hyperaldosteronism (caused by aldosterone), which is most commonly caused by adrenal adenoma/Conn's syndrome, non-Hodgkin's lymphoma, ovarian carcinoma, and pulmonary cancer.

Neurological paraneoplastic syndromes include Lambert-Eaton myasthenic syndrome (LEMS), which is most commonly caused by small cell lung cancer; paraneoplastic cerebellar degeneration, which is most commonly caused by lung cancer, ovarian cancer, breast carcinoma, and Hodgkin's lymphoma; encephalomyelitis; limbic encephalitis, which is most commonly caused by small cell lung carcinoma; myasthenia gravis, which is most commonly caused by thymoma; brainstem encephalitis; opsoclonus myoclonus ataxia (caused by autoimmune reaction against Nova-1), which is most commonly caused by breast carcinoma, ovarian carcinoma, small cell lung carcinoma, and neuroblastoma; anti-NMDA receptor encephalitis (caused by autoimmune reaction against NMDAR subunits), which is most commonly caused by teratoma; and polymyositis, which is most commonly caused by lung cancer, bladder cancer, and non-Hodgkin's lymphoma. Mucotaneous paraneoplastic syndromes include acanthosis nigricans, which is most commonly caused by gastric carcinoma, lung carcinoma, and uterine carcinoma; dermatomyositis, which is most commonly caused by bronchogenic carcinoma, breast carcinoma, ovarian cancer, pancreatic cancer, stomach cancer, colorectal cancer, and Non-Hodgkin's lymphoma; Leser-Trelat sign; necrolytic migratory erythema, which is most commonly caused by glucoganoma; Sweet's syndrome; florid cutaneous papillomatosis; pyoderma gangrenosum; and acquired generalized hypertrichosis.

Hematological syndromes include granulocytosis (caused by G-CSF); polycythemia (caused by erythropoietin), which is commonly caused by renal carcinoma, cerebellar hemangioma, and heptatocellular carcinoma; Trousseau sign (caused by mucins), which is commonly caused by pancreatic carcinoma and bronchogenic carcinoma; nonbacterial thrombotic endocarditis, which is caused by advanced cancers; and anemia, which is most commonly caused by thymic neoplasms. Other paraneoplastic syndromes include membranous glomerular nephritis; neoplastic fever; Staffer syndrome, which is caused by renal cell carcinoma; and tumor-induced osteomalacia (caused by FGF23), which is caused by hemangiopericytoma and phosphaturic mesenchymal tumor.

In some embodiments, a subject is identified as having cancer after presenting with symptoms of a paraneoplastic syndrome. A common symptom of paraneoplastic syndrome is fever. Auto-antibodies directed against nervous system proteins are also frequently observed in patients with paraneoplastic syndromes, including anti-Hu, anti-Yo, anti-Ri, anti-amphiphysin, anti-CV2, anti-Ma2, anti-recoverin, anti-transducin, anti-carbonic anhydrase II, anti-arrestin, anti-GCAP1, anti-GCAP2, anti-HSP27, anti-Rab6A, and anti-PNR. Other symptoms that can be used to identify a patient with paraneoplastic cancer include ataxia, dizziness, nystagmus, difficulty swallowing, loss of muscle tone, loss of fine motor coordination, slurred speech memory loss, vision loss, sleep disturbances, dementia, seizures, dysgeusia, cachexia, anemia, itching, or sensory loss in the limbs. In some embodiments, a patient presents with symptoms of paraneoplastic syndrome and is then identified as having cancer based on imaging tests (e.g., CT, MRI, or PET scans).

The cancer may be innervated, metastatic, non-metastatic cancer, or benign (e.g., a benign tumor). The cancer may be a primary tumor or a metastasized tumor.

In some embodiments, the cancer is a SERCA pump-associated cancer (e.g., a cancer associated with expression of one or more SERCA pumps in immune cells, e.g., effector T cells, helper T cells, Th1 cells, Th2 cells, or Th17 cells).

In some embodiments, the cancer is an immune cell-infiltrated cancer (e.g., a T cell infiltrated cancer, or a cancer with myeloid cell tumor infiltrate, e.g., a cancer infiltrated by T cells, macrophages, monocytes, or myeloid derived suppressor cells). The immune cell-infiltrated cancer may be a "hot tumor" that contains T cells and expresses neoantigens. Cancers that are commonly considered "hot" include bladder cancer, head and neck cancer, kidney cancer, liver cancer, melanoma, non-small cell lung cancer, and microsatellite instability high cancer. The immune cell-infiltrated cancer may be a "cold tumor" that contains or is associated with suppressive immune cells, such as myeloid-derived suppressor cells and/or Tregs. Cancers that are immunologically "cold" typically do not respond to immunotherapy and include ovarian, prostate, and pancreatic cancer. A cancer in a subject can be identified as an immune cell-infiltrated cancer based on a biopsy, which can be evaluated for expression of immune cell markers (e.g., a marker listed in Table 3 and/or a marker described in Danaher et al., J Immunother Cancer 5:18, 2017) using standard methods, such as immunohistochemistry, flow cytometry, and expression profiling (e.g., RNAseq, microarray analysis, or a cancer immune profiling gene expression panel). In some embodiments, the cancer is a cancer that is treated with immunotherapy (e.g., melanoma, non-small cell lung cancer, kidney cancer, renal cell carcinoma, bladder cancer, head and neck cancer, Hodgkin's lymphoma, leukemia, urothelial carcinoma, gastric cancer, microsatellite instability-high cancer, colorectal cancer, or hepatocellular carcinoma). In some embodiments, the cancer is a cancer for which immunotherapy is not effective (e.g., a cancer that cannot be treated using immunotherapy or a cancer that did not respond to treatment with immunotherapy).

Subjects who can be treated with the methods disclosed herein include subjects who have had one or more tumors resected, received chemotherapy or other pharmacological treatment for the cancer, received radiation therapy, and/or received other therapy for the cancer. Subjects who can be treated with the methods disclosed herein include subjects that do not respond to immunotherapy. Subjects who have not previously been treated for cancer can also be treated with the methods disclosed herein.

Combination Therapies

A SERCA pump inhibitor described herein can be administered in combination with a second therapeutic agent for treatment of cancer. In some embodiments, the second therapeutic agent is selected based on tumor type, tumor tissue of origin, tumor stage, or mutations in genes expressed by the tumor.

Checkpoint Inhibitors

One type of agent that can be administered in combination with a SERCA pump inhibitor described herein is a checkpoint inhibitor. Checkpoint inhibitors can be broken down into at least 4 major categories: i) agents such as antibodies that block an inhibitory pathway directly on T cells or NK cells (e.g., PD-1 targeting antibodies such as nivolumab and pembrolizumab, antibodies targeting TIM-3, and antibodies targeting LAG-3, 2B4, CD160, A2aR, BTLA, CGEN-15049, or KIR), ii) agents such as antibodies that activate stimulatory pathways directly on T cells or NK cells (e.g., antibodies targeting OX40, GITR, or 4-1 BB), iii) agents such as antibodies that block a suppressive pathway on immune cells or rely on antibody-dependent cellular cytotoxicity to deplete suppressive populations of immune cells (e.g., CTLA-4 targeting antibodies such as ipilimumab, antibodies targeting VISTA, and antibodies targeting PD-L2, Gr1, or Ly6G), and iv) agents such as antibodies that block a suppressive pathway directly on cancer cells or that rely on antibody-dependent cellular cytotoxicity to enhance cytotoxicity to cancer cells (e.g., rituximab, antibodies targeting PD-L1, and antibodies targeting B7-H3, B7-H4, Gal-9, or MUC1). Such agents described herein can be designed and produced, e.g., by conventional methods known in the art (e.g., Templeton, Gene and Cell Therapy, 2015; Green and Sambrook, Molecular Cloning, 2012).

Chemotherapy

A second type of therapeutic agent that can be administered in combination with a SERCA pump inhibitor described herein is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyllotoxins, antibiotics, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel; chloranbucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; tenoposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art.

Biologic Cancer Agents

Another type of therapeutic agent that can be administered in combination with a SERCA pump inhibitor described herein is a therapeutic agent that is a biologic such a cytokine (e.g., interferon or an interleukin (e.g., IL-2)) used in cancer treatment. In other embodiments the biologic is an anti-angiogenic agent, such as an anti-VEGF agent, e.g., bevacizumab. In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituximab; Dacliximab; Basiliximab; Palivizumab; Infliximab; Trastuzumab; Gemtuzumab ozogamicin; Alemtuzumab; Ibritumomab tiuxetan; Adalimumab; Omalizumab; Tositumomab-I-131; Efalizumab; Cetuximab; Bevacizumab; Natalizumab; Tocilizumab; Panitumumab; Ranibizumab; Eculizumab; Certolizumab pegol; Golimumab; Canakinumab; Ustekinumab; Ofatumumab; Denosumab; Motavizumab; Raxibacumab; Belimumab; Ipilimumab; Brentuximab Vedotin; Pertuzumab; Ado-trastuzumab emtansine; and Obinutuzumab. Also included are antibody-drug conjugates. Examples of biologic cancer agents that can be used in combination with SERCA pump inhibitors described herein are shown in Table 6 below.

TABLE 6

APPROVED CANCER ANTIBODIES

| Antibody | Company | Antigen | Indication |
| --- | --- | --- | --- |
| ado-trastuzumab emtansine | Genentech | HER2 | Metastatic breast cancer |
| alemtuzumab | Genzyme | CD52 | B-cell chronic lymphocytic leukemia |
| atezolizumab | Genentech | PD-L1 | Urothelial carcinoma |
|  |  |  | Metastatic non-small cell lung cancer |
| avelumab | EMD Serono | PD-L1 | Metastatic Merkel cell carcinoma |
| bevacizumab | Genentech | VEGF | Metastatic colorectal cancer |
| blinatumomab | Amgen | CD19 | Precursor B-cell acute lymphoblastic leukemia |
| brentuximab vedotin | Seattle Genetics | CD30 | Hodgkin lymphoma |
|  |  |  | Anaplastic large-cell lymphoma |
| cetuximab | ImClone Systems | EGFR | Metastatic colorectal carcinoma |
| daratumumab | Janssen Biotech | CD38 | Multiple myeloma |
| dinutuximab | United Therapeutics | GD2 | Pediatric high-risk neuroblastoma |
| durvalumab | AstraZeneca | PD-L1 | Urothelial carcinoma |
| elotuzumab | Bristol-Myers Squibb | SLAMF7 | Multiple myeloma |
| ibritumomab tiuxetan | Spectrum Pharmaceuticals | CD20 | Relapsed or refractory low-grade, follicular, or transformed B-cell non-Hodgkin's lymphoma |
| ipilimumab | Bristol-Myers Squibb | CTLA-4 | Metastatic melanoma |
| necitumumab | Eli Lilly | EGFR | Metastatic squamous non-small cell lung carcinoma |
| nivolumab | Bristol-Myers Squibb | PD-1 | Metastatic melanoma |
|  |  |  | Metastatic squamous non-small cell lung carcinoma |
| obinutuzumab | Genentech | CD20 | Chronic lymphocytic leukemia |
| ofatumumab | Glaxo Grp | CD20 | Chronic lymphocytic leukemia |
| olaratumab | Eli Lilly | PDGFRA | Soft tissue sarcoma |
| panitumumab | Amgen | EGFR | Metastatic colorectal cancer |
| pembrolizumab | Merck | PD-1 | Metastatic melanoma |
| pertuzumab | Genentech | HER2 | Metastatic breast cancer |
| ramucirumab | Eli Lilly | VEGFR2 | Gastric cancer |
| rituximab | Genentech | CD20 | B-cell non-Hodgkin's lymphoma |
| trastuzumab | Genentech | HER2 | Metastatic breast cancer |

Cancer-Specific Agents

In some embodiments, the therapeutic agents administered with the SERCA pump inhibitors described herein are cancer-specific. Cancer-specific agents are agents that have been shown to be particularly effective against certain types of cancer. Cancer-specific agents that can be administered with the SERCA pump inhibitors described herein are listed in Table 7 below.

TABLE 7

CANCER-SPECIFIC AGENTS

| Cancer type | Agents |
| --- | --- |
| Pancreatic cancer | Chemotherapeutics (Paclitaxel Albumin-stabilized Nanoparticle Formulation, Erlotinib Hydrochloride, Everolimus, Fluorouracil Injection, Gemcitabine Hydrochloride, Irinotecan Hydrochloride Liposome, Mitomycin C, Sunitinib Malate, Folfirinox, Gemcitabine-Cisplatin, Gemcitabine-Oxaliplatin, Off, Lanreotide Acetate, Abraxane, Gemcitabine, Irinotecan, 5-FU, Oxaliplatin) |
| Melanoma | Checkpoint inhibitors (pembro, ipi, nivolumab, durvalumab), BRaf inhibitors (vemurafenib, debrafenib), MEK inhibitors, CDK4 inhibitors (ribociclib) |
| Renal cell carcinoma | Checkpoint inhibitors (pembro, ipi, nivolumab, durvalumab), mTOR inhibitors (everolimus), bevacizumab |
| Lung cancer | Checkpoint inhibitors (pembro, ipi, nivolumab, durvalumab), EGFR inhibitors (erlotinib, gefitinib, cetuximab) |
| Esophageal cancer | Chemotherapeutic agents (5FU, docetaxel), trastuzumab |
| Ovarian cancer | Chemotherapeutics (taxanes, cisplatin) |
| Uterine cancer | Chemotherapeutics (taxanes, cisplatin) |
| Head and Neck cancer | Checkpoint inhibitors (pembro, ipi, nivolumab, durvalumab), EGFR inhibitors (erlotinib, gefitinib, cetuximab) |
| Mesothelioma | Chemotherapeutics (pemetrexed, cisplatin) |

Non-Drug Therapies

Another type of agent that can be administered in combination with a SERCA pump inhibitor is a therapeutic agent that is a non-drug treatment. For example, the second therapeutic agent is radiation therapy, cryotherapy, hyperthermia and/or surgical excision of tumor tissue.

CAR-T Therapy

Another therapy that can be employed in combination with the methods and compositions described herein is chimeric antigen receptor (CAR)-T therapy, or therapy with lymphocytes, such as autologous or allogeneic T cells, that have been modified to express a CAR that recognizes specific cancer antigens. Commonly, CARs contain a single chain fragment variable (scFv) region of an antibody or a binding domain specific for a tumor associated antigen (TAA) coupled via hinge and transmembrane regions to cytoplasmic domains of T cell signaling molecules. The most common lymphocyte activation moieties include a T cell costimulatory domain (e.g., CD28 and/or CD137) in tandem with a T cell effector function triggering (e.g. CD3) moiety. CARs have the ability to redirect T cell reactivity and specifity toward a selected target in a non-MHC restricted manner, exploiting the antigen-binding properties of monoclonal antibodies. The non-MHC restricted antigen recognition gives CAR-T cells the ability to bypass a major mechanism of tumor escape.

Anti-Cancer Vaccines

Many experimental strategies for vaccination against tumors have been devised (see, e.g., Armstrong et al., British J of Radiology 74:991, 2001; Sinkovics and Horvath, Int. J. of Oncology 16:81, 2000; DeVita, V. et al., eds., Cancer: Principles and Practice of Oncology. Sixth Edition. 2001, Philadelphia: Lippincott Williams & Wilkins). In one of these strategies, a vaccine is prepared using autologous or allogeneic tumor cells. Alternatively, an anti-cancer vaccine can take the form of a tumor specific antigen. The study of gene expression and large-scale gene expression patterns in various tumors has led to the definition of so-called tumor specific antigens (Rosenberg, Immunity 10:281, 1999). In many cases, these tumor specific antigens are differentiation antigens expressed in the tumors and in the cell from which the tumor arose. These proteins are normally viewed by the immune system as self antigens and are therefore tolerant to them. Tumor antigens may also be "neo-antigens" expressed in cancer cells because of somatic mutations that alter protein sequence or create fusion proteins between two unrelated sequences or idiotype from B cell tumors. Another form of tumor specific antigen is purified heat shock proteins (HSP) isolated from the tumor tissue itself. These heat shock proteins contain fragments of proteins from the tumor cells and are highly efficient at delivery to antigen presenting cells for eliciting tumor immunity (Suot and Srivastava, Science 269:1585, 1995; Tamura et al., Science 278:117, 1997). Other tumor vaccines may include the proteins from viruses implicated in human cancers such a human papilloma viruses (HPV), hepatitis viruses (HBV and HCV) and Kaposi's herpes sarcoma virus (KHSV). Anti-cancer vaccines may be DC vaccines, vaccines containing tumor antigengs or epitopes, or virus vectored cancer vaccines.

Neurotransmission Modulators

In some embodiments, the SERCA pump inhibitor is administered in combination with a neurotransmission modulator (e.g., an agent that increases or decreases neurotransmission). A neurotransmission modulator can be used to modulate neural activity in a cancer or tumor that is innervated by nerves or to modulate immune cells that express neurotransmitter receptors. For example, in some embodiments, the neurotransmission modulator is a neurotransmitter or neurotransmitter receptor listed in Table 8 or 9, or an agonist or antagonist listed in Tables 10A-10K for a corresponding neurotransmitter pathway member. In some embodiments, the neurotransmission modulator is a neurotransmission modulator listed in Table 11. Neurotransmission modulators that increase neurotransmission include neurotransmitters and neurotransmitter receptors listed in Tables 8 and 9 and analogs thereof, and neurotransmitter agonists (e.g., small molecules that agonize a neurotransmitter receptor listed in Table 8). Exemplary agonists are listed in Tables 10A-10K. In some embodiments, neurotransmission is increased via administration, local delivery, or stabilization of neurotransmitters (e.g., ligands listed in Tables 8 or 9). Neurotransmission modulators that increase neurotransmission also include agents that increase neurotransmitter synthesis or release (e.g., agents that increase the activity of a biosynthetic protein encoded by a gene in Table 8 via stabilization, overexpression, or upregulation, or agents that increase the activity of a synaptic or vesicular protein via stabilization, overexpression, or upregulation), prevent neurotransmitter reuptake or degradation (e.g., agents that block or antagonize transporters that remove neurotransmitter from the synaptic cleft), increase neurotransmitter receptor activity (e.g., agents that increase the activity of a signaling protein encoded by a gene in Table 8 via stabilization, overexpression, agonism, or upregulation, or agents that upregulate, agonize, or stabilize a neurotransmitter receptor listed in Table 8), increase neurotransmitter receptor synthesis or membrane insertion, decrease neurotransmitter degradation, and regulate neurotransmitter receptor conformation (e.g., agents that bind to a receptor and keep it in an "open" or "primed" conformation). In some embodiments, the neurotransmitter receptor is a channel, the activity of which can be increased by agonizing, opening, stabilizing, or overexpressing the channel. Neurotransmission modulators can increase neurotransmission by 10%, 20%, 30%, 40%, 50%, 60%, 70%, 80%, 90%, 95%, 98% or more. Exemplary neurotransmission modulators are listed in Table 11.

Neurotransmission modulators that decrease neurotransmission include neurotransmitter antagonists (e.g., small molecules that antagonize a neurotransmitter receptor listed in Table 8). Exemplary antagonists are listed in Tables 10A-10K. Neurotransmission modulators that decrease neurotransmission also include agents that decrease neurotransmitter synthesis or release (e.g., agents that decrease the activity of a biosynthetic protein encoded by a gene in Table 8 via inhibition or downregulation, or agents that decrease the activity of a synaptic or vesicular protein via blocking, disrupting, downregulating, or antagonizing the protein), increase neurotransmitter reuptake or degradation (e.g., agents that agonize, open, or stabilize transporters that remove neurotransmitter from the synaptic cleft), decrease neurotransmitter receptor activity (e.g., agents that decrease the activity of a signaling protein encoded by a gene in 6 or via blocking or antagonizing the protein, or agents that block, antagonize, or downregulate a neurotransmitter receptor listed in Table 8), decrease neurotransmitter receptor synthesis or membrane insertion, increase neurotransmitter degradation, regulate neurotransmitter receptor conformation (e.g., agents that bind to a receptor and keep it in a "closed" or "inactive" conformation), and disrupt the pre- or postsynaptic machinery (e.g., agents that block or disrupt a structural protein, or agents that block, disrupt, downregulate, or antagonize a synaptic or vesicular protein). In some embodiments, the neurotransmitter receptor is a channel (e.g., a ligand or voltage gated ion channel), the activity of which can be decreased by blockade, antagonism, or inverse agonism of the channel. Neurotransmission modulators that decrease neurotransmission further include agents that sequester, block, antagonize, or degrade a neurotransmitter listed in Tables 8 or 9. Neurotransmission modulators that decrease or block neurotransmission include antibodies that bind to or block the function of neurotransmitters, neurotransmitter receptor antagonists, and toxins that disrupt synaptic release. Neurotransmission modulators can decrease neurotransmission by 10%, 20%, 30%, 40%, 50%, 60%, 70%, 80%, 90%, 95%, 98% or more. Neurotransmission modulator can be administered in any of the modalities described herein (e.g., antibody, small molecule, nucleic acid, polypeptide, or viral vector).

TABLE 8

NEUROTRANSMITTER GENES & PATHWAYS

| Gene | Pathway | Type | Accession Number | Entrez Gene ID |
|---|---|---|---|---|
| ABAT | Neurotransmitter | Biosynthesis | P80404 | 18 |
| ACHE | Neurotransmitter | Biosynthesis | P22303 | 43 |
| ADORA2A | Neurotransmitter | Receptor | P29274 | 135 |
| ADORA2B | Neurotransmitter | Receptor | P29275 | 136 |
| Adra1a | Adrenergic/ Neurotransmitter | Receptor | P35348 | 148 |
| Adra1b | Adrenergic/ Neurotransmitter | Receptor | P35368 | 147 |
| Adra1d | Adrenergic/ Neurotransmitter | Receptor | P25100 | 146 |
| Adra2a | Adrenergic/ Neurotransmitter | Receptor | P08913 | 150 |
| Adra2b | Adrenergic/ Neurotransmitter | Receptor | P18089 | 151 |
| Adra2c | Adrenergic/ Neurotransmitter | Receptor | P18825 | 152 |
| Adrb1 | Adrenergic/ Neurotransmitter | Receptor | P08588 | 153 |
| Adrb2 | Adrenergic/ Neurotransmitter | Receptor | P07550 | 154 |
| Adrb3 | Adrenergic/ Neurotransmitter | Receptor | P13945 | 155 |
| Adrbk1 | Adrenergic | Kinase | P25098 | 156 |
| Adrbk2 | Adrenergic | Kinase | P35626 | 157 |
| BACE1 | Neurotransmitter | Biosynthesis | P56817 | 23621 |
| BCHE | Neurotransmitter | Biosynthesis | P06276 | 590 |
| BRS3 | Neuromodulator | Receptor | P32247 | P32247 |
| C6orf89 | Neuromodulator | Receptor | Q6UWU4 | 221477 |
| CHAT | Neurotransmitter | Biosynthesis | P28329 | 1103 |
| CHRFAM7A | Neurotransmitter | Receptor | Q494W8 | 89832 |
| Chrm1 | Cholinergic/ Neurotransmitter | Receptor | P11229 | 1128 |
| Chrm2 | Cholinergic/ Neurotransmitter | Receptor | P08172 | 1129 |
| Chrm3 | Cholinergic/ Neurotransmitter | Receptor | P20309 | 1131 |
| Chrm4 | Cholinergic/ Neurotransmitter | Receptor | P08173 | 1132 |
| Chrm5 | Cholinergic/ Neurotransmitter | Receptor | P08912 | 1133 |
| Chrna1 | Cholinergic/ Neurotransmitter | Receptor | P02708 | 1134 |
| Chrna10 | Cholinergic/ Neurotransmitter | Receptor | Q9GZZ6 | 57053 |
| Chrna2 | Cholinergic/ Neurotransmitter | Receptor | Q15822 | 1135 |
| Chrna3 | Cholinergic/ Neurotransmitter | Receptor | P32297 | 1136 |
| Chrna4 | Cholinergic/ Neurotransmitter | Receptor | P43681 | 1137 |
| Chrna5 | Cholinergic/ Neurotransmitter | Receptor | P30532 | 1138 |
| Chrna6 | Cholinergic/ Neurotransmitter | Receptor | Q15825 | 8973 |
| Chrna7 | Cholinergic/ Neurotransmitter | Receptor | P36544 | 1139 |
| Chrna9 | Cholinergic/ Neurotransmitter | Receptor | Q9UGM1 | 55584 |
| Chrnb1 | Cholinergic/ Neurotransmitter | Receptor | P11230 | 1140 |
| Chrnb2 | Cholinergic/ Neurotransmitter | Receptor | P17787 | 1141 |
| Chrnb3 | Cholinergic/ Neurotransmitter | Receptor | Q05901 | 1142 |
| Chrnb4 | Cholinergic/ Neurotransmitter | Receptor | P30926 | 1143 |
| Chrnd | Cholinergic/ Neurotransmitter | Receptor | Q07001 | 1144 |
| Chrne | Cholinergic/ Neurotransmitter | Receptor | Q04844 | 1145 |
| Chrng | Cholinergic/ Neurotransmitter | Receptor | P07510 | 1146 |
| CNR1 | Cannabinoid/ Neurotransmitter | Receptor | P21554 | 1268 |
| CNR2 | Cannabinoid/ Neurotransmitter | Receptor | P34972 | 1269 |
| CNRIP1 | Neurotransmitter | Receptor | Q96F85 | 25927 |
| COMT | Neurotransmitter | Biosynthesis | P21964 | 1312 |
| CPA4 | Neurotransmitter | Biosynthesis | Q9UI42 | 51200 |
| CPE | Neuropeptide/ Neurotransmitter | Biosynthesis | P16870 | 1363 |

TABLE 8-continued

NEUROTRANSMITTER GENES & PATHWAYS

| Gene | Pathway | Type | Accession Number | Entrez Gene ID |
|---|---|---|---|---|
| CREM | Neurotransmitter | Signaling | Q03060 | 1390 |
| DAGLA | Neurotransmitter (Cannabinoid) | Biosynthesis | Q9Y4D2 | 747 |
| DAGLB | Neurotransmitter (Cannabinoid) | Biosynthesis | Q8NCG7 | 221955 |
| DBH | Neurotransmitter | Biosynthesis | P09172 | 1621 |
| DDC | Neurotransmitter | Biosynthesis | P20711 | 1644 |
| DGKI | Neurotransmitter | Biosynthesis | O75912 | 9162 |
| DOPO | Dopaminergic | Receptor | P09172 | 1621 |
| DPP4 | Neurotransmitter | Biosynthesis | P27487 | 1803 |
| Drd1 | Dopaminergic/Neurotransmitter | Receptor | P21728 | 1812 |
| Drd2 | Dopaminergic/Neurotransmitter | Receptor | P14416 | 1813 |
| Drd3 | Dopaminergic/Neurotransmitter | Receptor | P35462 | 1814 |
| Drd4 | Dopaminergic/Neurotransmitter | Receptor | P21917 | 1815 |
| Drd5 | Dopaminergic/Neurotransmitter | Receptor | P21918 | 1816 |
| ECEL1 | Neurotransmitter | Biosynthesis | O95672 | 9427 |
| FAAH | Neurotransmitter | Biosynthesis | O00519 | 2166 |
| FNTA | Neurotransmitter | Signaling | P49354 | 2339 |
| GABARAP | Neurotransmitter | Receptor | O95166 | 11337 |
| GABARAPL1 | Amine Neuromodulator | Receptor | Q9H0R8 | 23710 |
| GABARAPL2 | Amine Neuromodulator | Receptor | P60520 | 11345 |
| GABBR1 | Neurotransmitter | Receptor | Q9UBS5 | 2550 |
| GABBR2 | Amine Neuromodulator | Receptor | O75899 | 9568 |
| GABRA1 | Neurotransmitter | Receptor | P14867 | 2554 |
| GABRA2 | Neurotransmitter | Receptor | P47869 | 2555 |
| GABRA3 | Neurotransmitter | Receptor | P34903 | 2556 |
| GABRA4 | Neurotransmitter | Receptor | P48169 | 2557 |
| GABRA5 | Neurotransmitter | Receptor | P31644 | 2558 |
| GABRA6 | Neurotransmitter | Receptor | Q16445 | 2559 |
| GABRB1 | Neurotransmitter | Receptor | P18505 | 2560 |
| GABRB2 | Neurotransmitter | Receptor | P47870 | 2561 |
| GABRB3 | Neurotransmitter | Receptor | P28472 | 2562 |
| GABRD | Neurotransmitter | Receptor | O14764 | 2563 |
| GABRE | Neurotransmitter | Receptor | P78334 | 2564 |
| GABRG1 | Neurotransmitter | Receptor | Q8N1C3 | 2565 |
| GABRG2 | Neurotransmitter | Receptor | P18507 | 2566 |
| GABRG3 | Neurotransmitter | Receptor | Q99928 | 2567 |
| GABRP | Neurotransmitter | Receptor | O00591 | 2568 |
| GABRQ | Neurotransmitter | Receptor | Q9UN88 | 55879 |
| GABRR1 | Neurotransmitter | Receptor | P24046 | 2569 |
| GABRR2 | Neurotransmitter | Receptor | P28476 | 2570 |
| GABRR3 | Neurotransmitter | Receptor | A8MPY1 | 200959 |
| GAD1 | Neurotransmitter | Biosynthesis | Q99259 | 2571 |
| GAD2 | Neurotransmitter | Biosynthesis | Q05329 | 2572 |
| GCHFR | Neurotransmitter | Biosynthesis | P30047 | 2644 |
| GLRA1 | Neurotransmitter | Receptor | P23415 | 2741 |
| GLRA2 | Neurotransmitter | Receptor | P23416 | 2742 |
| GLRA3 | Neurotransmitter | Receptor | O75311 | 8001 |
| GLRA4 | Neurotransmitter | Receptor | Q5JXX5 | 441509 |
| GLRB | Neurotransmitter | Receptor | P48167 | 2743 |
| GLS | Neurotransmitter | Biosynthesis | O94925 | 2744 |
| GLS2 | Neurotransmitter | Biosynthesis | Q9UI32 | 27165 |
| GluA1 (GluR1) | Amine Neuromodulator | Receptor | P42261 | 2890 |
| GluK1 (GluR5) | Amine Neuromodulator | Receptor | P39086 | 2897 |
| GLUL | Neurotransmitter | Biosynthesis | P15104 | 2752 |
| GluN1(NR1) | Amine Neuromodulator | Receptor | Q05586 | 2902 |
| GNMT | Neurotransmitter | Biosynthesis | Q14749 | 27232 |
| GPER1 | Neurotransmitter | Receptor | Q99527 | 2852 |
| GPR1 | Neurotransmitter | Receptor | P46091 | 2825 |
| GPR139 | Neurotransmitter | Receptor | Q6DWJ6 | 124274 |
| GPR143 | Neurotransmitter | Receptor | P51810 | 4935 |
| GPR149 | Neurotransmitter | Receptor | Q86SP6 | 344758 |
| GPR18 | Neurotransmitter | Receptor | Q14330 | 2841 |
| GPR21 | Neurotransmitter | Receptor | Q99679 | 2844 |
| GPR26 | Neurotransmitter | Receptor | Q8NDV2 | 2849 |
| GPR3 | Neurotransmitter | Receptor | P46089 | 2827 |
| GPR35 | Neurotransmitter | Receptor | Q9HC97 | 2859 |
| GPR52 | Neurotransmitter | Receptor | Q9Y2T5 | 9293 |
| GPR55 | Neurotransmitter | Receptor | Q9Y2T6 | 9290 |
| GPR78 | Neurotransmitter | Receptor | Q96P69 | 27201 |
| GPR83 | Neurotransmitter | Receptor | Q9NYM4 | 10888 |
| GPR84 | Neurotransmitter | Receptor | Q9NQS5 | 53831 |
| GPRASP1 | Neurotransmitter | Receptor | Q5JY77 | 9737 |
| GPR50 | Amine Neuromodulator | Receptor | Q13585 | 9248 |
| GRIA1 | Neurotransmitter | Receptor | P42261 | 2890 |
| GRIA2 | Neurotransmitter | Receptor | P42262 | 2891 |
| GRIA3 | Neurotransmitter | Receptor | P42263 | 2892 |
| GRIA4 | Neurotransmitter | Receptor | P48058 | 2893 |
| GRID1 | Neurotransmitter | Receptor | Q9ULK0 | 2894 |
| GRID2 | Neurotransmitter | Receptor | O43424 | 2895 |
| GRIK1 | Neurotransmitter | Receptor | P39086 | 2897 |
| GRIK2 | Neurotransmitter | Receptor | Q13002 | 2898 |
| GRIK3 | Neurotransmitter | Receptor | Q13003 | 2899 |
| GRIK4 | Neurotransmitter | Receptor | Q16099 | 2900 |
| GRIK5 | Neurotransmitter | Receptor | Q16478 | 2901 |
| GRIN1 | Neurotransmitter | Receptor | Q05586 | 2902 |
| GRIN2A | Neurotransmitter | Receptor | Q12879 | 2903 |
| GRIN2B | Neurotransmitter | Receptor | Q13224 | 2904 |
| GRIN2C | Neurotransmitter | Receptor | Q14957 | 2905 |
| GRIN2D | Neurotransmitter | Receptor | O15399 | 2906 |
| GRIN3A | Neurotransmitter | Receptor | Q8TCU5 | 116443 |
| GRIN3B | Neurotransmitter | Receptor | O60391 | 116444 |
| GRK2 | Neurotransmitter | Receptor | P25098 | 156 |
| GRK3 | Neurotransmitter | Receptor | P35626 | 157 |
| GRM1 | Neurotransmitter | Receptor | Q13255 | 2911 |
| GRM2 | Neurotransmitter | Receptor | Q14416 | 2912 |
| GRM3 | Neurotransmitter | Receptor | Q14832 | 2913 |
| GRM4 | Neurotransmitter | Receptor | Q14833 | 2914 |
| GRM5 | Neurotransmitter | Receptor | P41594 | 2915 |
| GRM6 | Neurotransmitter | Receptor | O15303 | 2916 |
| GRM7 | Neurotransmitter | Receptor | Q14831 | 2917 |
| GRM8 | Neurotransmitter | Receptor | O00222 | 2918 |
| HNMT | Neurotransmitter | Biosynthesis | P50135 | 3176 |
| HOMER1 | Neurotransmitter | Receptor | Q86YM7 | 9456 |
| HRH1 | Neurotransmitter | Receptor | P35367 | 3269 |
| HRH2 | Neurotransmitter | Receptor | P25021 | 3274 |
| HRH3 | Neurotransmitter | Receptor | Q9Y5N1 | 11255 |
| HRH4 | Neurotransmitter | Receptor | Q9H3N8 | 59340 |
| Htr1a | Neurotransmitter | Receptor | P08908 | 3350 |
| Htr1b | Neurotransmitter | Receptor | P28222 | 3351 |
| Htr1c | Neurotransmitter | Receptor | P28335 | |
| Htr1d | Neurotransmitter | Receptor | P28221 | 3352 |
| Htr1e | Neurotransmitter | Receptor | P28566 | 3354 |
| Htr1f | Neurotransmitter | Receptor | P30939 | 3355 |
| Htr2a | Neurotransmitter | Receptor | P28223 | 3356 |
| Htr2b | Neurotransmitter | Receptor | P41595 | 3357 |
| Htr2c | Neurotransmitter | Receptor | P28335 | 3358 |
| Htr3a | Neurotransmitter | Receptor | P46098 | 3359 |
| Htr3b | Neurotransmitter | Receptor | O95264 | 9177 |
| Htr3c | Neurotransmitter | Receptor | Q8WXA8 | 170572 |
| Htr3d | Neurotransmitter | Receptor | Q70Z44 | 200909 |
| HTR3E | Neurotransmitter | Receptor | A5X5Y0 | 285242 |
| Htr4 | Neurotransmitter | Receptor | Q13639 | 3360 |
| Htr5a | Neurotransmitter | Receptor | P47898 | 3361 |
| Htr5b | Neurotransmitter | Receptor | P35365 | 79247 |
| HTR5BP | Neurotransmitter | Receptor | | 645694 |
| Htr6 | Neurotransmitter | Receptor | P50406 | 3362 |
| Htr7 | Neurotransmitter | Receptor | P32305 | 3363 |
| ITPR1 | Neurotransmitter | Signaling | Q14643 | 3708 |
| ITPR2 | Neurotransmitter | Signaling | Q14571 | 3709 |
| ITPR3 | Neurotransmitter | Signaling | Q14573 | 3710 |
| LYNX1 | Neurotransmitter | Receptor | Q9BZG9 | 66004 |
| MAOA | Neurotransmitter | Biosynthesis | P21397 | 4128 |
| MAOB | Neurotransmitter | Biosynthesis | P27338 | 4129 |
| NAMPT | Neurotransmitter | Biosynthesis | P43490 | 10135 |
| NISCH | Neurotransmitter | Receptor | Q9Y2I1 | 11188 |
| NOS1 | Neurotransmitter | Biosynthesis | P29475 | 4842 |
| NPTN | Neurotransmitter | Receptor | Q9Y639 | 27020 |

TABLE 8-continued

NEUROTRANSMITTER GENES & PATHWAYS

| Gene | Pathway | Type | Accession Number | Entrez Gene ID |
|---|---|---|---|---|
| P2RX1 | Neurotransmitter | Receptor | P51575 | 5023 |
| P2RX2 | Neurotransmitter | Receptor | Q9UBL9 | 22953 |
| P2RX3 | Neurotransmitter | Receptor | P56373 | 5024 |
| P2RX4 | Neurotransmitter | Receptor | Q99571 | 5025 |
| P2RX5 | Neurotransmitter | Receptor | Q93086 | 5026 |
| P2RX6 | Neurotransmitter | Receptor | O15547 | 9127 |
| P2RX7 | Neurotransmitter | Receptor | Q99572 | 5027 |
| P2RY11 | Neurotransmitter | Receptor | Q96G91 | 5032 |
| PAH | Neurotransmitter | Biosynthesis | P00439 | 5053 |
| PC | Neurotransmitter | Biosynthesis | P11498 | 5091 |
| PDE1B | Neurotransmitter | Signaling | Q01064 | 5153 |
| PDE4A | Neurotransmitter | Signaling | P27815 | 5141 |
| PDE4D | Neurotransmitter | Signaling | Q08499 | 5144 |
| PHOX2A | Neurotransmitter | Biosynthesis | O14813 | 401 |
| PHOX2B | Neurotransmitter | Biosynthesis | Q99453 | 8929 |
| PIK3CA | Neurotransmitter | Signaling | P42336 | 5290 |
| PIK3CB | Neurotransmitter | Signaling | P42338 | 5291 |
| PIK3CG | Neurotransmitter | Signaling | P48736 | 5294 |
| PLCB1 | Neurotransmitter | Signaling | Q9NQ66 | 23236 |
| PLCB2 | Neurotransmitter | Signaling | Q00722 | 5330 |
| PLCB3 | Neurotransmitter | Signaling | Q01970 | 5331 |
| PLCB4 | Neurotransmitter | Signaling | Q15147 | 5332 |
| PLCD1 | Neurotransmitter | Signaling | P51178 | 5333 |
| PLCE1 | Neurotransmitter | Signaling | Q9P212 | 51196 |
| PLCG1 | Neurotransmitter | Signaling | P19174 | 5335 |
| PLCL1 | Neurotransmitter | Signaling | Q15111 | 5334 |
| PLCL2 | Neurotransmitter | Signaling | Q9UPR0 | 23228 |
| PPP1CB | Neurotransmitter | Signaling | P62140 | 5500 |
| PPP1CC | Neurotransmitter | Signaling | P36873 | 5501 |
| PRIMA1 | Neurotransmitter | Biosynthesis | Q86XR5 | 145270 |
| PRKACG | Neurotransmitter | Signaling | P22612 | 5568 |
| PRKAR2B | Neurotransmitter | Signaling | P31323 | 5577 |
| PRKCG | Neurotransmitter | Signaling | P05129 | 5582 |
| PRKX | Neurotransmitter | Signaling | P51817 | 5613 |
| RIC3 | Neurotransmitter | Receptor | Q7Z5B4 | 79608 |
| SHANK3 | Neurotransmitter | Signaling | Q9BYB0 | 85358 |
| SLC6A1 | Amine Neuromodulator | Transferase | P30531 | 6529 |
| SLC6A13 | Amine Neuromodulator | Transferase | Q9NSD5 | 6540 |
| Slc6a4 | Serotonin | Transporter | P31645 | 6532 |
| SNX13 | Neurotransmitter | Signaling | Q9Y5W8 | 23161 |
| TAAR1 | Amine Neuromodulator | Receptor | Q96RJ0 | 134864 |
| TAAR2 | Amine Neuromodulator | Receptor | Q9P1P5 | 9287 |
| TAAR5 | Neurotransmitter | Receptor | O14804 | 9038 |
| TH | Neurotransmitter | Biosynthesis | P07101 | 7054 |
| TPH1 | Neurotransmitter | Biosynthesis | P17752 | 7166 |
| TPH2 | Neurotransmitter | Biosynthesis | Q8IWU9 | 121278 |
| TRHDE | Neurotransmitter | Biosynthesis | Q9UKU6 | 29953 |

TABLE 9

NEUROTRANSMITTERS

| Ligand | Pathway | Type |
|---|---|---|
| 2-Arachidonoylglycerol | Endocannabinoid | Ligand |
| 2-Arachidonyl glyceryl ether | Endocannabinoid | Ligand |
| 3-methoxytyramine | Amines | Ligand |
| Acetylcholine | Amino Acids | Ligand |
| Adenosine | Purine | Ligand |
| Adenosine triphosphate | Purine | Ligand |
| Agmatine | Amino Acids | Ligand |
| Anandamide | Endocannabinoid | Ligand |
| Aspartate | Amino Acids | Ligand |
| Carbon monoxide | Gas | Ligand |
| D-serine | Amino Acids | Ligand |
| Dopamine | Monoamines | Ligand |
| Dynorphin | Opioids | Ligand |
| Endorphin | Opioids | Ligand |
| Enkephalin | Opioids | Ligand |
| Epinephrine | Monoamines | Ligand |
| Gamma-aminobutyric acid | Amino Acids | Ligand |
| Glutamate | Amino Acids | Ligand |
| Glycine | Amino Acids | Ligand |
| Histamine | Monoamines | Ligand |
| N-Acetylaspartylglutamate | Neuropeptides | Ligand |
| N-Arachidonoyl dopamine | Endocannabinoid | Ligand |
| N-methylphenethylamine | Amines | Ligand |
| N-methyltryptamine | Amines | Ligand |
| Nitric oxide | Gas | Ligand |
| Norepinephrine | Monoamines | Ligand |
| Octopamine | Amines | Ligand |
| Phenethylamine | Amines | Ligand |
| Serotonin | Monoamines | Ligand |
| Synephrine | Amines | Ligand |
| Tryptamine | Amines | Ligand |
| Tyramine | Amines | Ligand |
| Virodhamine | Endocannabinoid | Ligand |

TABLE 10A

AGONISTS AND ANTAGONIST AGENTS

| Gene | Agonist | Antagonist |
|---|---|---|
| Adrb2 Accession Number: P07550 | NCX 950 | Alprenolol |
| | Bitolterol | Carvedilol |
| | Isoetarine | Desipramine |
| | Norepinephrine | Nadolol |
| | Phenylpropanolamine | Levobunolol |
| | Dipivefrin | Metipranolol |
| | Epinephrine | Bevantolol |
| | Orciprenaline | Oxprenolol |
| | Dobutamine | Nebivolol |
| | Ritodrine | Asenapine |
| | Terbutaline | Bupranolol |
| | Salmeterol | Penbutolol |
| | Formoterol | Celiprolol |
| | Salbutamol | Pindolol |
| | Isoprenaline | Acebutolol |
| | Arbutamine | Bopindolol |
| | Arformoterol | |
| | Fenoterol | |
| | Pirbuterol | |

TABLE 10A-continued

AGONISTS AND ANTAGONIST AGENTS

| Gene | Agonist | Antagonist |
|---|---|---|
| | Ephedra | |
| | Procaterol | |
| | Clenbuterol | |
| | Bambuterol | |
| | Indacaterol | |
| | Droxidopa | |
| | Olodaterol | |
| | Vilanterol | |
| | Pseudoephedrine | |
| | Cabergoline | |
| | Mirtazepine | |
| Adra1d Accession Number: P25100 | Midodrine Norepinephrine Clonidine Oxymetazoline Pergolide Bromocriptine Droxidopa Xylometazoline Ergotamine Cirazoline Cabergoline Methoxamine Epinephrine | Dapiprazole Amitriptyline Alfuzosin Promazine Prazosin Imipramine Nortriptyline Doxazosin Nicardipine Dronedarone Tamsulosin Propiomazine Phenoxybenzamine Carvedilol Doxepin Terazosin Quetiapine Methotrimeprazine Silodosin |
| Adrb1 Accession Number: P08588 | Isoetarine Norepinephrine Phenylpropanolamine Epinephrine Dobutamine Salbutamol Isoprenaline Arbutamine Fenoterol Pirbuterol Ephedra Clenbuterol Droxidopa Pseudoephedrine Carteolol Cabergoline Mirtazapine Loxapine Vortioxetine Desipramine | Esmolol Betaxolol Metoprolol Atenolol Timolol Sotalol Propranolol Labetalol Bisoprolol Alprenolol Amiodarone Carvedilol Nadolol Levobunolol Metipranolol Bevantolol Practolol Oxprenolol Celiprolol Nebivolol Asenapine Bupranolol Penbutolol Pindolol Acebutolol Bopindolol Cartelol |
| Adrb3 Accession Number: P13945 | SR 58611 Norepinephrine Epinephrine Isoprenaline Arbutamine Fenoterol Ephedra Clenbuterol Droxidopa Mirabegron | Bopindolol Propranolol Bupranolol |
| Adrbk1 Accession Number: P25098 | ATP Carbachol Dopamine Isoproterenol Morphine DAMGO histamine Acetylcholine Etorphine | Alprenolol Heparin |

TABLE 10A-continued

| AGONISTS AND ANTAGONIST AGENTS | | |
|---|---|---|
| Gene | Agonist | Antagonist |
| | NMDA | |
| | Dopamine | |
| Adrbk2 | Isoproterenol | Propranolol |
| Accession Number: | DAMGO | |
| P26819 | ATP | |
| Chrm3 | cgmp | MT3 |
| Accession Number: | ATP | Hexocyclium |
| P20309 | Cevimeline | Himbacine |
| | arecoline | Biperiden |
| | oxotremorine-M | lithocholylcholine |
| | NNC 11-1314 | AFDX384 |
| | xanomeline | 4-DAMP |
| | oxotremorine | hexahydrodifenidol |
| | pentylthio-TZTP | VU0255035 |
| | arecaidine propargyl ester | N-methyl scopolamine |
| | NNC 11-1607 | Darifenacin |
| | furmethide | Thiethylperazine |
| | NNC 11-1585 | methoctramine |
| | Acetylcholine | silahexocyclium |
| | methylfurmethide | Strychnine |
| | Bethanechol | MT7 |
| | Carbachol | Heparin |
| | Succinylcholine | Olanzapine |
| | ALKS 27 | Pirenzepine |
| | itopride | Clidinium |
| | methacholine | Ipratropium |
| | Meperidine | Propantheline |
| | Cinnarizine | Dicyclomine |
| | Trimipramine | Darifenacin |
| | | Tiotropium |
| | | Atropine |
| | | Scopolamine |
| | | Amitriptyline |
| | | Doxepin |
| | | Lidocaine |
| | | Nortriptyline |
| | | Tropicamide |
| | | Metixene |
| | | Homatropine Methylbromide |
| | | Solifenacin |
| | | Glycopyrrolate |
| | | Propiomazine |
| | | Diphemanil Methylsulfate |
| | | Promethazine |
| | | Diphenidol |
| | | Pancuronium |
| | | Ziprasidone |
| | | Quetiapine |
| | | Imipramine |
| | | Clozapine |
| | | Cyproheptadine |
| | | Aripiprazole |
| | | Nicardipine |
| | | Amoxapine |
| | | Loxapine |
| | | Promazine |
| | | Oxyphencyclimine |
| | | Anisotropine Methylbromide |
| | | Tridihexethyl |
| | | Chlorpromazine |
| | | Ketamine |
| | | Cyclosporin A |
| | | Paroxetine |
| | | Benzquinamide |
| | | Tolterodine |
| | | Oxybutynin |
| | | Alcuronium |
| | | WIN 62,577 |
| | | Tramadol |
| | | Chlorprothixene |
| | | Aclidinium |
| | | Methotrimeprazine |
| | | Umeclidinium |
| | | Cryptenamine |
| | | Mepenzolate |
| | | Maprotiline |

TABLE 10A-continued

AGONISTS AND ANTAGONIST AGENTS

| Gene | Agonist | Antagonist |
|---|---|---|
| | | Brompheniramine |
| | | Isopropamide |
| | | Trihexyphenidyl |
| | | Ipratropium bromide |
| | | Hyoscyamine |
| | | Procyclidine |
| | | Pipecuronium |
| | | Fesoterodine |
| | | Disopyramide |
| | | Desipramine |
| | | Mivacuriurn |
| Chrna3 | Nicotine | A-867744 |
| Accession Number: | Varenicline | NS1738 |
| P32297 | Acetylcholine | Hexamethonium |
| | Ethanol | Mecamylamine |
| | Cytisine | Dextromethorphan |
| | Levamisole | Pentolinium |
| | Galantamine | Levomethadyl Acetate |
| | | Bupropion |
| Chrna6 | Nicotine | Hexamethonium |
| Accession Number: | Cytisine | Mecamylamine |
| Q15825 | Varenicline | |
| | Galantamine | |
| Chrna9 | Nicotine | Hexamethonium |
| Accession Number: | Galantamine | Mecamylamine |
| Q9UGM1 | Ethanol | Tetraethylammonium |
| | | Muscarine |
| | ATG003 | Strychnine |
| | Lobeline | |
| | RPI-78M | |
| Chrnb1 | Galantamine | |
| Accession Number: | | |
| P11230 | | |
| Chrnb4 | Nicotine | Atropine |
| Accession Number: | Varenicline | Oxybutynin |
| P30926 | PNU-120596 | Pentolinium |
| | Ethanol | Dextromethorphan |
| | Galantamine | |
| Chrng | Galantamine | |
| Accession Number: | | |
| P07510 | | |
| Adcyap1 | Nicotine | Atropine |
| Accession Number: | CGMP | PPADS |
| P18509 | Apomorphine | Onapristone |
| | Suramin | Muscarine |
| | Nifedipine | Haloperidol |
| | ATP | Astressin |
| | Dihydrotestosterone | Melatonin |
| | Maxadilan | Scopolamine |
| | Dexamethasone | Tetrodotoxin |
| | Acetylcholine | Apamin |
| | Histamine | Hexamethonium |
| | Carbachol | Indomethacin |
| | NMDA | Propranolol |
| | Dopamine | Bumetanide |
| | Isoproterenol | Progesterone |
| | Salbutamol | Charybdotoxin |
| | Morphine | Prazosin |
| | Clonidine | |
| | Nimodipine | |
| | 2,6-Diamino-Hexanoic Acid Amide | |
| CYSLTR1 | Salbutamol | Montelukast |
| Accession Number: | Dexamethasone | Zafirlukast |
| Q9Y271 | Arachidonic acid | Cinalukast |
| | Histamine | Pranlukast |
| | | Nedocromil |
| | | Theophylline |
| | | Indomethacin |
| | | Zileuton |
| | | Iralukast |
| | | Pobilukast |
| | | Sulukast |
| | | Verlukast |
| LTB4R | LTB | U75302 |
| Accession Number: | ATP | CP105696 |
| Q15722 | Dexamethasone | CP-195543 |

TABLE 10A-continued

AGONISTS AND ANTAGONIST AGENTS

| Gene | Agonist | Antagonist |
|---|---|---|
| | cholesterol | Etalocib |
| | 20-hydroxy-LTB< | SC-41930 |
| | 12R-HETE | LY255283 |
| | arachidonic acid | Zafirlukast |
| | | ONO-4057 |
| | | RO5101576 |
| | | BILL 260 |
| PENK | Dopamine | Naltrexone |
| Accession Number: | kainate | Naloxone |
| P01210 | NMDA | Progesterone |
| | DAMGO | |
| | Morphine | |
| Htr2c | Apomorphine | Melatonin |
| Accession Number: | Bifeprunox | SB 224289 |
| P28335 | Tramadol | LY334362 |
| | AL-37350A | FR260010 |
| | 5-MeO-DMT | Sulpiride |
| | BW723C86 | Thiethylperazine |
| | CGS-12066 | cyamemazine |
| | DOI | Mesulergine |
| | 5-CT | SB 221284 |
| | YM348 | Zotepine |
| | LSD | Metergoline |
| | xanomeline | methiothepin |
| | WAY-163909 | Spiperone |
| | Dopamine | SB 215505 |
| | LY344864 | Tiospirone |
| | VER-3323 | SB 228357 |
| | TFMPP | Pizotifen |
| | 8-OH-DPAT | SB 206553 |
| | MK-212 | SB 204741 |
| | NMDA | SDZ SER-082 |
| | org 12962 | Ritanserin |
| | 5-MeOT | SB 242084 |
| | RU 24969 | S33084 |
| | Acetylcholine | Roxindole |
| | QUINPIROLE | RS-127445 |
| | quipazine | Terguride |
| | tryptamine | EGIS-7625 |
| | Ro 60-0175 | SB 243213 |
| | Oxymetazoline | RS-102221 |
| | Ergotamine | Olanzapine |
| | Cabergoline | Aripiprazole |
| | Lorcaserin | Agomelatine |
| | Pergolide | Ziprasidone |
| | Methylergonovine | Quetiapine |
| | Renzapride | Sarpogrelate |
| | Pramipexole | Perphenazine |
| | GR-127935 | Thioridazine |
| | BRL-15572 | Sertindole |
| | ipsapirone | Loxapine |
| | SB 216641 | Methysergide |
| | SL65.0155 | Risperidone |
| | S 16924 | Asenapine |
| | Bromocriptine | Mianserin |
| | Lisuride | Clozapine |
| | Tegaserod | Trifluoperazine |
| | Epicept NP-1 | Trazodone |
| | dapoxetine | Doxepin |
| | Dexfenfluramine | Nortriptyline |
| | 3,4-Methylenedioxymethamphetamine | Chlorprothixene |
| | Ropinirole | Minaprine |
| | Maprotiline | Propiomazine |
| | Desipramine | Mirtazapine |
| | | Amoxapine |
| | | Yohimbine |
| | | Cyproheptadine |
| | | Imipramine |
| | | Amitriptyline |
| | | Promazine |
| | | Chlorpromazine |
| | | Ketamine |
| | | Propranolol |
| | | Fluoxetine |
| | | Ketanserin |

TABLE 10A-continued

AGONISTS AND ANTAGONIST AGENTS

| Gene | Agonist | Antagonist |
| --- | --- | --- |
| | | Mesulergine |
| | | AC-90179 |
| | | Ergoloid mesylate 2 |
| | | Methotrimeprazine |
| | | Paliperidone |
| | | Clomipramine |
| | | Trimipramine |
| | | Captodiame |
| | | Nefazodone |
| GABA Receptor Accession Numbers (Q9UBS5, O95166, O75899, P28472, P18507, P47870, P47869, O14764) | Bamaluzole<br>GABA<br>Gabamide<br>GABOB<br>Gaboxadol<br>Ibotenic acid<br>Isoguvacine<br>Isonipecotic acid<br>Muscimol<br>Phenibut<br>Picamilon<br>Progabide<br>Quisqualamine<br>SL 75102<br>Thiomuscimol<br>Alcohols (e.g., ethanol, isopropanol)<br>Avermectins (e.g., ivermectin)<br>Barbiturates (e.g., phenobarbital)<br>Benzodiazepines<br>Bromides (e.g., potassium bromide<br>Carbamates (e.g., meprobamate, carisoprodol)<br>Chloralose<br>Chlormezanone<br>Clomethiazole<br>Dihydroergolines (e.g., ergoloid (dihydroergotoxine))<br>Etazepine<br>Etifoxine<br>Imidazoles (e.g., etomidate)<br>Kavalactones (found in kava)<br>Loreclezole<br>Neuroactive steroids (e.g., allopregnanolone, ganaxolone)<br>Nonbenzodiazepines (e.g., zaleplon, zolpidem, zopiclone, eszopiclone)<br>Petrichloral<br>Phenols (e.g., propofol)<br>Piperidinediones (e.g., glutethimide, methyprylon)<br>Propanidid<br>Pyrazolopyridines (e.g., etazolate)<br>Quinazolinones (e.g., methaqualone)<br>Skullcap constituents<br>Stiripentol<br>Sulfonylalkanes (e.g., sulfonmethane, tetronal, trional)<br>Valerian constituents (e.g., valeric acid, valerenic acid)<br>Volatiles/gases (e.g., chloral hydrate, chloroform, diethyl ether, sevoflurane) | bicuculline<br>Metrazol<br>Flumazenil<br>Thiothixine<br>Bupropion<br>Caffeine |
| Glutamate Receptor Accession Number: (P42261, P39086, P39086, Q13585, P42261, P42262, P42263, P48058, P39086, Q13002, Q13003, Q13003, Q16478, Q12879, Q14957, Q13224, Q14957, O15399, Q8TCU5, O60391) | 3,5-dihydroxyphenylglycine<br>eglumegad<br>Biphenylindanone A<br>DCG-IV<br>L-AP4 | APICA<br>EGLU<br>LY-341,495 |

TABLE 10A-continued

AGONISTS AND ANTAGONIST AGENTS

| Gene | Agonist | Antagonist |
|---|---|---|
| CNR1/CNR2<br>Accession Number:<br>(P21554, P34972) | N-Arachidonoylethanolamine<br>2-Arachidonoyl-glycerol<br>2-Arachidonoyl-glycerylether<br>N-Arachidonoyl-dopamine<br>O-Arachidonoyl-ethanolamine<br>N-Arachidonoylethanolamine<br>2-Arachidonoyl-glycerol<br>2-Arachidonoyl-glycerylether<br>N-Arachidonoyl-dopamine<br>O-Arachidonoyl-ethanolamine<br>Δ9-THC<br>CP-55,940<br>R(+)-WIN 55,212-2<br>HU-210<br>Levonantradol<br>Nabilone<br>Methanandamide<br>ACEA<br>O-1812<br>Δ9-THC<br>CP-55,940<br>R(+)-WIN 55,212-2<br>HU-210<br>Levonantradol<br>Nabilone<br>Methanandamide<br>JWH-015<br>JWH-133 | SR 141716A<br>LY-320135<br>AM251<br>AM281<br>SR 144528<br>AM630 |

TABLE 10B

ADRENERGIC AGONISTS AND ANTAGONISTS

| Receptor | Agonist | Antagonist |
|---|---|---|
| Non-selective | adrenaline (epinephrine), noradrenaline (norepinephrine), isoprenaline (isoproterenol), dopamine, caffeine, nicotine, tyramine, methylphenidate, ephedrine and pseudophedrine. | carvedilol, arotinolol, and labetalol |
| α1 selective (ADRA1A, ADRA1B, ADRA1D) | phenylephrine, methoxamine, midodrine, cirazoline, xylometazoline, metaraminol chloroehtylclonidine, oxymetazoline | acepromazine, alfuzosin, doxazosin, labetalol, phenoxybenzamine, KW3902, phentolamine, prazosin, tamsulosin, terazosin, tolazoline, trazodone, amitriptyline, silodosin, clomipramine, doxepin, trimipramine, typical and atypical antipsychotics, and antihistamines, such as hyroxyzine |
| α2 selective (ADRA2A, ADRA2B, ADRA2C) | α-methyl dopa, clonidine, brimonidine, agmatine, dexmedetomidine, medetomidine, romifidine chloroethylclonidine, detomidine, lofexidine, xylazine, tizanidine, guanfacine, and amitraz | phentolamine, phenoxybenzamine, yohimbine, idazoxan, atipamezole, mirtazapine, tolazoline, trazodone, and typical and atypical antipsychotics |
| β1 selective (ADRB1) | Dobutamine | metroprolol, atenolol, acebutolol, bisoprolol, betaxolol, levobetaxolol, esmolol, celiprolol, carteolol, landiolol, oxprenolol, propanolol, practolol, penbutolol, timolol, labetalol, nebivolol, levobunolol, nadolol, pindolol, sotalol, metipranolol, tertatolol, vortioxene |
| β2 selective (ADRB2) | salbutamol, albuterol, bitolterol mesylate, levabuterol, ritodrine, metaproterenol, terbutaline, salmeterol, formoterol, and pirbuterol | butaxamine, acebutolol, timolol, propanolol, levobunolol, carteolol, labetalol, pindolol, oxprenolol, nadolol, metipranolol, penbutolol, tertatolol, sotalol |
| β3 selective (ADRB3) | L-796568, amibegron, solabegron, mirabegron | SR 59230A, arotinolol |

TABLE 10C

DOPAMINE AGONISTS AND ANTAGONISTS

| Receptor | Agonist | Antagonist |
|---|---|---|
| Non-selective | pramipexole, ropinirole, rotigotine, apomorphine, propylnorapomorphine, bromocriptine, cabergoline, ciladopa, dihydrexidine, dinapsoline, doxamthrine, epicriptine, lisuride, pergolide, piribedil, quinagolide, roxindole, dopamine | haloperidol, paliperidone, clozapine, risperidone, olanzapine, quetiapine, ziprasidone, metoclopramide, droperidol, domperidone, amoxapine, clomipramine, trimipramine, choline, melatonin, acepromazine, amisulpride, asenapine, azaperone, benperidol, bromopride, butaclamol, chlorpromazine, clebopride, chlorprothixene, clopenthixol, clocapramine, eticlopride, flupenthixol, fluphenazine, fluspirilene, hydroxyzine, itopride, iodobenzamide, levomepromazine, |

TABLE 10C-continued

DOPAMINE AGONISTS AND ANTAGONISTS

| Receptor | Agonist | Antagonist |
|---|---|---|
| D1 (DRD1) | Fenoldopam, A-86929, dihydrexidine, dinapsoline, dinoxyline, doxanthrine, SKF-81297, SKF-82958, SKF-38393, G-BR-APB, dopexamine | levosulpiride, loxapine, mesoridazine, metopimazine, mosapramine, nafadotride, nemonapride, penfluridol, perazine, perphenazine, pimozide, prochlorperazine, promazine, pipotiazine, raclopride, remoxipride, spiperone, spiroxatrine, stepholidine, sulpiride, sultopride, tetrahydropalmatine, thiethylperazine, thioridazine, thiothixene, tiapride, trifluoperazine, trifluperidol, triflupromazine, thioproperazine, taractan, zotepine, zuclopenthixol, ziprasidone, ANP-010, NGD-94-4 SCH-23,390, SKF-83,959, Ecopipam, Clebopride, Flupenthixol, Zuclopenthixol, Taractan, PSYRX-101, LuAF-35700, GLC-756, ADX10061, Zicronapine |
| D2 (DRD2) | Cabergoline, pergolide, quinelorane, sumanirole, talipexole, piribedil, quinpirole, quinelorane, dinoxyline, dopexamine | Chloroethylnorapomorphine, desmethoxyfallypride, domperidone, eticlopride, fallypride, hydroxyzine, itopride, L-741,626, SV 293, yohimbine, raclopride, sulpiride, paliperidone, penfluridol, quetiapine, lurasidone, risperidone, olanzapine, blonanserin, perphenazine, metoclopramide, trifluoperazine, clebopride, levosulpiride, flupenthixol, haloperidol, thioridazine, alizapride, amisulpride, asenapine, bromopride, bromperidol, clozapine, fluphenazine, perphanazine, loxapine, nemonapride, pericyazine, pipamperone, prochlorperazine, thioproperazine, thiethylperazine, tiapride, ziprasidone, zuclopenthixol, taractan, fluanisone, melperone, molindone, remoxipride, sultopride, ALKS 3831, APD-403, ONC201, pridopidine, DSP-1200, NG-101, TAK-906, ADN-1184, ADN-2013, AG-0098, DDD-016, IRL-626, KP303, ONC-206, PF-4363467, PGW-5, CG-209, ABT-925, AC90222, ACP-005, ADN-2157, CB030006, CLR-136, Egis-11150, Iloperidone, JNJ-37822681, DLP-115, AZ-001, S-33138, SLV-314, Y-931, YKP1358, YK-P1447, APD405, CP-903397, ocaperidone, zicronapine, TPN-902 |
| D3 (DRD3) | Piribedil, quinpirole, captodiame, compound R, R-16, FAUC 54, FAUC 73, PD-128,907, PF-219,061, PF-592,379, CJ-1037, FAUC 460, FAUC 346, cariprazine | Domperidone, FAUC 365, nafadotride, raclopride, PNU-99,194, SB-277011-A, sulpiride, risperidone, YQA14, U99194, SR 21502, levosulpiride, amisulpride, nemonapride, ziprasidone, taractan, sultopride, APD-403, F17464, ONC201, NG-101, TAK-906, ONC-206, PF-4363467, ABT-127, ABT-614, GSK-598809, GSK-618334, S-14297, S-33138, YKP1358, YK-P1447 |
| D4 (DRD4) | WAY-100635, A-412,997, ABT-724, ABT-670, FAUC 316, PD-168, 077, CP-226,269 | A-381393, FAUC 213, L-745,870, L-570,667, ML-398, fananserin, clozapine, PNB-05, SPI-376, SPI-392, Lu-35-138, NGD-94-1 |
| D5 (DRD5) Partial | Dihydrexidine, rotigotine, SKF-83,959, fenoldopam, aplindore, brexpiprazole, aripiprazole, CY-208,243, pardoprunox, phencyclidine, and salvinorin A | SCH 23390 |

TABLE 10D

GABA AGONISTS AND ANTAGONISTS

| Receptor | Agonist | Antagonist |
|---|---|---|
| $GABA_A$ | barbiturates (e.g., allobarbital, amobarbital, aprobarbital, alphenal, barbital, brallobarbital, phenobarbital, secobarbital, thiopental), bamaluzole, GABA, GABOB, gaboxadol, ibotenic acid, isoguvacine, isonipecotic acid, muscimol, phenibut, picamilon, progabide, quisqualamine, SL 75102, thiomuscimol, positive allosteric modulators (PAMs) (e.g., alcohols, such as ethanol and isopropanol; avermectins, such as ivermectin; benzodiazepines, such as diazepam, alprazolam, chlordiazepoxide, clonazepam, flunitrazepam, lorazepam, midazolam, oxazepam, prazepam, brotizolam, triazolam, estazolam, lormetazepam, nitrazepam, temazepam, flurazepam, clorazepate halazepam, prazepam, nimetazepem, adinazolam, and climazolam; bromides, such as potassium bromide; carbamates, such as meprobamate and carisoprodol; chloralose; chlormezanone; chlomethiazole; dihydroergolines, such as ergoloid; etazepine; etifoxine; imidazoles, such as etomidate; imidazopyridines, such as alpidem and necopdiem; kavalactones; loreclezole; neuroactive steroids, such as allogregnanolone, pregnanolone, dihydrodeoxycorticosterone, tetrahydrodeoxycortisosterone, androstenol, androsterone, etiocholanolone, 3α-androstanediol, 5α, 5β, or 3α-dihydroprogesterone, | bicuculline, gabazine, hydrastine, pitrazepin, sinomenine, tutin, thiocolchicoside, metrazol, securinine, gabazine |

TABLE 10D-continued

GABA AGONISTS AND ANTAGONISTS

| Receptor | Agonist | Antagonist |
|---|---|---|
| | and ganaxolone; nonbenzodiazepines, such as zalepon, zolpidem, zopiclone, and eszopiclone; petrichloral; phenols, such as propofol; piperidinediones, such as glutethimide and methyprylon; propanidid; pyrazolopyridines, such as etazolate; pyrazolopyrimidines, such as divaplon and fasiplon; cyclopyrrolones, sush as pagoclone and suproclone; β-cabolines, such as abecarnil and geodecarnil; quinazolinones, such as methaqualone; *Scutellaria* constituents; stiripentol; sulfonylalkanes, such as sulfonomethane, teronal, and trional; Valerian constituents, such as valeric acid and valerenic acid; and gases, such as chloral hydrate, chloroform, homotaurine, diethyl ether, and sevoflurane. | |
| $GABA_B$ | 1,4-butanediol, baclofen, GABA, Gabamide, GABOB, gamma-butyrolactone, gamma-hydroxybutyric acid, gamma-hyrdoxyvaleric acid, gamma-valerolactone, isovaline, lesogaberan, phenibut, picamilon, progabide, homotaurine, SL-75102, tolgabide | CGP-35348, homotaurine, phaclofen, saclofen, and SCH-50911 |
| $GABA_A$-ρ | CACA, CAMP, GABA, GABOB, N4-chloroacetylcytosine arabinoside, picamilon, progabide, tolgabide, and neuroactive steroids, such as allopregnanolone, THDOC, and alphaxolone | gabazine, gaboxadol, isonipecotic acid, SKF-97,541, and (1,2,5,6-Tetrahydropyridin-4-yl)methylphosphinic acid |

TABLE 10E

MUSCARINC AGONISTS AND ANTAGONISTS

| Receptor | Agonist | Antagonist |
|---|---|---|
| Chrm1 | AF102B, AF150(S), AF267B, acetylcholine, carbachol, cevimeline, muscarine, oxotremorine, pilocarpine, vedaclidine, 77-LH-28-1, CDD-0097, McN-A-343, L689,660, and xanomeline | atropine, dicycloverine, hyoscyamine, ipratropium, mamba toxin muscarinic toxin 7 (MT7), olanzapine, oxybutynin, pirenzepine, telenzepine, and tolterodine |
| Chrm2 | acetylcholine, methacholine, iper-8-naph, berbine, and (2S,2'R,3'S,5'R)-1-methyl-2-(2-methyl-1,3-oxathiolan-5-yl)pyrrolidine 3-sulfoxide methyl iodide | atropine, dicycloverine, hyoscyamine, otenzepad, AQRA-741, AFDX-384, thorazine, diphenhydramine, dimenhydrinate, ipratropium, oxybutynin, pirenzepine, methoctramine, tripitramine, gallamine, and tolterodine |
| Chrm3 | acetylcholine, bethanechol, carbachol, L689, 660, oxotremorine, pilocarpine, aceclidine, arecoline, and cevimeline | atropine, dicycloverine, hyoscyamine, alcidium bromide, 4-DAMP, darifenacin, DAU-5884, HL-031,120, ipratropium, J-104, 129, oxybutynin, tiotropium, zamifenacin, and tolterodine |
| Chrm4 | acetylcholine, carbachol, and oxotremorine), and Chrm5 agonists (e.g., acetylcholine, milameline, sabcomeline | AFDX-384, dicycloverine, himbacine, mamba toxin 3, PD-102,807, PD-0298029, and tropicamide |
| Chrm5 | acetylcholine, milameline, sabcomeline | VU-0488130, xanomeline |
| Non-selective | | scopolamine, hydroxyzine, doxylamine, dicyclomine, flavoxate, cyclopentolate, atropine methonitrate, trihexyphenidyl/benzhexol, solifenacin, benzatropine, mebeverine, and procyclidine |

TABLE 10F

NICOTINIC AGONISTS AND ANTAGONISTS

| Receptor | Agonist | Antagonist |
|---|---|---|
| Chrna receptors | choline, acetylcholine, carbachol, methacholine, nicotine, varenicline tartrate, galantamine hydrobromide, suxamethonium chloride (succinylcholine chloride), epibatidine, iobeline, decamethonium, isopronicline/TC-1734/AZD3480 (TC-1734), AZD1446 (TC-6683), TC-5619, TC-5214, MEM 3454 (RG3487), ABT-894, ABT-560, EVP-6124, EVP-4473, PNU-282987, AR-R17779, SSR 189711, JN403, ABBF, PHA-543613, SEN12333, GTS-21/DMXB-A, AZD0328, A-582941, ABT-418, 5-iodo-A-85380, SIB-1765F, ABT-089, and ABT-594 | turbocurarine, bupropion, mecamylamine, 18-methozycoronaridine, hexamethonium, trimethaphan, atraciurium, doxacurium, mivacurium, pancuronium, vecuronium, succinylcholine, dextromethorphan, neramexane, dextrophan, and 3-methoxymorphinan |

TABLE 10G

SEROTONIN AGONISTS AND ANTAGONISTS

| Receptor | Agonist | Antagonist |
|---|---|---|
| $5-HT_{1A}$ | azapirones, such as alnespirone, binosperone, buspirone, enilospirone, etapirone, gepirone, ipsapirone, revospirone, zalospirone, perospirone, tiosperone, umespirone, and tandospirone; 8-OH-DPAT, befiradol, F-15,599, lesopitron, MKC-242, LY-283,284, osemozotan, repinotan, U-92,016-A, RU-24969, 2C-B, 2C-E, 2C-T-2, | pindolol, tertatolol, alprenolol, AV-965, BMY-7,378, cyanopindolol, dotarizine, flopropione, GR-46,611, iodocyanopindolol, isamoltane, lecozotan, mefway, methiothepin, methysergide, MPPF, NAN-190, oxprenolol, pindobind, propanolol, risperidone, robalzotan, SB-649,915, SDZ-216,525, spiperone, spiramide, spiroxatrine, UH-301, WAY-100,135, |

TABLE 10G-continued

SEROTONIN AGONISTS AND ANTAGONISTS

| Receptor | Agonist | Antagonist |
| --- | --- | --- |
| | aripiprazole, asenapine, bacoside, befiradol, brexpiprazole, bufotenin, cannabidiol, and fibanserin | WAY-100,635, and xylamidine |
| $5\text{-HT}_{1B}$ | triptans, such as sumatriptan, rizatriptan, eletriptan, donitripatn, almotriptan, frovatriptan, avitriptan, zolmitriptan, and naratriptan; ergotamine, 5-carboxamidotryptamine, CGS-12066A, CP-93,129, CP-94,253, CP-122,288, CP-135,807, RU-24969, vortioxetine, ziprasidone, and asenapine | methiothepin, yohimbine, metergoline, aripiprazole, isamoltane, AR-A000002, SB-216,641, SB-224,289, GR-127,935, SB-236,057 |
| $5\text{-HT}_{1D}$ | triptans, such as sumatriptan, rizatriptan, and naratriptan; ergotamine, 5-(nonyloxy)tryptaime, 5-(t-butyl)-N-methyltryptamine, CP-286,601, PNU-109,291, PNU-142,633, GR-46611, L-694,247, L-772,405, CP-122,288, and CP-135,807 | ziprasidone, methiothepin, yohimbine, metergoline, ergotamine, BRL-15572, vortioxetine, GR-127,935, LY-310,762, LY-367,642, LY-456,219, and LY-456,220 |
| $5\text{-HT}_{1E}$ | BRL-54443, eletriptan | |
| $5\text{-HT}_{1F}$ | LY-334,370, 5-n-butyryloxy-DMT, BRL-54443, eletriptan, LY-344,864, naratriptan, and lasmiditan | |
| $5\text{-HT}_{2A}$ | 25I-NBOH, 25I-NBOMe, (R)-DOI, TCB-2, mexamine, O-4310, PHA-57378, OSU-6162, 25CN-NBOH, juncosamine, efavirenz, mefloquine, lisuride, and 2C-B | cyproheptadine, methysergide, quetiapine, nefazodone, olanzapine, asenapine, pizotifen, LY-367,265, AMDA, hydroxyzine, 5-MeO-NBpBrT, and niaprazine |
| $5\text{-HT}_{2B}$ | fenfluramine, pergolide, cabergoline, mefloquine, BW-723C86, Ro60-0175, VER-3323, 6-APB, guanfacine, norfenfluramine, 5-MeO-DMT, DMT, mCPP, aminorex, chlorphentermine, MEM, MDA, LSD, psilocin, MDMA | agomelatine, aripiprazole, sarpogrelate, lisuride, tegaserod, metadoxine, RS-127,445, SDZ SER-082, EGIS-7625, PRX-08066, SB-200,646, SB-204,741, SB-206,553, SB-215,505, SB-228,357, LY-266,097, and LY-272,015 |
| $5\text{-HT}_{2C}$ | lorcaserin, lisuride, A-372,159, AL-38022A, CP-809,101, fenfluramine, mesulergine, MK-212, naphthyllisopropylamine, norfenfluramine, ORG-12,962, ORG-37,684, oxaflozane, PNU-22395, PNU-181731, lysergamides, phenethylamines, piperazines, tryptamines, Ro60-0175, vabicaserin, WAY-629, WAY-161,503, WAY-163,909, and YM-348 | agomelatine, CPC, eltoprazine, etoperidone, fluoxetine, FR-260,010, LU AA24530, methysergide, nefazodone, norfluoxetine, O-desmethyltramadol, RS-102,221, SB-200,646, SB-221,284, SB-242,084, SDZ SER-082, tramadol, and trazodone |
| $5\text{-HT}_{2A/2C}$ | | ketanserin, risperidone, trazodone, mirtazapine, clozapine |
| $5\text{-HT}_3$ | 2-methyl-5-HT, alpha-methyltryptamine, bufotenin, chlorophenylbiguanide, ethanol, ibogaine, phenylbiguanide, quipazine, RS-56812, SR-57227, varenicline, and YM-31636 | dolasetron, granisetron, ondansetron, palonosetron, tropisetron, alosetron, cilanosetron, mirtazapine, AS-8112, bantopride, metroclopramide, renzapride, zacopride, mianserin, vortioxetine, clozapine, olanzapine, quetiapine, menthol, thujone, lamotigrine, and 3-tropanyl indole-3-carboxylate |
| $5\text{-HT}_4$ | cisapride, tegaserod, prucalopride, BIMU-8, CJ-033,466, ML-10302, mosapride, renzapride, RS-67506, RS-67333, SL65.1055, zacopride, metoclopramide, and sulpride | piboserod, GR-113,808, GR-125,487, RS-39604, SB-203,186, SB-204,070, and chamomile |
| $5\text{-HT}_{5A}$ | valeronic acid | ASP-5736, AS-2030680, AS-2674723, latrepiridine, risperidone, and SB-699,551 |
| $5\text{-HT}_6$ | EMDT, WAY-181,187, WAY-208,466, N-(inden-5-yl)imidazothiazole-5-sulfonamide, E-6837, E-6801, and EMD-386,088 | ALX-1161, AVN-211, BVT-5182, BVT-74316, cerlapiridine, EGIS-12233, idalopiridine, interpridine, latrepiridine, MS-245, PRX-07034, SB-258,585, SB-271,046, SB-357,134, SB-339,885, Ro 04-6790, |

TABLE 10G-continued

SEROTONIN AGONISTS AND ANTAGONISTS

| Receptor | Agonist | Antagonist |
|---|---|---|
| 5-HT$_7$ | AS-19, 5-CT, 5-MeOT, 8-OH-DAPT, aripiprazole, E-55888, E-57431, LP-12, LP-44, MSD-5a, RA-7, and N,N-Dimethyltryptamine | Ro-4368554, sertindole, olanzapine, asenapine, clozapine, rosa rugosa extract, and WAY-255315 amisulpride, amitriptyline, amoxapine, clomipramine, clozapine, DR-4485, fluphenazine, fluperlapine, ICI 169,369, imipramine, ketanserine, JNJ-18038683, loxapine, lurasidone, LY-215,840, maprotiline, methysergide, mesulergine, mianserin, olanzepine, pimozide, ritanserin, SB-258,719, SB-258,741, SB-269,970, SB-656,104-A, SB-691,673, sertindole, spiperone, tenilapine, TFMPP, vortioxetine, trifluoperazine, ziprasidone, and zotepine |
| Non-selective 5-HT antagonists | | chlorpromazine, cyproheptadine, pizotifen, oxetorone, spiperone, ritanserin, parachlorophenylalanine, metergoline, propranolol, mianserin, carbinoxamine, methdilazine, promethazine, pizotifen, oxatomide, feverfew, fenclonin, and reserpine |

TABLE 10H

GLUATAMATE RECEPTOR AGONISTS AND ANTAGONISTS

| Receptor | Agonist | Antagonist |
|---|---|---|
| Ionotropic (GRIA-14, GRIK1-5, and GRIN1-3B) | AMPA, glutamic acid, ibotenic acid, kainic acid, NMDA, quisqualic acid | AP5, AP7, CPPene, selfotel, HU-211, Huperzine A, gabapentin, remacemide, amantadine, atomoxetine, AZD6765, agmatine, chloroform, dextrallorphan, dextromethorphan, dextrorphan, diphenidine, dizocilpine (MK-801), ethanol, eticyclidine, gacyclidine, ibogaine, ifenprodil, ketamine, kynurenic acid, memantine, magnesium, methoxetamine, nitromemantine, nitrous oxide, PD-137889, perampanel, phencyclidine, rolicyclidine, tenocyclidine, methoxydine, tiletamine, neramexane, eliprodil, etoxadrol, dexoxadrol, WMS-2539, NEFA, delucemine, 8A-PDHQ, aptiganel, rhynchophylline |
| Metabotropic (GRM1-8) | L-AP4, ACPD, L-QA, CHPG, LY-379,268, LY-354,740, ACPT, VU 0155041 | AIDA, fenobam, MPEP, LY-367,385, EGLU, CPPG, MAP4, MSOP, LY-341,495 |
| Glycine antagonists | | rapastinel, NRX-1074, 7-chlorokynurenic acid, 4-chlorokynurenine, 5,7-dichlorokynurenic acid, kynurenic acid, TK-40, 1-aminocyclopropanecarboxylic acid (ACPC), L-phenylalanine, and xenon |

TABLE 10I

HISTAMINE AGONISTS AND ANTAGONISTS

| Receptor | Agonist | Antagonist |
|---|---|---|
| Non-selective | histamine dihydrochloride, HTMT dimaleate, 2-pyridylethlyamine dihydrochloride | |
| H$_1$ | | acrivastine, azelastine, astemizole, bilastine, bromodiphenhydramine, brompheniramine, buclizine, carbinoxamine, cetirizine, cetirizine dihydrochloride, clemastine fumarate, clemizole hydrochloride, chlorodiphenhydramine, chlorphenamine, chlorpromazine, clemastine, cyclizine, cyproheptadine, dexbrompheniramine, dexchlorpheniramine, dimenhydrinate, dimethindene maleate, dimetindene, |

TABLE 10I-continued

HISTAMINE AGONISTS AND ANTAGONISTS

| Receptor | Agonist | Antagonist |
| --- | --- | --- |
| | | diphenhydramine, diphenhydramine hydrochloride, doxepin hydrochloride, doxylamine, ebastine, embramine, fexofenadine, fexofenadine hydrochloride, hydroxyzine, ketotifen fumarate, loratadine, meclizine, meclizine dihydrochloride, mepyramine maleate, mirtazapine, olopatadine, olopatadine hydrochloride, orphenadrine, phenindamine, pheniramine, phenyltoloxamine, promethazine, quetiapine, rupatadine, terfenadine, tripelennamine, zotepine, trans-triprolidine hydrochloride, and triprolidine |
| $H_1$ inverse agonists | | cetirizine, levocetirizine, desloratadine, and pyrilamine |
| $H_2$ | betazole, impromidine, dimaprit dihydrochloride, and amthamine dihyrdobromide | aminopotentidine, cimetidine, famotidine, ICI 162,846, lafutidine, nizatidine, ranitidine, ranitidine hyrdochloride, roxatidine, zolantadine dimaleate, and toitidine |
| $H_3$ | imetit dihydropbromide, immepip dihyrdrobromide, immethridine dihydrobromide, α-Methylhistamine dihydrobromide, N-methylhistamine dihydrochloride, proxyfan oxalate, and betahistine | clobenpropit, clobenpropit dihydrobromide, A 3314440 dihyrdochloride, BF 2649 hydrochloride, carcinine ditrifluoroacetate, ABT-239, ciprofaxin, conessine, GT 2016, A-349,821, impentamine dihydrobromide, iodophenpropit dihydrobromide, JNJ 10181457 dihydrochloride, JNJ 5207852 dihydrochloride, ROS 234 dioxalate, SEN 12333, VUF 5681 dihydrobromide, and thioperamide |
| $H_4$ | imetit dihydropbromide, immepip dihyrdrobromide, 4-methylhistamine dihydrochloride, clobenpropit dihydrobromide, VUF 10460, and VUF 8430 dihydrobromide | thioperamide, JNJ 7777120, A 943931 dihydrochloride, A 987306, JNJ 10191584 maleate, and VUF-6002 |

TABLE 10J

CANNABINOID AGONISTS AND ANTAGONISTS

| Receptor | Agonist | Antagonist |
| --- | --- | --- |
| Cannabinoid receptor (non-selective) | Anandamide, N-Arachidonoyl dopamine, 2-Arachidonoylglycerol (2-AG), 2-Arachidonyl glyceryl ether, Δ-9-Tetrahydrocannabinol, EGCG, Yangonin, AM-1221, AM-1235, AM-2232, UR-144, JWH-007, JWH-015, JWH-018, ACEA, ACPA, arvanil, CP 47497, DEA, leelamine, methanandamide, NADA, noladin ether, oleamide, CB 65, GP-1a, GP-2a, GW 405833, HU 308, JWH-133, L-759,633, L-759,656, LEI 101, MDA 19, and SER 601 | |
| $CB_1$ receptor | ACEA, ACPA, RVD-Hpα, (R)-(+)-methanandamide | rimonabant, cannabidiol, Δ$^9$-tetrahydrocannabivarin (THCV), taranabant, otenabant, surinabant, rosonabant, SLV-319, AVE1625, V24343, AM 251, AM 281, AM 6545, hemopressin, LY 320135, MJ 15, CP 945598, NIDA 41020, PF 514273, SLV 319, SR 1141716A, and TC-C 14G |

TABLE 10J-continued

CANNABINOID AGONISTS AND ANTAGONISTS

| Receptor | Agonist | Antagonist |
|---|---|---|
| CB$_2$ receptor | CB 65, GP 1a, GP 2a, GW 405833, HU 308, JWH 133, L-759,656, L-759,633, SER 601, LEI 101 | cannabidiol, $\Delta^{9-}$ tetrahydrocannabivarin (THCV), AM 630, COR 170, JTE 907, and SR 144528 |

TABLE 10K

PURINERGIC RECEPTOR AGONISTS AND ANTAGONISTS

| Receptor | Agonist | Antagonist |
|---|---|---|
| ADORA1 (P1 adenosine receptor) | Adenosine, N6-Cyclopentyladenosine, N6-3-methoxyl-4-hydroxybenzyl adenine riboside (B2), CCPA, tecadenoson, selodenoson, Certain Benzodiazepines and Barbiturates, 2'-MeCCPA, GR 79236, and SDZ WAG 994 | Caffeine, theophylline, 8-Cyclopentyl-1,3-dimethylxanthine (CPX), 8-Cyclopentyl-1,3-dipropylxanthine (DPCPX), 8-Phenyl-1,3-dipropylxanthine, bamifylline, BG-9719, BG09928, FK-453, FK838, rolofylline, N-0861, and PSB 36 |
| ADORA2A (P1 adenosine receptor) | Adenosine, N6-3-methoxyl-4-hydroxybenzyl adenine riboside (B2), YT-146, DPMA, UK-423,097, limonene, NECA, CV-3146, binodenoson, ATL-146e, CGS-21680, and Regadenoson | Caffeine, theophylline, istradefylline, SCH-58261, SCH-442,416, ATL-444, MSX-3, preladenant, SCH-412,348, VER-6623, VER-6947, VER-7835, vipadenant, and ZM-241,385 |
| ADORA2B (P1 adenosine receptor) | Adenosine, 5'-N-ethylcarboxamidoadenosine, BAY 60-6583, LUF-5835, NECA, (S)-PHPNECA, and LUF-5845 | Caffeine, theophylline, CVT-6883, ATL-801, compound 38, MRS-1706, MRS-1754, OSIP-339,391, PSB-603, PSB-0788, and PSB-1115 |
| ADORA3 (P1 adenosine receptor) | Adenosine, 2-(1-Hexynyl)-N-methyladenosine, CF-101 (IB-MECA), CF-102, 2-Cl-IB-MECA, CP-532,903, inosine, LUF-6000, and MRS-3558 | Caffeine, theophylline, MRS-1191, MRS-1220, MRS-1334, MRS-1523, MRS-3777, MRE3008F20, MRE3005F20, OT-7999, SSR161421, KF-26777, PSB-10, PSB-11, and VUF-5574 |
| P2Y receptor | ATP, ADP, UTP, UDP, UDP-glucose, 2-methylthioladenosine 5' diphosphate (2-MeSADP), lysophosphatidic acid, PSB 1114, PSB 0474, NF 546, MRS 2365, MRS 2690, MRS 2693, MRS 2768, MRS 2905, MRS 2957, MRS 4062, and denufosol (P2Y$_2$ agonist) | clopidogrel, elinogrel, prasugrel, ticlopidine, ticagrelor, AR-C 118925XX, AR-C 66096, AR-C 69931, AZD 1283, MRS 2179, MRS 2211, MRS 2279, MRS 2500, MRS 2578, NF 157, NF 340, PPADS, PPTN hydrochloride, PSD 0739, SAR 216471, and suramin |
| P2X receptor | ATP | A 438079, A 740003, A 804598, A 839977, AZ 10606120, AZ 11645373, 5-BDBD, BX 430, Evans Blue, JNJ 47965567, KN-62, NF 023, NF 110, NF 157, NF 279, NF 449, PPADS, iso-PPADS, PPNDS, Ro 0437626, Ro 51, RO-3, TC-P 262, suramin, TNP-ATP, and P2X$_7$ antagonists NF279, calmidazolium, and KN-62 |

TABLE 11

NEUROTRANSMISSION MODULATORS

| Type | Modulators |
|---|---|
| Norepinephrine reuptake inhibitors (increase adrenergic neurotransmission) | amedalin, atomoxetine, CP-39,332, daledalin, edivoxetine, esreboxetine, lortalamine, nisoxetine, reboxetine, talopram, talsupram, tandamine, viloxazine, bupropion, ciclazindol, manifaxine, maprotiline, radafaxine, tapentadol, teniloxazine, protriptyline, nortriptyline, and desipramine |
| Norepineprhine-dopamine reuptake inhibitors (increase adrenergic and dopamine neurotransmission) | amineptine, bupropion, desoxypipradrol, dexmethylphenidate, difemetorex, diphenylprolinol, ethylphenidate, fencamfamine, fencamine, |

TABLE 11-continued

| NEUROTRANSMISSION MODULATORS | |
|---|---|
| Type | Modulators |
| | lefetamine, methylenedioxypyrovalerone, methylphenidate, nomifensine, O-2172, oxolinic acid, pipradrol, prolintane, pyrovalerone, tametraline, and WY-46824 |
| Serotonin-norepinephrine-dopamine reuptake inhibitors (SNDRIs) and serotonin-norepinephrine reuptake inhibitors (SNRIs) (increase adrengergic, dopamine, and serotonin neurotransmission) | mazindol, nefazodone, sibutramine, venlafaxine, esketamine, duloxetine, ketamine, phencyclidine, tripelennamine, mepiprazole, amitifadine, AN788, ansofaxine, centanafadine, atomoxetine, desvenlafaxine, milnacipran, levomilnacipran, dasotraline, Lu AA34893, Lu AA37096, NS-2360, tedatioxetine, tesofensine, bicifadine, BMS-866,949, brasofensine, diclofensine, DOV-216,303, EXP-561, liafensine, NS-2359, RG-7166, SEP-227,162, SEP-228,425, SEP-228,432, naphyrone, 3,3-Diphenylcyclobutanamine, 3,4-Dichlorotametraline, D-161, desmethylsertraline, DMNPC, DOV-102,677, fezolamine, GSK1360707F, indatraline, JNJ-7925476, JZ-IV-10, JZAD-IV-22, LR-5182, methylnaphthidate, MI-4, PRC200-SS, PRC050, PRC025, SKF-83,959, TP1, phenyltropanes (e.g., WF-23, dichloropane, and RTI-55), *Ginkgo biloba* extract, St John''s Wort, hyperforin, adhyperforin, and uliginosin B |
| Dopamine reuptake inhibitors (increase dopamine neurotransmission) | Dopamine reuptake inhbiitors (e.g., altropane, amfonelic acid, amineptine, BTCP, 30-PEP, DBL-583, difluoropine, GBR-12783, GBR-12935, GBR-13069, GBR-13098, GYKI-52895, lometopane, methylphenidate, ethylphenidate, modafinil, armodafinil, RTI-229, vanoxerine, adrafinil, benztropine, bupropion, fluorenol, medifoxamine, metaphit, rimcazole, venlafaxine, *Chaenomeles speciosa*, and oroxylin A), dopamine releasing agents (e.g., p-Tyramine), dextroamphetamine, lisdexamfetamine, dexmethylphenidate, and cathinone |
| Dopamine prodrugs (increase dopamine neurotransmission) | Levopoda, docarpamine |
| GABA reuptake inhibitors (increase GABA neurotransmission) | CL-996, deramciclane, gabaculine, guvacine, nipecotic acid, NNC-711, NNC 05-2090, SKF-89976A, SNAP-5114, tiagabine, and hyperforin |
| GABA analogs (increase GABA neurotransmission) | gabapentin, butyric acid, valproic acid, valpromide, valnoctamide, 3-hydroxybutanal, GHB, sodium, oxybate, aceburic acid, GBL, GHBAL, GHV, GVL, GHC, GCL, HOCPCA, UMB68, pregabalin, tolibut, phaclofen, sacolfen, arecaidine, gaboxadol, isonipecotic acid, 3-Methyl-GABA, AABA, BABA, DAVA, GAVA, Glutamic acid, hopantenic acid, piracetam, and vigabatrin |
| GABA prodrugs (increase GABA neurotransmission) | L-Glutamine, N-Isonicotinoyl-GABA, picamilon, progabide, tolgabide |
| Acetylcholinesterase inhibitors (increase nicotinic and muscarinic neurotransmission) | carbamates, physostigmine, neostigmine, pyridostigmine, ambenonium, demecarium, rivastigmine, phenanthrene derivatives, galantamine, caffeine, rosmarinic acid, alpha-pinene, piperidines, donepezil, tacrine, edrophonium, Huperzine A, ladostigil, ungeremine, lactucopicrin, dyflos, echothiophate, parathion, and quasi-irreversible acetylcholinesterase inhibitors |
| Serotonin reuptake inhibitors (increase serotonin neurotransmission) | alaproclate, cericlamine, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, didesmethylcitalopram, seproxetine ((S)-norfluoxetine), desvenlafaxine, cianopramine, litoxetine, lubazodone, SB-649,915, trazodone, vilazodone, vortioxetine, dextromethorphan, dextropropoxyphene, dimenhydrinate, diphenhydramine, mepyramine (pyrilamine), mifepristone, delucemine, mesembrenone, mesembrine, roxindole, duloxetine, levomilnacipran, milnacipran, dapoxetine, sibutramine, chlorpheniramine, dextropmethorphan, and methadone |
| Serotonin releasing agents (increase serotonin neurotransmission) | chlorphentermine, cloforex, dexfenfluramine, etolorex, fenfluramine, flucetorex, indeloxazine, |

TABLE 11-continued

NEUROTRANSMISSION MODULATORS

| Type | Modulators |
|---|---|
| | levofenfluramine, tramadol, carbamazepine, amiflamine (FLA-336), viqualine (PK-5078), 2-Methyl-3,4-methylenedioxyamphetamine (2-Methyl-MDA), 3-Methoxy-4-methylamphetamine (MMA), 3-Methyl-4,5-methylenedioxyamphetamine (5-Methyl-MDA), 3,4-Ethylenedioxy-N-methylamphetamine (EDMA), 4-Methoxyamphetamine (PMA), 4-Methoxy-N-ethylamphetamine (PMEA), 4-Methoxy-N-methylamphetamine (PMMA), 4-Methylthioamphetamine (4-MTA), 5-(2-Aminopropyl)-2,3-dihydrobenzofuran (5-APDB), 5-Indanyl-2-aminopropane (IAP), 5-Methoxy-6-methylaminoindane (MMAI), 5-Trifluoromethyl-2-aminoindane (TAI), 5,6-Methylenedioxy-2-aminoindane (MDAI), 5,6-Methylenedioxy-N-methyl-2-aminoindane (MDMAI), 6-Chloro-2-aminotetralin (6-CAT), 6-Tetralinyl-2-aminopropane (TAP), 6,7-Methylenedioxy-2-aminotetralin (MDAT), 6,7-Methylenedioxy-N-methyl-2-aminotetralin (MDMAT), N-Ethyl-5-trifluoromethyl-2-aminoindane (ETAI), N-Methyl-5-indanyl-2-aminopropane, aminorex, MDMA, MDEA, MDA, MBDB, and tryptamines, such as DMT, αMT, 5MeO-NMT, NMT, NETP, Dimethyl-Serotonin, 5MeO-NET, αET and αMT |
| Excitatory amino acid reuptake inhibitors (increase Glutamate receptor neurotransmission) | didydrokanic acid, WAY-213,613, L-trans-2,4-PDC, amphetamine, and L-Theanine |
| Glycine reuptake inhibitors (increase Glutamate receptor neurotransmission) | bitopertin, Org 24598, Org 25935, ALX-5407, sacrosine, Org 25543, and N-arachidonylglycerine |
| Histidine decarboxylase inhibitors (decrease histamine neurotransmission) | Tritoqualine, catechin |
| Endocannabinoid enhancers (increase cannabinoid neurotransmission) | AM404, fatty acid amide hydrolase inhibitors (e.g., AM374, ARN2508, BIA 10-2472, BMS-469908, CAY-10402, JNJ-245, JNJ-1661010, JNJ-28833155, JNJ-40413269, JNJ-42119779, JNJ-42165279, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597, URB694, URB937, VER-156084, and V-158866 |
| Monoacylglycerol lipase inhibitors (increase cannabinoid neurotransmission) | N-arachidonoyl maleimide, JZL184 |
| Endocannabinoid transporter inhibitors (increase cannabinoid neurotransmission) | SB-FI-26 |
| Endocannabinoid reuptake inhibitors (increase cannabinoid neurotransmission) | AM404, AM1172, LY-2183240, O-2093, OMDM-2, UCM-707, VDM-11, guineensine, ETI-T-24_B_I, WOBE437, and RX-055 |
| Adenosine uptake inhibitors (increase purinergic neurotransmission) | cilostazol, dilazep, and dipyramidole |
| Nucleoside transporter inhibitors (increase purinergic neurotransmission) | 8MDP, Decynium 22, 5-iodotubercidin, NBMPR, and TC-T 6000 |

In some embodiments, the neurotransmission blocker is a neurotoxin listed in Table 12, or a functional fragment or variant thereof. Neurotoxins include, without limitation, convulsants, nerve agents, parasympathomimetics, and uranyl compounds. Neurotoxins may be bacterial in origin, or fungal in origin, or plant in origin, or derived from a venom or other natural product. Neurotoxins may be synthetic or engineered molecules, derived de novo or from a natural product. Suitable neurotoxins include but are not limited to botulinum toxin and conotoxin. Exemplary neurotoxins are listed in Table 12.

TABLE 12

| NEUROTOXINS | NEUROTOXINS |
|---|---|
| 2,4,5-Trihydroxyamphetamine | Grayanotoxin |
| 2,4,5-Trihydroxymethamphetamine | Hainantoxin |

TABLE 12-continued

| NEUROTOXINS | NEUROTOXINS |
|---|---|
| 3,4-Dichloroamphetamine | Halcurin |
| 5,7-Dihydroxytryptamine | Hefutoxin |
| 5-Iodowillardiine | Helothermine |
| Ablomin | Heteroscodratoxin-1 |
| Aconitine | Histrionicotoxin |
| Aconitum | Homoquinolinic acid |
| Aconitum anthora | Hongotoxin |
| AETX | Huwentoxin |
| Agelenin | Ibotenic acid |
| Agitoxin | Ikitoxin |
| Aldrin | inhibitor cystine knot |
| Alpha-Methyldopamine | Jingzhaotoxin |
| Alpha-neurotoxin | Kainic acid |
| Altitoxin | Kaliseptine |
| Anatoxin-a | Kappa-bungarotoxin |
| Androctonus australis hector insect toxin | Kodaikanal mercury poisoning |

TABLE 12-continued

NEUROTOXINS
NEUROTOXINS

| | |
|---|---|
| Anisatin | Kurtoxin |
| Anthopleurin | Latrotoxin |
| Antillatoxin | Lq2 |
| Anuroctoxin | Maitotoxin |
| Apamin | Margatoxin |
| Arum italicum | Maurotoxin |
| Arum maculatum | Mercury (element) |
| Babycurus toxin 1 | Methanol |
| Batrachotoxin | Methiocarb |
| BDS-1 | MPP+ |
| Bestoxin | MPTP |
| Beta-Methylamino-L-alanine | Nemertelline |
| BgK | Neosaxitoxin |
| Birtoxin | Nicotine |
| BmKAEP | N-Methylconiine |
| BmTx3 | Oenanthotoxin |
| BotIT2 | Oxalyldiaminopropionic acid |
| BotIT6 | Oxidopamine |
| Botulinum toxin | Oxotoxin |
| Brevetoxin | Pahutoxin |
| Bukatoxin | Palytoxin |
| Butantoxin | Pandinotoxin |
| Calcicludine | Para-Bromoamphetamine |
| Calciseptine | Para-Chloroamphetamine |
| Calitoxin | Para-Chloromethamphetamine |
| Caramboxin | Para-Iodoamphetamine |
| Carbon disulfide | Penitrem A |
| CgNa toxin | Phaiodotoxin |
| Charybdotoxin | Phenol |
| Cicutoxin | Phoneutria nigriventer toxin-3 |
| Ciguatoxin | Phrixotoxin |
| Cll1 | Polyacrylamide |
| Clostridium botulinum | Poneratoxin |
| Conantokins | Psalmotoxin |
| Conhydrine | Pumiliotoxin |
| Coniine | Quinolinic acid |
| Conotoxin | Raventoxin |
| Contryphan | Resiniferatoxin |
| Cssll | Samandarin |
| CSTX | Saxitoxin |
| Curare | Scyllatoxin |
| Cyanide poisoning | Sea anemone neurotoxin |
| Cylindrospermopsin | Slotoxin |
| Cypermethrin | SNX-482 |
| Delta atracotoxin | Stichodactyla toxin |
| Dendrotoxin | Taicatoxin |
| Dieldrin | Taipoxin |
| Diisopropyl fluorophosphates | Tamapin |
| Dimethylmercury | Tertiapin |
| Discrepin | Tetanospasmin |
| Domoic acid | Tetraethylammonium |
| Dortoxin | Tetramethylenedisulfotetramine |
| DSP-4 | Tetrodotoxin |
| Ergtoxin | Tityustoxin |
| Falcarinol | Tricresyl phosphate |
| Fenpropathrin | TsIV |
| Gabaculine | Vanillotoxin |
| Ginkgotoxin | Veratridine |
| Grammotoxin | |

Antibodies

Neurotransmission modulators also include antibodies that bind to neurotransmitters or neurotransmitter receptors listed in Tables 8 and 9 and decrease neurotransmission. These antibodies include blocking and neutralizing antibodies. Antibodies to neurotransmitters or neurotransmitter receptors listed in Tables 8 and 9 can be generated by those of skill in the art using well established and routine methods.

Neuronal Growth Factor Modulators

In some embodiments, the SERCA pump inhibitor is administered with a neuronal growth factor modulator (e.g., an agent that decreases or increases neurogenic/axonogenic signals, e.g., a neuronal growth factor or neuronal growth factor mimic, or an agonist or antagonist of a neuronal growth factor or neuronal growth factor receptor). For example, the neuronal growth factor modulator is a neuronal growth factor listed in Table 13, e.g., a neuronal growth factor having the sequence referenced by accession number or Entrez Gene ID in Table 13, or an analog thereof, e.g., a sequence having at least 75%, 80%, 85%, 90%, 90%, 98%, 99% identity to the sequence referenced by accession number or Entrez Gene ID in Table 13. Neuronal growth factor modulators also include agonists and antagonists of neuronal growth factors and neuronal growth factor receptors listed in Table 13. A neuronal growth factor modulator may increase or decrease neurogenesis, neuronal growth, neuronal differentiation, neurite outgrowth, synapse formation, synaptic maturation, synaptic refinement, or synaptic stabilization. Neuronal growth factor modulators regulate tissue innervation (e.g., innervation of a tumor) and the formation of synaptic connections between two or more neurons and between neurons and non-neural cells (e.g., between neurons and cancer cells). A neuronal growth factor modulator may block one or more of these processes (e.g., through the use of antibodies that block neuronal growth factors or their receptors) or promote one or more of these processes (e.g., through the use of neuronal growth factors or analogs thereof). Neuronal growth factor modulators can increase or decrease one of the above-mentioned processes by 10%, 20%, 30%, 40%, 50%, 60%, 70%, 80%, 90%, 95%, 98%, 200%, 500% or more.

In some embodiments, the neuronal growth factor modulator is one that increases neurogenic/axonogenic signals, e.g., the method includes administering to the subject or contacting a cell with a neuronal growth factor modulator in an amount and for a time sufficient to increase neurogenesis or axonogenesis. For example, the neuronal growth factor modulator that leads to an increase in neurogenesis or axonogenesis is a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 13. Receptors for these factors may also be targeted, as well as downstream signaling pathways including Jak-Stat inducers, and cell cycle and MAPK signaling pathways. In some embodiments, the neuronal growth factor modulator increases neurogenesis, axonogenesis or any of the processes mentioned above by administering, locally delivering, or stabilizing a neuronal growth factor listed in Table 13, or by upregulating, agonizing, or stabilizing a neuronal growth factor receptor listed in Table 13. In some embodiments, the neuronal growth factor modulator increases neurogenesis, axonogenesis or any of the processes mentioned above by stabilizing, agonizing, overexpressing, or upregulating a signaling protein encoded by a gene that is downstream of a neuronal growth factor. In some embodiments, the neuronal growth factor modulator increases neurogenesis, axonogenesis or any of the processes mentioned above by stabilizing, overexpressing, or upregulating a synaptic or structural protein. Neurogenesis, axonogenesis, neuronal growth, neuronal differentiation, neurite outgrowth, synapse formation, synaptic maturation, synaptic refinement, or synaptic stabilization can be increased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, or synaptic stabilization can be increased in the subject between 5-20%, between 5-50%, between 10-50%, between 20-80%, between 20-70%.

In some embodiments, the neuronal growth factor modulator decreases neurogenic/axonogenic signals, e.g., the method includes administering to the subject or contacting a cell with a neuronal growth factor modulator in an amount and for a time sufficient to decrease neurogenesis, axonogenesis, or innervation. For example, the neuronal growth factor modulator that leads to a decrease in neurogenesis or axonogenesis is a blocking or neutralizing antibody against a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 13. Receptors for these factors can also be targeted, as well as downstream signaling pathways including Jak-Stat inducers, and cell cycle and MAPK signaling pathways. In some embodiments, the neuronal growth factor modulator decreases neurogenesis, axonogenesis or any of the processes mentioned above by sequestering, blocking, antagonizing, degrading, or down-regulating a neuronal growth factor or a neuronal growth factor receptor listed in Table 13. In some embodiments, the neuronal growth factor modulator decreases neurogenesis, axonogenesis or any of the processes mentioned above by blocking or antagonizing a signaling protein that is downstream of a neuronal growth factor. In some embodiments, the neuronal growth factor modulator decreases neurogenesis, axonogenesis or any of the processes mentioned above by blocking, disrupting, or antagonizing a synaptic or structural protein. Neurogenesis, axonogenesis, neuronal growth, neuronal differentiation, neurite outgrowth, synapse formation, synaptic maturation, synaptic refinement, synaptic stabilization, or tissue innervation can be decreased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, synaptic stabilization, or tissue innervation can be decreased in the subject between 5-20%, between 5-50%, between 10-50%, between 20-80%, between 20-70%. Neuronal growth factor blockers can be administered in any of the modalities described herein (e.g., antibody, small molecule, nucleic acid, polypeptide, or viral vector).

In some embodiments, the neuronal growth factor modulator decreases the number of nerves in an affected tissue. For example, the subject has cancer (e.g., the subject has a highly innervated tumor). For example, the neuronal growth factor blocker is administered in an amount and for a time sufficient to decrease neurogenesis/axonogenesis.

Neuronal growth factor blockers include antibodies that bind to neuronal growth factors or neuronal growth factor receptors and decrease their signaling (e.g., blocking antibodies). Exemplary neuronal growth factor blocking antibodies are listed below in Table 14. Antibodies to neuronal growth factors listed in Table 14 can also be generated by those of skill in the art using well established and routine methods.

TABLE 13

NEURONAL GROWTH FACTORS

| Gene | Type | Accession Number | Entrez Gene ID |
|---|---|---|---|
| ARTN | Ligand | Q5T4W7 | 9048 |
| BDNF | Ligand | P23560 | 627 |
| BDNF-AS | Ligand | | 497258 |
| BEX1 | Signaling | Q9HBH7 | 55859 |
| BEX3 | Signaling | O00994 | 27018 |
| CD34 | Receptor | P28906 | 947 |
| CDNF | Ligand | Q49AH0 | 441549 |
| CNTF | Ligand | P26441 | 1270 |
| CNTFR | Receptor | P26992 | 1271 |
| CRLF1 | Receptor | O75462 | 9244 |
| CSPG5 | Ligand | O95196 | 10675 |
| DCLK1 | Signaling | O15075 | 9201 |
| DISC1 | Signaling | Q9NRI5 | 27185 |
| DNAJC5 | Signaling | Q9H3Z4 | 80331 |
| DPYSL2 | Signaling | Q16555 | 1808 |
| DVL1 | Signaling | O14640 | 1855 |
| EFNA5 | Ligand | P52803 | 1946 |
| EGR3 | Signaling | Q06889 | 1960 |
| ENO2 | Signaling | P09104 | 2026 |
| EphA1 | Receptor | P21709 | 2041 |
| EphA10 | Receptor | Q5JZY3 | 284656 |
| EphA2 | Receptor | P29317 | 1969 |
| EphA3 | Receptor | P29320 | 2042 |
| EphA4 | Receptor | P29317 | 2043 |
| EphA5 | Receptor | P54756 | 2044 |
| EphA6 | Receptor | Q9UF33 | 285220 |
| EphA7 | Receptor | Q15375 | 2045 |
| EphA8 | Receptor | P29322 | 2046 |
| EphB1 | Receptor | P54762 | 2047 |
| EphB2 | Receptor | P29323 | 2048 |
| EphB3 | Receptor | P54753 | 2049 |
| EphB4 | Receptor | P54760 | 2050 |
| EphB6 | Receptor | O15197 | 2051 |
| ETBR2 | Receptor | O60883 | 9283 |
| FSTL4 | Receptor | Q6MZW2 | 23105 |
| GDNF | Ligand | P39905 | 2668 |
| GFRA1 | Receptor | P56159 | 2674 |
| GFRA2 | Receptor | O00451 | 2675 |
| GFRA3 | Receptor | O60609 | 2676 |
| GFRA4 | Receptor | Q9GZZ7 | 64096 |
| GPR37 | Receptor | O15354 | 2861 |
| GPRIN1 | Signaling | Q7Z2K8 | 114787 |
| GPRIN2 | Signaling | O60269 | 9721 |
| GPRIN3 | Signaling | Q6ZVF9 | 285513 |
| GRB2 | Signaling | P62993 | 2885 |
| GZF1 | Signaling | Q9H116 | 64412 |
| IFNA1 | Ligand | P01562 | 3439 |
| IGF1 | Ligand | P05019 | 3479 |
| IGF2 | Ligand | P01344 | 3481 |
| IL11RA | Receptor | Q14626 | 3590 |
| IL1B | Ligand | P01584 | 3553 |
| IL3 | Ligand | P08700 | 3562 |
| IL4 | Ligand | P05112 | 3565 |
| IL6 | Ligand | P05231 | 3569 |
| IL6R | Receptor | P08887 | 3570 |
| IL6ST | Signaling | P40189 | 3572 |
| INS | Ligand | P01308 | 3630 |
| L1CAM | Signaling | P32004 | 3897 |
| LIF | Ligand | P15018 | 3976 |
| LIFR | Receptor | P42702 | 3977 |
| MAGED1 | Signaling | Q9Y5V3 | 9500 |
| MANF | Ligand | P55145 | 7873 |
| NDNF | Ligand | Q8TB73 | 79625 |
| NENF | Ligand | Q9UMX5 | 29937 |
| NENFP1 | Ligand | | 106480294 |
| NENFP2 | Ligand | | 100129880 |
| NENFP3 | Ligand | | 106481703 |
| NGF | Ligand | P01138 | 4803 |
| NGFR | Receptor | P08138 | 4804 |
| NRG1 | Ligand | Q02297 | 3084 |
| NRP1 | Receptor | O14786 | 8829 |
| NRTN | Ligand | Q99748 | 902 |
| NTF3 | Ligand | P20783 | 4908 |
| NTF4 | Ligand | P34130 | 4909 |
| NTRK1 | Receptor | P04629 | 4914 |

TABLE 13-continued

NEURONAL GROWTH FACTORS

| Gene | Type | Accession Number | Entrez Gene ID |
|---|---|---|---|
| NTRK2 | Receptor | Q16620 | 4915 |
| NTRK3 | Receptor | Q16288 | 4916 |
| PDPK1 | Signaling | O15530 | 5170 |
| PEDF | Ligand | P36955 | 5176 |
| PLEKHH3 | Signaling | Q7Z736 | 79990 |
| PSAP | Ligand | P07602 | 5660 |
| PSEN1 | Signaling | P49768 | 5663 |
| PSPN | Ligand | O70300 | 5623 |
| PTN | Ligand | P21246 | 5764 |
| RELN | Ligand | P78509 | 5649 |
| RET | Signaling | P07949 | 5979 |
| ROR1 | Receptor | Q01973 | 4919 |
| ROR2 | Receptor | Q01974 | 4920 |
| RPS6KA3 | Signaling | P51812 | 6197 |
| SDC3 | Receptor | O75056 | 9672 |
| SEMA3E | Receptor | O15041 | 9723 |
| SERPINE2 | Ligand | P07093 | 5270 |
| SERPINF1 | Ligand | P36955 | 5176 |
| SHC1 | Signaling | P51812 | 6464 |
| SNTG1 | Biosynthesis | P07602 | 54212 |
| SORCS1 | Receptor | O75056 | 114815 |
| SORCS2 | Receptor | O15041 | 57537 |
| SORCS3 | Receptor | P07093 | 22986 |
| SORT1 | Receptor | Q99523 | 6272 |
| SULF1 | Signaling | Q8IWU6 | 23213 |
| SULF2 | Signaling | Q8IWU5 | 55959 |
| TGFB1 | Ligand | P01137 | 7040 |
| TGFB2 | Ligand | P61812 | 7042 |
| TGFB3 | Ligand | P10600 | 7043 |
| TMEM158 | Receptor | Q8WZ71 | 25907 |
| TNF | Ligand | P01375 | 7124 |
| TPM3 | Receptor | P06753 | 7170 |
| VEGFA | Ligand | P15692 | 7422 |
| VEGFB | Ligand | P49765 | 7423 |
| VGF | Ligand | O15240 | 7425 |
| XCR1 | Receptor | P46094 | 2829 |
| ZN274 | Signaling | Q96GC6 | 10782 |

TABLE 14

NEURONAL GROWTH FACTOR ANTIBODIES

| Neuronal Growth Factor | Antibody | Company |
|---|---|---|
| BDNF | 38B8 (agonist antibody) | Pfizer |
| BDNF | 29D7 (agonist antibody) | Pfizer |
| EphA3 | KB004 | KaloBios Pharmaceuticals, Inc. |
| IFNA1 | Faralimomab | Creative Biolabs |
| IFNA1 | Sifalimumab (MEDI-545) | MedImmune |
| IFNA1 | Rontalizumab | Genentech |
| IGF | Figitumumab (CP-751,871) - an IGR-1R MAb | Pfizer |
| IGF | SCH717454 (Robatumamab, inhibits IGF initiated phosphorylation) | Merck |
| IGF | Cixutumumab (IGF-1R antibody) | Eli Lilly |
| IGF | Teprotumumab (IGF-1R blocking antibody) | Genmab/Roche |
| IGF-2 | Dusigitumab | MedImmune/AstraZeneca |
| IGF-2 | DX-2647 | Dyax/Shire |
| IGF | Xentuzumab | Boehringer Ingelheim/Eli Lilly |
| IGF | Dalotuzumab (IGFR1 blocking antibody) | Merck & Co. |
| IGF | Figitumumab (IGFR1 blocking antibody) | Pfizer |
| IGF | Ganitumab (IGFR1 blocking antibody) | Amgen |
| IGF | Robatumumab (IGFR1 blocking antibody) | Roche/Schering-Plough |
| IL1B | Canakinumab | Novartis |
| IL1B | APX002 | Apexigen |
| IL1B | Gevokizumab | XOMA |
| IL4 | Pascolizumab | GlaxoSmithKline |
| IL4 | Dupilumab | Regeneraon/Sanofi |
| IL6 | Siltuximab | Janssen Biotech, Inc. |
| IL6 | Olokizumab | UCB/R-Pharm |
| IL6 | Elsilimomab | Orphan Pharma International |
| IL6 | Sirukumab | Centocor |
| IL6 | Clazakizumab | Bristol Myers Squib/Alder Biopharmaceuticals |
| IL6 | Gerilimzumab (ARGX-109) | arGEN-X/RuiYi |
| IL6 | FE301 | Ferring Pharmaceuticals |
| IL6 | FM101 | Femta Pharmaceuticals |
| IL-6R | Sarilumab (directed against IL6R) | Regeneron/Sanofi |
| IL-6R | Tocilizumab | Hoffmann-La Roche/Chugai |
| IL-6R | Sapelizumab | Chugai |
| IL-6R | Vobarilizumab | Ablynx |
| L1CAM | AB417 | Creative biolabs |
| L1CAM | L1-9.3 | Creative biolabs |
| L1CAM | L1-14.10 | Biolegend |
| NGF | Tanezumab | Pfizer |
| NGF | Fulranumab (JNJ-42160443), | Amgen |
| NGF | MNAC13 (anti-TrkA, the NGF receptor) | Creative Biolabs |
| NGF | mAb 911 | Rinat/Pfizer |
| NGF | Fasinumab | Regeneron/Teva |
| NRG1 | 538.24 | Hoffman-La Roche |
| NRP1 | Vesencumab | Genentech/Roche |
| ROR1 | Cirmtuzumab | Oncternal Therapeutics |
| SAP | GSK2398852 | GlaxoSmithKline |
| TGFβ | Fresolimumab (pan-TGFβ antibody) | Genzyme/Aventis |
| TGFβ | IMC-TR1 (LY3022859) (MAb against TGFβRII) | Eli Lilly |
| TGFβ | TβM1 (anti-TGFβ1 MAb) | Eli Lilly |
| TGFβ2 | Lerdelimumab (CAT-152) | Genzyme |
| TGFβ1 | Metelimumab | Genzyme |
| TGFβ1 | LY2382770 | Eli Lilly |
| TGFβ | PF-03446962 (MAb against TGFβRI) | Pfizer |
| TNF | Infliximab | Janssen Biotech, Inc. |
| TNF | Adalimumab | AbbVie Inc. |
| TNF | Certolizumab pegol | UCB |
| TNF | Golimumab | Janssen Biotech, Inc. |
| TNF | Afelimomab | |
| TNF | Placulumab | Teva Pharmaceutical Industries, Inc. |
| TNF | Nerelimomab | Chiron/Celltech |
| TNF | Ozoralizumab | Pfizer/Ablynx |
| VEGFA | Bevacizumab | Genentech |
| VEGFA | Ranibizumab | Genentech |
| VEGF | Alacizumab pegol (anti-VEGFR2) | UCB |
| VEGFA | Brolucizumab | Novartis |
| VEGF | Icrucumab (anti-VEGFR1) | Eli Lilly |
| VEGF | Ramucirumab (anti-VEGFR2) | Eli Lilly |

Neuronal growth factor modulators also include agents that agonize or antagonize neuronal growth factors and neuronal growth factor receptors. For example, neuronal growth factor modulators include TNF inhibitors (e.g., etanercept, thalidomide, lenalidomide, pomalidomide, pentoxifylline, bupropion, and DOI), TGFβ1 inhibitors, (e.g., disitertide (P144)), TGFβ2 inhibitors (e.g., trabedersen (AP12009)). Exemplary neuronal growth factor agonists and antagonists are listed in Table 15.

TABLE 15

NEURONAL GROWTH FACTOR AGONISTS AND ANTAGONISTS

| | Agonist | Antagonist |
|---|---|---|
| TrkA | NGF, amitriptyline, and gambogic amide, gambogic acid | ALE-0540 |
| TrkB | BDNF, NT3, NT4, 3,7-Dihydroxyflavone, 3,7,8,2'-Tetrahydroxyflavone, 4'-Dimethylamino-7,8-dihydroxyflavone, 7,3'-Dihydroxyflavone, 7,8-Dihydroxyflavone, 7,8,2'-Trihydroxyflavone, 7,8,3'-Trihydroxyflavone, Amitriptyline, Deoxygedunin, Diosmetin, HIOC, LM22A-4, N-Acetylserotonin, Norwogonin (5,7,8-THF), R7, LM22A4, and TDP6 | ANA-12, cyclotraxin B, and gossypetin |
| Pan-Trk receptor | | entrectinib (RXDX-101), AG 879, GNF 5837, GW 441756, and PF 06273340 |
| GFRα1R | GDNF and XIB4035 | |
| VEGF receptor | | AEE 788, AG 879, AP 24534, axitinib, DMH4, GSK 1363089, Ki 8751, RAF 265, SU 4312, SU 5402, SU 5416, SU 6668, sunitinib, toceranib, vatalanib, XL 184, ZM 306416, and ZM 323881 |
| TGFβRI | | galunisertib (LY2157299), TEW-7197, SB-431542, A 83-01, D 4476, GW 788388, LY 364947, R 268712, RepSox, SB 505124, SB 525334, and SD 208 |

In any of the combination therapy approaches described herein, the first and second therapeutic agent (e.g., a SERCA pump inhibitor described herein and the additional therapeutic agent) are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Diagnosis and Prognosis of SERCA Pump-Associated Cancer

The methods described herein include methods of diagnosing or identifying patients with SERCA pump-associated cancer. Subjects who can be diagnosed or identified as having SERCA pump-associated cancer are subjects who have cancer (e.g., subjects identified as having cancer), or subjects suspected of having cancer. Subjects can be diagnosed or identified as having SERCA pump-associated cancer based on screening of patient cancer samples (e.g., tumor biopsies containing immune cells or isolated immune cells, e.g., Tregs). SERCA pump expression (e.g., the expression of one or more of ATP2A1, ATP2A2, or ATP2A3) can be assessed in a cancer sample isolated from a subject using standard techniques known in the art, such as immunohistochemistry, western blot analysis, quantitative RT-PCR, RNA sequencing, fluorescent in situ hybridization, cDNA microarray, and droplet digital PCR. SERCA pump expression can be assessed by comparing measurements obtained from subject cancer samples to measurements of SERCA pump expression obtained from a reference sample (e.g., an immune cell of the same type from a subject that does not have cancer or a cell that does not express SERCA pumps, e.g., a HEK cell). Reference samples can be obtained from healthy subjects (e.g., subjects without cancer), or they can be obtained from databases in which average measurements of SERCA pump expression are cataloged for immune cells from healthy subjects (e.g., subjects without cancer).

Subjects are diagnosed or identified as having SERCA pump-associated cancer if SERCA pump expression (e.g., the expression of one or more of ATP2A1, ATP2A2, or ATP2A3) is elevated in the sample isolated from the subject (e.g., an immune cell, e.g., an effector T cell, a helper T cell, a cytotoxic T cell (e.g., a CD8+ T cell), a Th1 cell, a Th2 cell, or a Th17 cell) compared to the reference sample. An increase of SERCA pump expression of 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) in the sample isolated from the subject compared to the reference indicates that the subject has SERCA pump-associated cancer. Subjects can also be diagnosed or identified as having SERCA pump-associated cancer (e.g., a cancer in which SERCA pump is functional in immune cells, e.g., effector T cells, helper T cells, cytotoxic T cells (e.g., a CD8+ T cells), Th1 cells, Th2 cells, or Th17 cells) by contacting the immune cell isolated from the subject with a radioligand (e.g., [3H]ryanodine) and evaluating the binding of the radioligand to the immune cell. In some embodiments, radioligand binding to the immune cell indicates that the immune cell expresses a functional SERCA pump (e.g., a SERCA pump that is capable of binding to a ligand, e.g., the subject has SERCA pump-associated cancer). Subjects diagnosed or identified as having SERCA pump-associated cancer can be treated with the methods and compositions described herein (e.g., SERCA pump inhibitors). Subjects with cancer can also be treated with the methods and compositions described herein if an immune cell from the subject (e.g., an immune cell from a tumor biopsy or an isolated immune cell, e.g., an effector T cell, a helper T cell, a cytotoxic T cell (e.g., a CD8+ T cell), a Th1 cell, a Th2 cell, or a Th17 cell) is found to express a SERCA pump.

The methods described herein also include methods of predicting patient response (e.g., the response of cancer in a subject) to SERCA pump inhibitors in order to determine whether SERCA pump inhibitors can be used for cancer treatment. In some embodiments, a sample (e.g., a tumor biopsy containing immune cells or an isolated immune cell, e.g., an effector T cell, a helper T cell, a cytotoxic T cell (e.g., a CD8+ T cell), a Th1 cell, a Th2 cell, or a Th17 cell) is isolated from a subject and contacted with one or more SERCA pump inhibitors or SERCA pump-specific inhibitors (e.g., samples are cultured and contacted with one or more inhibitors in vitro). The response of the sample isolated from the subject to the one or more SERCA pump inhibitors or SERCA pump-specific inhibitors is evaluated to predict response to treatment. Responses that are evaluated include cancer cell or tumor growth, cancer cell or tumor proliferation, cancer cell or tumor migration, cancer cell or tumor metastasis, cancer cell or tumor invasion, cancer cell or tumor autophagy, cancer cell or tumor death, lymph node innervation, immune cell (e.g., effector T cell, helper T cell, cytotoxic T cell (e.g., CD8+ T cell), Th1 cell, Th2 cell, or Th17 cell) migration, proliferation, recruitment, differentiation, activation, polarization, cytokine production, degranulation, maturation, ADCC, ADCP, antigen presentation, or immune cell (e.g., effector T cell, helper T cell, Th1 cell, Th2 cell, or Th17 cell) SERCA pump expression. A decrease of at least 5% or more (e.g., 5%, 10%, 15%, 20%, 25%, 30%, 40%, 50%, 60%, 70%, 80%, 90%, 99%, or more) in cancer cell or tumor growth, cancer cell or tumor proliferation, cancer cell or tumor migration, cancer cell or tumor metastasis, cancer cell or tumor invasion, immune cell (e.g., effector T cell, helper T cell, cytotoxic T cell (e.g., CD8+ T cell), Th1 cell, Th2 cell, or Th17 cell) SERCA pump expression, or tumor egress in treated cells compared to untreated or control-treated cells, or an increase of at least 5% or more (e.g., 5%, 10%, 15%, 20%, 25%, 30%, 40%, 50%, 60%, 70%, 80%, 90%, 99%, or more) in cancer cell or tumor autophagy, cancer cell or tumor death, immune cell ADCC, immune cell ADCP, migration, proliferation, recruitment, differentiation, activation, polarization, proinflammatory cytokine production, degranulation, or maturation in treated cells compared to untreated or control-treated cells indicates that the cancer would respond to treatment with a SERCA pump inhibitor.

The methods used above to diagnose or identify a subject with SERCA pump-associated cancer can also be used to predict patient response (e.g., the response of cancer in a subject) to treatment with a SERCA pump inhibitor. If the expression of a SERCA pump (e.g., the expression of one or more of ATP2A1, ATP2A2, or ATP2A3) is elevated in a sample isolated from a subject compared to a reference (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more higher in the sample compared to the reference), the subject can be predicted to respond to treatment with a SERCA pump inhibitor. Subjects predicted to respond to treatment with a SERCA pump inhibitor or SERCA pump-specific inhibitor can be treated using the methods and compositions described herein (e.g., SERCA pump inhibitors).

Methods of Treatment

Administration

An effective amount of a SERCA pump inhibitor described herein for treatment of cancer can be administered to a subject by standard methods. For example, the agent can be administered by any of a number of different routes including, e.g., intravenous, intradermal, subcutaneous, percutaneous injection, oral, transdermal (topical), or transmucosal. The SERCA pump inhibitor can be administered orally or administered by injection, e.g., intramuscularly, or intravenously. The most suitable route for administration in any given case will depend on the particular agent administered, the patient, the particular disease or condition being treated, pharmaceutical formulation methods, administration methods (e.g., administration time and administration route), the patients age, body weight, sex, severity of the diseases being treated, the patient's diet, and the patient's excretion rate. The agent can be encapsulated or injected, e.g., in a viscous form, for delivery to a chosen site, e.g., a tumor site. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, and cosmetic appearance and interface properties. One example is a collagen matrix.

The agent (e.g., SERCA pump inhibitor, e.g., polypeptide, small molecule, nucleic acid, or antibody) can be incorporated into pharmaceutical compositions suitable for administration to a subject, e.g., a human. Such compositions typically include the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a SERCA pump inhibitor described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art.

Nucleic acid molecule agents described herein can be administered directly (e.g., therapeutic mRNAs) or inserted into vectors used as gene therapy vectors. Gene therapy vectors can be delivered to a subject by, for example, intravenous injection, local administration (see U.S. Pat. No. 5,328,470) or by stereotactic injection (see, e.g., Chen et al., PNAS 91:3054 1994). The pharmaceutical preparation of the gene therapy vector can include the gene therapy vector in an acceptable diluent, or can include a slow release matrix in which the gene delivery vehicle is embedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015.

Local Administration

The SERCA pump inhibitors described herein can be administered locally, e.g., to the site of cancer in the subject. Examples of local administration include epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect. As an example, for the treatment of a cancer described herein, the SERCA pump inhibitor may be administered locally (e.g., intratumorally) in a compound-impregnated substrate such as a wafer, microcassette, or resorbable sponge placed in direct contact with the affected tissue. Alternatively, the SERCA pump inhibitor is infused into the brain or cerebrospinal fluid using standard methods. A SERCA pump inhibitor for use in the methods described herein can be administered intratumorally. In certain embodiments, the agent is administered to a mucous membrane of the subject.

Combination Therapy

The SERCA pump inhibitors described herein may be administered in combination with one or more additional therapies (e.g., 1, 2, 3 or more additional therapeutic agents). The two or more agents can be administered at the same time (e.g., administration of all agents occurs within 15 minutes, 10 minutes, 5 minutes, 2 minutes or less). The agents can also be administered simultaneously via co-formulation. The two or more agents can also be administered sequentially, such that the action of the two or more agents overlaps and their combined effect is such that the reduction in a symptom, or other parameter related to the disorder is greater than what would be observed with one agent or treatment delivered alone or in the absence of the other. The effect of the two or more treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, local routes, and direct absorption through mucous membrane tissues. The therapeutic agents can be administered by the same route or by different routes. For example, a first therapeutic agent of the combination may be administered by intravenous injection while a second therapeutic agent of the combination can be administered locally in a compound-impregnated microcassette. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

For use in treating cancer, the second agent may be a checkpoint inhibitor, a chemotherapeutic drug, a biologic drug, a biologic cancer agent (e.g., an agent listed in Table 6), a cancer-specific agent (e.g., an agent listed in Table 7), a non-drug therapy, a neurotransmission blocker, or a neuronal growth factor blocker. In one embodiment, the inhibitor of checkpoint is an inhibitory antibody (e.g., a monospecific antibody such as a monoclonal antibody). The antibody may be, e.g., humanized or fully human. In other embodiments, the inhibitor of checkpoint is a fusion protein, e.g., an Fc-receptor fusion protein. In some embodiments, the inhibitor of checkpoint is an agent, such as an antibody, that interacts with a checkpoint protein. In other embodiments, the inhibitor of checkpoint is an agent, such as an antibody, that interacts with the ligand of a checkpoint protein. In one embodiment, the inhibitor of checkpoint is an inhibitor (e.g., an inhibitory antibody or small molecule inhibitor) of CTLA-4 (e.g., an anti-CTLA4 antibody such as ipilimumab or tremelimumab). In one embodiment, the inhibitor of checkpoint is an inhibitor (e.g., an inhibitory antibody or small molecule inhibitor) of PD-1 (e.g., nivolumab; pembrolizumab; pidilizumab/CT-011). In one embodiment, the inhibitor of checkpoint is an inhibitor (e.g., an inhibitory antibody or small molecule inhibitor) of PDL1 (e.g., MPDL3280A/RG7446; MED14736; MSB0010718C; BMS 936559). In one embodiment, the inhibitor of checkpoint is an inhibitor (e.g., an inhibitory antibody or Fc fusion or small molecule inhibitor) of PDL2 (e.g., a PDL2/Ig fusion protein such as AMP 224). In one embodiment, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAGS, VISTA, KIR, 2B4, CD160, CGEN-15049, CHK 1, CHK2, A2aR, B-7 family ligands, or a combination thereof. The second agent may also be an anti-angiogenic drug, e.g., an anti-VEGF antibody, or the second agent may be an oncolytic agent e.g., a chemotherapy, a drug that targets cancer metabolism, an antibody that marks a cancer cell surface for destruction, e.g., rituximab or trastuzumab, an antibody-drug conjugate, e.g., trastuzumab emtansine, a cell therapy, or other commonly-used anti-neoplastic agent.

Dosing

Subjects that can be treated as described herein are subjects with cancer or at risk of developing cancer. The cancer may be a primary tumor or a metastasized tumor. In some embodiments, the cancer is a SERCA pump-associated cancer. Subjects who can be treated with the methods disclosed herein include subjects who have had one or more tumors resected, received chemotherapy or other pharmacological treatment for the cancer, received radiation therapy, and/or received other therapy for the cancer. Subjects who have never previously been treated for cancer can also be treated using the methods described herein.

In some embodiments, the agent is administered in an amount and for a time effective to result in one of (or more, e.g., 2 or more, 3 or more, 4 or more of): (a) reduced tumor size, (b) reduced rate of tumor growth, (c) increased tumor cell death (d) reduced tumor progression, (e) reduced number of metastases, (f) reduced rate of metastasis, (g) reduced tumor migration, (h) reduced tumor invasion, (i) reduced tumor volume, (j) decreased tumor recurrence, (k) increased survival of subject, (l) increased progression free survival of subject.

The methods described herein may include a step of selecting a treatment for a patient. The method includes (a) identifying (e.g., diagnosing) a patient who has cancer or is at risk of developing cancer, and (b) selecting a SERCA pump inhibitor, e.g., a SERCA pump inhibitor described herein, to treat the condition in the patient. In some embodiments, the method includes administering the selected treatment to the subject. In some embodiments, a patient is identified as having cancer based on imaging (e.g., MRI, CT, or PET scan), biopsy, or blood sample (e.g., detection of blood antigen markers, circulating tumor DNA (e.g., by PCR). In some embodiments, a patient is identified as having cancer after presenting with one or more symptoms of a paraneoplastic syndrome (e.g., fever, auto-antibodies directed against nervous system proteins, ataxia, dizziness, nystagmus, difficulty swallowing, loss of muscle tone, loss of fine motor coordination, slurred speech memory loss, vision loss, sleep disturbances, dementia, seizures, dysgeusia, cachexia, anemia, itching, or sensory loss in the limbs). In some embodiments, a patient presents with symptoms of paraneoplastic syndrome and is then identified as having cancer based on imaging (e.g., CT, MRI, or PET scans).

The method may also include (a) identifying (e.g., diagnosing) a patient who has a neoplasm, (b) optionally evaluating the neoplasm for innervation, and (c) selecting a SERCA pump inhibitor (e.g., a SERCA pump inhibitor described herein) to treat the patient if the neoplasm is highly innervated (e.g., if the level of innervation is at least 10% higher (e.g., at least 20%, 30%, 40%, 50%, 60%, 70%, 80% higher) than the level of innervation in control tissue, e.g., non-cancerous tissue of the same subject). Innervation may be measured by staining tissue sections for neural markers e.g., immuno-histochemical staining for tyrosine hydroxylase, vesicular acetylcholine transporter; NGF-Inducible Large External glycoprotein, choline acetyltransferase, parvalbumin, neurofilament protein, Synapsin, synaptophysin, NeuN, NSE, MAP2, Beta III tubulin, 160 kD Neurofilament medium/200 kD Neurofilament Heavy, NSE, PSD93/PSD95, Doublecortin (DCX), c-fos, PSA-NCAM, NeuroD or Beta2, Tau, Calbindin-D28k, Calretinin, Neurofilament Protein (NFP), Glial fibrillary acidic protein (GFAP), S100β, Vimentin and CNPase; or by staining tissue sections with cell-identifying stains, e.g., H&E stain, Nissl Stain, Cresyl violet, Neutral red, Thionine and Toluidine blue, Luxol Fast blue stain, Weigert's Chromium hematoxylin method, Page's iron-eriochrome cyanine R, Dextran Conjugates (Fluorescein, Tetramethylrhodamine, Texas Red, Rhodamine Green), Hydrazides & Biocytins, Isolectin GS-IB4 conjugates, Golgi silver stain, or myelin stain; or by imaging the nervous system, e.g., by MRI, CT, PET, EEG, EMG, Myelogram, or magnetoencephalography. In some embodiments, the neoplasm is selected from: head and neck squamous cell carcinoma, adenoid cystic carcinoma, lymphoma, rhabdomyosarcoma, biliary tract cancer, gastric cancer, pancreatic cancer, prostate cancer, lung cancer, breast cancer, skin cancer (e.g., melanoma), renal cell carcinoma, or colorectal cancer. In some embodiments, the neoplasm is derived from a secretory tissue, glandular tissue, or endocrine or hormonal tissue.

In one embodiment, the method includes (a) identifying (e.g., diagnosing) a patient who has a neoplasm, (b) optionally evaluating the neoplasm for perineural invasion, and (c) selecting a SERCA pump inhibitor to treat the patient if the neoplasm exhibits perineural invasion. In some embodiments, the neoplasm is selected from: head and neck squamous cell carcinoma, adenoid cystic carcinoma, lymphoma, rhabdomyosarcoma, biliary tract cancer, gastric cancer, pancreatic cancer, and prostate cancer.

In one embodiment, the method includes (a) identifying (e.g., diagnosing) a patient who has a neoplasm, (b) optionally evaluating the subject for metastasis to brain or spinal cord, and (c) selecting a SERCA pump inhibitor to treat the patient if the neoplasm exhibits metastasis to brain or spinal cord. In some embodiments, the neoplasm is a lung cancer, breast cancer, skin cancer (e.g., melanoma), lymphoma, renal cell carcinoma, GI tract cancer, prostate cancer, or colorectal cancer.

In one embodiment, the method includes (a) identifying (e.g., diagnosing) a patient who has cancer, (b) optionally evaluating the subject for SERCA pump expression, and (c) selecting a SERCA pump inhibitor to treat the patient if an immune cell associated with the cancer exhibits SERCA pump expression (e.g., if the patient has SERCA pump-associated cancer). In some embodiments, the neoplasm is a lung cancer, breast cancer, skin cancer (e.g., melanoma), lymphoma, renal cell carcinoma, GI tract cancer, prostate cancer, ovarian cancer, uterine cancer, head and neck cancer, esophageal cancer, mesothelioma or colorectal cancer. SERCA pump expression (e.g., the expression of one or more of ATP2A1, ATP2A2, or ATP2A3) can be measured in an immune cell sample collected from a subject using standard techniques known in the art, such as immunohistochemistry, western blot analysis, quantitative RT-PCR, RNA sequencing, fluorescent in situ hybridization, cDNA microarray, and droplet digital PCR. An immune cell sample can be evaluated for expression of a SERCA pump (e.g., the expression of one or more of ATP2A1, ATP2A2, or ATP2A3) by comparison to a reference sample (e.g., an immune cell of the same type from a subject that does not have cancer).

In some embodiments, the method includes administering the selected treatment to the subject.

The method may also include a step of assessing the subject for a parameter of cancer progression or remission, e.g., assessing the subject for one or more (e.g., 2 or more, 3 or more, 4 or more) of: primary tumor size (e.g., by imaging), number of metastases (e.g., by imaging or biopsy), cell death in situ (e.g., by biopsy), blood antigen markers (e.g., by ELISA), circulating tumor DNA (e.g., by PCR), or function of the affected organ (e.g., by a test of circulating enzymes for liver, albuminuria for kidney, lung capacity for lung, etc.).

In some embodiments, the tumor is treated with a SERCA pump inhibitor and a second therapeutic agent. The second therapeutic agent can be selected based on tumor type, tumor tissue of origin, tumor stage, tumor innervation, or mutations in genes expressed by the tumor.

In certain embodiments, a SERCA pump inhibitor administered according to the methods described herein does not have a direct effect on the central nervous system (CNS) or gut. Any effect on the CNS or gut is reduced compared to the effect observed if the SERCA pump inhibitor is administered directly to the CNS or gut. In some embodiments, direct effects on the CNS or gut are avoided by modifying the SERCA pump inhibitor not to cross the BBB, as described herein above, or administering the agent locally to a subject.

Subjects with cancer or at risk of developing cancer are treated with an effective amount of a SERCA pump inhibitor. The methods described herein also include contacting immune cells with an effective amount of a SERCA pump inhibitor. In some embodiments, an effective amount of a SERCA pump inhibitor is an amount sufficient to increase or decrease lymph node innervation, tumor innervation, the development of HEVs or TLOs, immune cell migration, proliferation, recruitment, lymph node homing, lymph node egress, differentiation, tumor homing, tumor egress, activation, polarization, cytokine production, degranulation, maturation, ADCC, ADCP, or antigen presentation. In some embodiments, an effective amount of a SERCA pump inhibitor is an amount sufficient to increase or decrease tumor innervation or nerve activity in a tumor. In some embodiments, an effective amount of a SERCA pump inhibitor is an amount sufficient to treat the cancer or tumor, cause remission, reduce tumor growth, volume, metastasis, migration, invasion, proliferation, or number, increase cancer cell death, increase time to recurrence, or improve survival.

The methods described herein may also include a step of assessing the subject for a parameter of immune response, e.g., assessing the subject for one or more (e.g., 2 or more, 3 or more, 4 or more) of: Th2 cells, T cells, circulating monocytes, neutrophils, peripheral blood hematopoietic stem cells, macrophages, mast cell degranulation, activated B cells, NKT cells, macrophage phagocytosis, macrophage polarization, antigen presentation, immune cell activation, immune cell proliferation, immune cell lymph node homing or egress, T cell differentiation, immune cell recruitment, immune cell migration, lymph node innervation, dendritic cell maturation, HEV development, TLO development, or cytokine production. In embodiments, the method includes measuring a cytokine or marker associated with the particular immune cell type, as listed in Table 3 (e.g., performing an assay listed in Table 3 for the cytokine or marker). In some embodiments, the method includes measuring a chemokine, receptor, or immune cell trafficking molecule, as listed in Tables 4 and 5 (e.g., performing an assay to measure the chemokine, marker, or receptor). The assessing may be performed after the administration, before the first administration and/or during a course a treatment, e.g., after a first, second, third, fourth or later administration, or periodically over a course of treatment, e.g., once a month, or once every 3 months. In one embodiment, the method includes assessing the subject prior to treatment or first administration and using the results of the assessment to select a subject for treatment. In certain embodiments, the method also includes modifying the administering step (e.g., stopping the administration, increasing or decreasing the periodicity of administration, increasing or decreasing the dose of the SERCA pump inhibitor) based on the results of the assessment. For example, in embodiments where increasing a parameter of immune response described herein is desired (e.g., cancer-related embodiments where, e.g., an increase in Th2 cells is desired), the method includes stopping the administration if a marker of Th2 cells is not increased at least 5%, 10%, 15%, 20%, 30%, 40%, 50% or more; or the method includes increasing the periodicity of administration if the marker of Th2 cells is not increased at least 5%, 10%, 15%, 20%, 30%, 40%, 50% or more; or the method includes increasing the dose of the SERCA pump inhibitor if the marker of Th2 cells is not increased at least 5%, 10%, 15%, 20%, 30%, 40%, 50% or more.

In certain embodiments, immune effects (e.g., immune cell activities) are modulated in a subject (e.g., a subject having a cancer or inflammatory or autoimmune condition) or in a cultured cell by at least 1%, 2%, 5%, 10%, 15%, 20%, 25%, 30%, 35%, 40%, 50%, 60%, 70%, 80%, compared to before an administration, e.g., of a dosing regimen, of a SERCA pump inhibitor such as those described herein. In certain embodiments, the immune effects are modulated in the subject or a cultured cell between 5-20%, between 5-50%, between 10-50%, between 20-80%, between 20-70%, between 50-100%, between 100-500%. The immune effects described herein may be assessed by standard methods:

The SERCA pump inhibitors described herein are administered in an amount (e.g., an effective amount) and for a time sufficient to effect one of the outcomes described above. The SERCA pump inhibitor may be administered once or more than once. The SERCA pump inhibitor may be administered once daily, twice daily, three times daily, once every two days, once weekly, twice weekly, three times weekly, once biweekly, once monthly, once bimonthly, twice a year, or once yearly. Treatment may be discrete (e.g., an injection) or continuous (e.g., treatment via an implant or infusion pump). Subjects may be evaluated for treatment efficacy 1 week, 2 weeks, 1 month, 2 months, 3 months, 4 months, 5 months, 6 months or more following administration of a SERCA pump inhibitor depending on the SERCA pump inhibitor and route of administration used for treatment. Depending on the outcome of the evaluation, treatment may be continued or ceased, treatment frequency or dosage may change, or the patient may be treated with a different SERCA pump inhibitor. Subjects may be treated for a discrete period of time (e.g., 1, 2, 3, 4, 5, 6, 7, 8, 9, 10, 11, or 12 months) or until the disease or condition is alleviated, or treatment may be chronic depending on the severity and nature of the disease or condition being treated.

Kits

The invention also features a kit including (a) a pharmaceutical composition containing a SERCA pump inhibitor described herein, and (b) instructions for administering the pharmaceutical composition to treat cancer.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1—Identification of SERCA Pumps on Immune Cells

For human cells, CD8+ T-cells were isolated from human PBMCs using negative magnetic bead selection (Stemcell Technologies) on day 0. Cells were activated with CD3/CD28 Human magnetic polymer particles (Life Technologies) and recombinant human IL-2 (Biolegend). Cells were lysed and RNA was extracted using an RNA extraction kit (Qiagen).

For mouse cells, MC38 tumors were dissociated by mincing with scissors in a collagenase/DNAse mixture in RPMI media. Minced tumors were incubated at 37° C. for 20 min. Crude tumor homogenate was placed onto a 70 µm cell strainer and further homogenized through the filter. Single cells were stained for FACS analysis. CD8+ T-cells were sorted based on the following markers: CD45+, live, CD11b-CD19-CD4-CD8+CD3+TCRB+. Cells were lysed and RNA was extracted (Qiagen).

RNA was sequenced at the Broad Technology Labs (BTL) at the Broad Institute using their Smart-Seq2 protocol, a protocol for full-length transcript sequencing from single cells. Smart-Seq2 libraries were sequenced on a high output sequence machine (Illumina) using a high out-put flow cell and reagent kit to generate 2×25 bp reads (plus dual index reads). Further details are available through the BTL, but in brief, reads were demultiplexed and aligned utilizing an ultrafast RNAseq alignment algorithm (Dobin et al., Bioinformatics. 29:15, 2013) with the following parameters: -twopassMode Basic, -alignIntronMax 1000000, -alignMatesGapMax 1000000, -sjdbScore 2, -quantMode TranscriptomeSAM, and -sjdbOverhang 24.

Quantification of individual read counts was performed using the DESeq2 algorithm (Love et al., Genome Biology 15:550, 2014), a method for differential analysis of count data, using shrinkage estimation for dispersions and fold changes to improve stability and interpretability of estimates. This enabled a more quantitative analysis focused on the strength rather than the mere presence of differential expression. The output of the DESeq2 algorithm was an expression level, in arbitrary units, normalized to an internal factor derived from the sequencing depth of the sample.

SERCA isoforms were found to be expressed in a variety of CD8+ T-cell populations, often modulated in response to activation, as shown in Table 16 below. For mouse T-cells, some SERCA isoforms had higher expression than the bulk of the tumor, suggesting a CD8+ specific expression of SERCA isoforms.

TABLE 16

EXPRESSION OF SERCA PUMP ISOFORMS IN CD8+ T CELLS

| Cell Type | Gene Name | Expression Level |
| --- | --- | --- |
| Human CD8+ T-cells, Naive | ATP2A2 (Entrez: 488) | 11.846 |
| Human CD8+ T-cells, Activated | ATP2A2 (Entrez: 488) | 79.878 |
| Human CD8+ T-cells, Naive | ATP2A3 (Entrez: 489) | 139.371 |
| Human CD8+ T-cells, Activated | ATP2A3 (Entrez: 489) | 66.569 |
| Bulk MC38 Tumor | Atp2a2 (Entrez: 11938) | 342.5 |
| Mouse CD8+ T-cells sorted from MC38 | Atp2a2 (Entrez: 11938) | 181.9 |
| Bulk MC38 Tumor | Atp2a3 (Entrez: 53313) | 6.5 |
| Mouse CD8+ T-cells sorted from MC38 | Atp2a3 (Entrez: 53313) | 629.3 |

Example 2—Modulation of SERCA Pumps in Immune Cells with SERCA Pump Inhibitors

CD8+ T-cells were isolated from human PBMCs using negative magnetic bead selection (Stemcell Technologies). Cells stimulated with anti-CD3/anti-CD28 beads (Life Technologies) and were treated with different SERCA inhibitors: thapsigargin (1.5 µM), cyclopiazonic acid (3 µM), and NS-1619 (30-100 µM). All incubations were done overnight. Subsequent activation was measured by cytokine release using intracellular staining flow cytometry of IFNγ and TNFα, using fluorescently labeled antibodies (Biolegend).

Secretion of the inflammatory cytokine, IFNγ, was increased by CD8+ T cells with the addition of each of the different SERCA inhibitors, as shown in Table 17 below.

TABLE 17

SECRETION OF IFNγ FROM IMMUNE CELLS TREATED WITH SERCA PUMP INHIBITORS

| Sample | Fold Change % IFNγ+ Cells (Normalized to Bead Stimulated Only) |
|---|---|
| CD8+ T-Cell Bead Stimulated Only | 1 |
| CD8+ T-Cell Bead Stimulated + Thapsigargin 1.5 μM | 2.08 |
| CD8+ T-Cell Bead Stimulated + Cyclopiazonic Acid 3 μM | 2.38 |
| CD8+ T-Cell Bead Stimulated + NS-1619 30 μM | 1.1 |
| CD8+ T-Cell Bead Stimulated + NS-1619 100 μM | 2.68 |

Example 3—Treatment of a Patient with Cancer with a SERCA Pump Inhibitor

According to the methods disclosed herein, a physician of skill in the art can treat a patient, such as a human patient with a solid tumor that is a candidate for immunotherapy (e.g., the patient has substantial immune cell infiltration (e.g., infiltration of T cells) into the tumor as assessed by histological analysis of a biopsy), so as to inhibit solid tumor growth, reduce tumor volume, or slow disease progression. The method of treatment can include diagnosing or identifying a patient as a candidate for treatment with a SERCA pump inhibitor based on SERCA pump expression in a biopsy (e.g., a biopsy containing immune cells, e.g., effector T cells, helper T cells, Th1 cells, Th2 cells, or Th17 cells), or in isolated immune cells (e.g., effector T cells, helper T cells, Th1 cells, Th2 cells, or Th17 cells). For example, tissue sample or immune cells (e.g., effector T cells, helper T cells, Th1 cells, Th2 cells, or Th17 cells) can be collected from a patient's cancer and analyzed for RNA expression by qPCR or RNAseq analysis, and the cancer can be found to express high levels of one or more SERCA pumps. To treat the patient, a physician of skill in the art can administer a SERCA pump inhibitor that decreases SERCA pump expression or SERCA pump activity (e.g., a SERCA pump inhibitory antibody or a SERCA pump small molecule inhibitor). The SERCA pump inhibitor can be administered locally (e.g., injected into the tumor or tumor microenvironment) to decrease tumor growth or volume. The SERCA pump inhibitor is administered in a therapeutically effective amount, such as from 10 μg/kg to 500 mg/kg (e.g., 10 μg/kg, 100 μg/kg, 500 μg/kg, 1 mg/kg, 10 mg/kg, 50 mg/kg, 100 mg/kg, 250 mg/kg, or 500 mg/kg). In some embodiments, the SERCA pump inhibitor is administered bimonthly, once a month, once every two weeks, or at least once a week or more (e.g., 1, 2, 3, 4, 5, 6, or 7 times a week or more).

The SERCA pump inhibitor activates the patient's T cells (e.g., increases T cell cytokine production of one or more pro-inflammatory cytokines, e.g., IFNγ). The SERCA pump inhibitor is administered to the patient in an amount sufficient to decrease tumor burden, increase progression free survival, or increase pro-inflammatory cytokine levels by 10% or more (e.g., 10%, 20%, 30%, 40%, 50%, 60%, 70%, 80%, 90%, 95% or more). Cytokine production can be assessed by collecting a blood sample from the patient and evaluating one or more pro-inflammatory cytokines (e.g., IFNγ). The blood sample can be collected one day or more after administration of the SERCA pump inhibitor (e.g., 1, 2, 3, 4, 5, 6, 7, 10, 14, 21, or 30 or more days after administration). The blood sample can be compared to a blood sample collected from the patient prior to administration of the SERCA pump inhibitor (e.g., a blood sample collected earlier the same day, 1 day, 1 week, 2 weeks, one month or more before administration of the SERCA pump inhibitor). Tumor burden can be assessed using standard imaging methods (e.g., digital radiography, positron emission tomography (PET) scan, computed tomography (CT) scan, or magnetic resonance imaging (MRI) scan). Images from before and after administration of the SERCA pump inhibitor can be compared to evaluate the efficacy of the treatment. A finding of a reduction in the total number of tumors, number of primary tumors, volume of tumors, positive lymph nodes, or distant metastases, or an increase in progression free survival indicates that the SERCA pump inhibitor has successfully treated the cancer.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

What is claimed is:

1. A method of increasing a level of interferon gamma in a human subject in need thereof, the method comprising administering to the human subject an amount of a small molecule sarco/endoplasmic reticulum $Ca^{2+}$-ATPase (SERCA) pump antagonist effective to increase interferon gamma production by T cells, wherein the SERCA pump antagonist is cyclopiazonic acid or NS-1619.

2. The method of claim 1, wherein the human subject is identified as having a T cell infiltrated tumor.

3. The method of claim 1, wherein increased interferon gamma has a pro-inflammatory effect.

4. The method of claim 1, wherein the SERCA pump inhibitor or SERCA pump-specific inhibitor is administered locally.

5. The method of claim 1, wherein the SERCA pump inhibitor or SERCA pump-specific inhibitor is administered intratumorally.

6. The method of claim 1, wherein the method further comprises administering a second therapeutic agent.

7. The method of claim 6, wherein the second therapeutic agent comprises an anti-cancer agent, a SERCA pump function blocker, a neurotransmission modulator, or a neuronal growth factor modulator.

8. The method of claim 7, wherein the second therapeutic agent comprises the anti-cancer agent, and wherein the anti-cancer agent comprises a checkpoint inhibitor, a chemotherapeutic agent, a biologic cancer agent, an anti-angiogenic drug, a drug that targets cancer metabolism, an antibody that marks a cancer cell surface for destruction, an antibody-drug conjugate, a cell therapy, a commonly used anti-neoplastic agent, chimeric antigen receptor (CAR)-T therapy, an anti-cancer vaccine, or a non-drug therapy.

9. The method of claim 8, wherein the anti-cancer agent comprises the checkpoint inhibitor, and wherein the checkpoint inhibitor comprises an inhibitory antibody, a fusion protein, an agent that interacts with a checkpoint protein, an agent that interacts with the ligand of a checkpoint protein, an inhibitor of CTLA-4, an inhibitor of PD-1, an inhibitor of PDL1, an inhibitor of PDL2, or an inhibitor of B7-H3, B7-H4, BTLA, HVEM, TIM3, GAL9, LAG3, VISTA, KIR, 2B4, CD160, CGEN-15049, CHK 1, CHK2, A2aR, or B-7 family ligands.

10. The method of claim 2, wherein the SERCA pump inhibitor is administered to the subject in an amount sufficient to treat the T cell infiltrated tumor, cause remission, decrease tumor volume, decrease tumor growth, decrease tumor innervation, decrease tumor proliferation, decrease tumor metastasis, decrease tumor invasion, decrease tumor migration, or increases tumor death, increase tumor autophagy, increase immune cell migration, increase immune cell proliferation, increase immune cell tumor homing, increase immune cell polarization, increase immune cell recruitment, increase immune cell differentiation, increase immune cell activation, increase immune cell cytokine production, decrease immune cell SERCA pump expression, increase antibody dependent cellular cytotoxicity (ADCC), increase ADCP, increase time to recurrence, improve survival, or a combination thereof.

* * * * *